United States Patent [19]

Addor et al.

[11] Patent Number: 5,492,925
[45] Date of Patent: Feb. 20, 1996

[54] THIENYL- AND FURYLPYRROLE INSECTICIDAL AND ACARICIDAL AGENTS

[75] Inventors: Roger W. Addor, Pennington; Joseph A. Furch, III, Lawrenceville; Laurelee A. Duncan, East Windsor, all of N.J.; Jack K. Siddens, deceased, late of Des Moines, Iowa, by Beverly A. Siddens

[73] Assignee: American Cyanamid Company, Wayne, N.J.

[21] Appl. No.: 114,809

[22] Filed: Aug. 31, 1993

[51] Int. Cl.$^6$ .................... C07D 207/34; C07D 233/60; C07D 263/32; C07D 277/22; A01N 43/36; A01N 43/50; A01N 43/76; A01N 43/78

[52] U.S. Cl. .................... 514/422; 514/326; 514/343; 514/367; 514/369; 514/375; 514/376; 514/397; 514/414; 514/63; 514/91; 540/544; 540/602; 544/55; 544/96; 544/315; 546/208; 546/281; 548/165; 548/169; 548/170; 548/171; 548/173; 548/182; 548/186; 548/187; 548/217; 548/221; 548/225; 548/229; 548/306.1; 548/406; 548/465; 548/517; 548/525; 548/527; 548/413

[58] Field of Search .................... 548/517, 525, 548/527, 165, 169, 170, 171, 173, 182, 186, 187, 217, 221, 225, 229, 306.1, 465, 406, 413; 514/422, 367, 369, 375, 376, 397, 414, 63, 91, 343, 326; 546/281, 208; 544/55, 96, 315; 540/544, 602

[56] References Cited

U.S. PATENT DOCUMENTS

| | | | |
|---|---|---|---|
| 4,267,184 | 5/1981 | Cherkofsky | 424/263 |
| 5,010,098 | 4/1991 | Brown et al. | 514/426 |
| 5,102,904 | 4/1992 | Kameswaren | 514/424 |
| 5,157,047 | 10/1992 | Kaweswaren et al. | 514/423 |
| 5,162,308 | 11/1992 | Brown et al. | 514/63 |

FOREIGN PATENT DOCUMENTS

| | | | |
|---|---|---|---|
| 111452A1 | 6/1984 | European Pat. Off. | 548/560 |
| 60-40874 | 3/1985 | Japan | 548/517 |

OTHER PUBLICATIONS

CA95: 203870t New . . . pyrrolothiemopyrimidines, Effi et al., p. 676, 1981.
CA 100: Sulfenylpyrroles as fungicides. p/ 544, 1984.
CA 101: 124892r Use of . . . materials. Nyfeler et al., p. 237, 1984.
CA 116: 106011h Preparation . . . —4–nitropyrroles. Ono et al., p. 747, 1992.
N. Ono, et al., Journal of Heterocyclic Chemistry, 28, pp. 2053–2055, 1991.

Primary Examiner—Joseph K. McKane
Attorney, Agent, or Firm—Gregory M. Hill

[57] ABSTRACT

There are provided thienyl- and furylpyrrole compounds of formula I

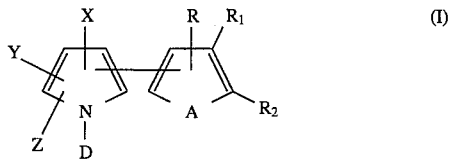

and their use for the control of insects and acarina. Further provided are compositions and methods comprising those compounds for the protection of plants from attack by insects and acarina.

40 Claims, No Drawings

THIENYL- AND FURYLPYRROLE INSECTICIDAL AND ACARICIDAL AGENTS

BACKGROUND OF THE INVENTION

Insects and acarina destroy growing and harvested crops. In the United States alone, agronomic crops must compete with thousands of insect and acarid species. In particular, tobacco budworms, southern armyworms and two-spotted spider mites are especially devasting to crops.

Tobacco budworms cause tremendous economic losses in agronomic crops. In particular, budworms devastate cotton crops by feeding on green bolls. Control of budworms is complicated by their resistance to many common insecticides, including organophosphates, carbamates and pyrethroids. Also, budworm larvae are difficult to control with currently available insecticides once they reach the third instar.

Two-spotted spider mites attack many plant species, raspberry plants for example, by removing sap from leaves. When raspberry plants are heavily infested, canes and leaves become stunted. With a severe infestation, fruiting canes are damaged, resulting in reduced yield and fruit quality.

In spite of the commercial insecticides and acaricides available today, damage to crops, both growing and harvested, caused by insects and acarina still occurs. Accordingly, there is ongoing research to create new and more effective insecticides and acaricides.

Certain pyrrole compounds are known to possess acaricidal, fungicidal, insecticidal and/or antiinflammatory activity (see, e.g., U.S. Pat. Nos. 4,267,184; 5,010,098; 5,102,904; 5,157,047 and 5,162,308, U.S. patent application Ser. Nos. 621,162 filed on Nov. 30, 1990; 803,289 filed on Dec. 4, 1991; 966,990 filed on Oct. 27, 1992; 966,992 filed on Oct. 27, 1992; 967,091 filed on Oct. 27, 1992 and 971,025 filed on Nov. 11, 1992, Japanese Patent Application JP-85-40874 filed on Mar. 1, 1985, European Patent Application EP-111452-A1 filed on Jun. 20, 1984, and N. Ono et al, Journal of Heterocyclic Chemistry, 28, pages 2053–2055 (1991)). However, none of the pyrroles disclosed in those patents, patent applications and publication are within the scope of the present invention.

It is therefore an object of the present invention to provide compounds which are highly effective for controlling insects and acarina.

It is also an object of the present invention to provide a method for controlling insects and acarina.

It is a further object of this invention to provide a method for protecting growing plants from attack by insects and acarina.

These and other objects of the present invention will become more apparent from the detailed description thereof set forth below.

SUMMARY OF THE INVENTION

The present invention describes thienyl- and furylpyrrole compounds which are useful as insecticidal and acaricidal agents for the control of insects and acarina and for the protection of plants from attack by insects and acarina.

The thienyl- and furylpyrrole compounds of the present invention have the following structural formula I:

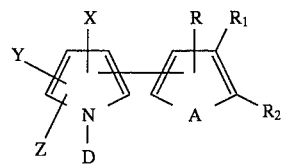

wherein

R, $R_1$ and $R_2$ are each independently hydrogen, halogen, $NO_2$ or CHO, and when $R_1$ and $R_2$ are taken together with the carbon atoms to which they are attached, they may form a ring in which $R_1R_2$ is represented by the structure:

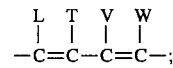

L, T, V and W are each independently hydrogen, halogen, CN or $NO_2$;

A is O or S;

X is CN, $NO_2$, $C_1$–$C_6$ haloalkyl, $S(O)_mCF_2R_3$ or $C(S)NR_4R_5$;

$R_3$ is hydrogen, F, Cl, Br, $CF_2H$, $CCl_2H$, $CClFH$, $CF_3$ or $CCl_3$;

m is an integer of 0, 1 or 2;

$R_4$ and $R_5$ are each independently hydrogen, $C_1$–$C_4$ alkyl optionally substituted with one or more halogen atoms, or phenyl optionally substituted with one or more halogen atoms, $NO_2$ groups, CN groups, $C_1$–$C_4$ alkyl groups optionally substituted with one or more halogen atoms, or $C_1$–$C_4$ alkoxy groups optionally substituted with one or more halogen atoms;

Y is hydrogen, halogen, $C_1$–$C_6$ haloalkyl, $S(O)_mCF_2R_3$, CN or phenyl optionally substituted with one or more halogen atoms, $NO_2$ groups, CN groups, $C_1$–$C_4$ alkyl groups optionally substituted with one or more halogen atoms, or $C_1$–$C_4$ alkoxy groups optionally substituted with one or more halogen atoms;

Z is hydrogen, halogen or $C_1$–$C_6$ haloalkyl;

D is $R_6$, $OR_6$ or CN;

$R_6$ is hydrogen, $C(O)R_7$, $CHR_8NHC(O)R_9$, $CH_2SQ$, $CHR_{10}OC(O)$ $(CR_{11}R_{12})_nQ_1$, $C_1$–$C_6$ alkyl optionally substituted with one to three halogen atoms, one tri($C_1$–$C_4$ alkyl)silyl, one hydroxy, one cyano, one or two $C_1$–$C_4$ alkoxy groups optionally substituted with one to three halogen atoms, one $C_1$–$C_4$ alkylthio, one phenyl optionally substituted with one to three halogen atoms, one to three $C_1$—$C_4$ alkyl groups or one to three $C_1$–$C_4$ alkoxy groups, one phenoxy group optionally substituted with one to three halogen atoms, one to three $C_1$–$C_4$ alkyl groups or one to three $C_1$–$C_4$ alkoxy groups, one benzyloxy group optionally substituted on the phenyl ring with one to three halogen atoms, one to three $C_1$–$C_4$ alkyl groups or one to three $C_1$–$C_4$ alkoxy groups, one $C_1$–$C_6$ alkylcarbonyloxy group optionally substituted with one to three halogen atoms, one $C_2$–$C_6$ alkenylcarbonyloxy group optionally substituted with one to three halogen atoms, one phenylcarbonyloxy group optionally substituted with one to three halogen atoms, one to three $C_1$–$C_4$ alkyl groups or one to three $C_1$–$C_4$ alkoxy groups, one $C_1$–$C_6$ alkoxycarbonyl group optionally substituted with one to three halogen atoms or one to three $C_1$–$C_4$ alkoxy groups, or one benzylcarbonyloxy group optionally substituted on the phenyl ring with one to three halogen atoms, one to three $C_1$–$C_4$ alkyl groups or one to three $C_1$–$C_4$ alkoxy groups, $C_3$–$C_6$ alkenyl optionally substituted with one to three halogen atoms or one phenyl group, or $C_3$–$C_6$ alkynyl optionally substituted with one to three halogen atoms or one phenyl group;

$R_7$ is $C_1$–$C_6$ alkyl or $C_3$–$C_6$ cycloalkyl each optionally substituted with one to three halogen atoms, one hydroxy, one cyano, one or two $C_1$–$C_4$ alkoxy groups optionally substituted with one to three halogen atoms, one $C_1$–$C_4$ alkylthio, one phenyl group optionally substituted with one to three halogen atoms, one to three $C_1$–$C_4$ alkyl groups or one to three $C_1$–$C_4$ alkoxy groups, one phenoxy group optionally substituted with one to three halogen atoms, one to three $C_1$–$C_4$ alkyl groups or one to three $C_1$–$C_4$ alkoxy groups, one benzyloxy group optionally substituted on the phenyl ring with one to three halogen atoms, one to three $C_1$–$C_4$ alkyl groups or one to three $C_1$–$C_4$ alkoxy groups, one $C_1$–$C_6$ alkylcarbonyloxy group optionally substituted with one to three halogen atoms, one $C_2$–$C_6$ alkenylcarbonyloxy group optionally substituted with one to three halogen atoms, one phenylcarbonyloxy group optionally substituted with one to three halogen atoms, one to three $C_1$–$C_4$ alkyl groups or one to three $C_1$–$C_4$ alkoxy groups, one $C_1$–$C_6$ alkoxycarbonyl group optionally substituted with one to three halogen atoms or one to three $C_1$–$C_4$ alkoxy groups, or one benzyloxycarbonyl group optionally substituted on the phenyl ring with one to three halogen atoms, one to three $C_1$–$C_4$ alkyl groups or one to three $C_1$–$C_4$ alkoxy groups, $C_2$–$C_6$ alkenyl optionally substituted with one to three halogen atoms or one phenyl group, $C_3$–$C_6$ alkynyl optionally substituted with one to three halogen atoms or one phenyl group, phenyl optionally substituted with one or more halogen atoms, $C_1$–$C_4$ alkyl groups, $C_1$–$C_4$ alkoxy groups, phenoxy groups, $C_1$–$C_4$ alkylthio groups, tri($C_1$–$C_4$ alkyl)silyl groups, $C_1$–$C_4$ alkylsulfinyl groups, $C_1$–$C_4$ alkylsulfonyl groups, CN groups, $NO_2$ groups or $CF_3$ groups, phenoxy optionally substituted with one or more halogen atoms, $C_1$–$C_4$ alkyl groups, $C_1$–$C_4$ alkoxy groups, $C_1$–$C_4$ alkylthio groups, tri($C_1$–$C_4$ alkyl)silyl groups, $C_1$–$C_4$ alkylsulfinyl groups, $C_1$–$C_4$ alkylsulfonyl groups, CN groups, $NO_2$ groups or $CF_3$ groups, 1- or 2-naphthyl, 2-, 3-, or 4-pyridyl optionally substituted with one to three halogen atoms, $C_1$–$C_6$ alkoxy optionally substituted with one to three halogen atoms, or $C_2$–$C_6$ alkenyloxy optionally substituted with one to three halogen atoms;

$R_8$ is hydrogen or $C_1$–$C_4$ alkyl;

$R_9$ is $C_1$–$C_6$ alkyl optionally substituted with one to three halogen atoms, phenyl optionally substituted with one to three halogen atoms, CN groups, $NO_2$ groups, $C_1$–$C_4$ alkyl groups, $C_1$–$C_4$ alkoxy groups or $CF_3$ groups, 2- or 3-thienyl, or 2- or 3-furyl;

Q is $$\overset{A_1}{\underset{}{\overset{\|}{C}}}-R_{13}, \quad \overset{A_1}{\underset{}{\overset{\|}{C}}}-OR_{14},$$

$$\overset{A_1}{\underset{}{\overset{\|}{C}}}-NR_{15}R_{16}, \quad \overset{A_1}{\underset{}{\overset{\|}{P}}}-(OR_{17})_2,$$

$$\overset{NR_{18}}{\underset{}{\overset{\|}{C}}}-NR_{19}R_{20}, \quad \overset{NR_{18}}{\underset{}{\overset{\|}{C}}}-A_1R_{21},$$

[pyrrole/thiazole-type ring structures with $A_1$, $R_{22}$, $R_{23}$, N, and H,N substituents]

CN, $C_1$–$C_6$ alkyl optionally substituted with one or more halogen atoms, CN groups or phenyl groups, or phenyl optionally substituted with one or more halogen atoms, $C_1$–$C_4$ alkyl groups, $C_1$–$C_4$ alkoxy groups, CN groups, $NO_2$ groups, $CF_3$ groups or $NR_{24}R_{25}$ groups;

$A_1$ is O or S;

$R_{13}$ is $C_1$–$C_6$ alkyl or phenyl;

$R_{14}$ is $C_1$–$C_6$ alkyl;

$R_{15}$ and $R_{16}$ are each independently hydrogen, $C_1$–$C_6$ alkyl or may be taken together with the atom to which they are attached to form a 5- to 7-membered ring;

$R_{17}$ is $C_1$–$C_4$ alkyl;

$R_{18}$ is hydrogen, $C_1$–$C_4$ alkyl or may be taken together with either $R_{19}$ or $R_{21}$ and the atoms to which they are attached to form a 5- to 7-membered ring optionally substituted with one or two $C_1$–$C_4$ alkyl groups;

$R_{19}$ and $R_{20}$ are each independently hydrogen or $C_1$–$C_4$ alkyl;

$R_{21}$ is $C_1$–$C_4$ alkyl or when taken together with $R_{18}$ and the atoms to which they are attached may form a 5- to 7-membered ring optionally substituted with one or two $C_1$–$C_4$ alkyl groups;

$R_{22}$ and $R_{23}$ are each independently hydrogen or $C_1$–$C_4$ alkyl or when taken together may form a ring wherein $R_{22}R_{23}$ is represented by —CH=CH—CH=CH—;

$R_{24}$ and $R_{25}$ are each independently hydrogen or $C_1$–$C_4$ alkyl;

$R_{10}$ is hydrogen or $C_1$–$C_4$ alkyl;

$R_{11}$ and $R_{12}$ are each independently hydrogen, $C_1$–$C_6$ alkyl optionally substituted with one or more halogen atoms, $C_1$–$C_6$ alkoxy optionally substituted with one or more halogen atoms, $C_1$–$C_6$ alkylthio optionally substituted with one or more halogen atoms, or phenyl optionally substituted with one or more halogen atoms, NO$_2$ groups;
CN groups,
C$_1$–C$_4$ alkyl groups optionally substituted with one or more halogen atoms, or
C$_1$–C$_4$ alkoxy groups optionally substituted with one or more halogen atoms, or
when R$_{11}$ and R$_{12}$ are taken together with the atom to which they are attached may form a C$_3$–C$_6$ cycloalkyl group optionally substituted with one to three C$_1$–C$_4$ alkyl groups, C$_2$–C$_6$ alkenyl groups or phenyl groups, or R$_{11}$ or R$_{12}$ may be taken together with R$_{26}$ and the atoms to which they are attached to form a 4- to 7-membered heterocyclic ring;
n is an integer of 0, 1, 2, 3 or 4;
Q$_1$ is A$_2$R$_{26}$,

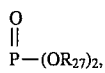

NR$_{28}$R$_{29}$, CR$_{30}$R$_{31}$C(O)R$_{32}$, or
C$_3$–C$_6$ cycloalkyl optionally substituted with one or more
C$_1$–C$_6$ alkyl groups,
C$_2$–C$_6$ alkenyl groups, or
phenyl groups optionally substituted with one or more halogen atoms,
NO$_2$ groups,
CN groups,
C$_1$–C$_4$ alkyl groups optionally substituted with one or more halogen atoms, or
C$_1$–C$_4$ alkoxy groups optionally substituted with one or more halogen atoms;
A$_2$ is O or S(O)$_p$;
p is an integer of 0, 1 or 2;
R$_{26}$ is hydrogen,
C$_1$–C$_6$ alkyl
C$_2$–C$_6$ alkenyl,
C$_2$–C$_6$ alkynyl,
phenyl optionally substituted with one or more halogen atoms,
NO$_2$ groups,
CN groups,
C$_1$–C$_4$ alkyl groups optionally substituted with one or more halogen atoms, or
C$_1$–C$_4$ alkoxy groups optionally substituted with one or more halogen atoms,
C(O)R$_{33}$ provided p is O,
C(O)R$_{34}$ provided p is O,
(CH$_2$CH$_2$O)$_q$R$_{33}$, or

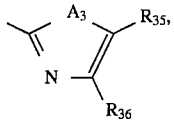

R$_{26}$ may be taken together with either R$_{11}$ or R$_{12}$ and the atoms to which they are attached to form a 4- to 7-membered heterocyclic ring;
A$_3$ is O or S;
R$_{33}$ is C$_1$–C$_6$ alkyl,
C$_2$–C$_6$ alkenyl,
C$_2$–C$_6$ alkynyl, or
phenyl optionally substituted with one or more halogen atoms,
NO$_2$ groups,
CN groups,
C$_1$–C$_4$ alkyl groups optionally substituted with one or more halogen atoms, or
C$_1$–C$_4$ alkoxy groups optionally substituted with one or more halogen atoms;
q is an integer of 1, 2 or 3;
R$_{34}$ is OR$_{37}$ or NR$_{38}$R$_{39}$;
R$_{37}$ is C$_1$–C$_6$ alkyl or
phenyl optionally substituted with one or more halogen atoms,
NO$_2$ groups,
CN groups,
C$_1$–C$_4$ alkyl groups optionally substituted with one or more halogen atoms, or
C$_1$–C$_4$ alkoxy groups optionally substituted with one or more halogen atoms;
R$_{38}$ and R$_{39}$ are each independently hydrogen or C$_1$–C$_4$ alkyl;
R$_{35}$ and R$_{36}$ are each independently hydrogen or C$_1$–C$_4$ alkyl, or
when taken together may form a ring wherein
R$_{35}$R$_{36}$ is represented by —CH=CH—CH=CH—;
R$_{27}$ is C$_1$–C$_4$ alkyl;
R$_{28}$ is hydrogen,
C$_1$–C$_6$ alkyl,
C$_2$–C$_6$ alkenyl,
C$_2$–C$_6$ alkynyl, or
phenyl optionally substituted with one or more halogen atoms,
NO$_2$ groups,
CN groups,
C$_1$–C$_4$ alkyl groups optionally substituted with one or more halogen atoms, or
C$_1$–C$_4$ alkoxy groups optionally substituted with one or more halogen atoms, or
R$_{28}$ may be taken together with either R$_{11}$ or R$_{12}$ and the atoms to which they are attached to form a 4- to 7-membered heterocyclic ring;
R$_{29}$ is hydrogen,
C$_1$–C$_6$ alkyl,
C$_2$–C$_6$ alkenyl,
C$_2$–C$_6$ alkynyl,
phenyl optionally substituted with one or more halogen atoms,
NO$_2$ groups,
CN groups,
C$_1$–C$_4$ alkyl groups optionally substituted with one or more halogen atoms, or
C$_1$–C$_4$ alkoxy groups optionally substituted with one or more halogen atoms,
C(A$_4$)R$_{40}$,
CN,
SO$_2$R$_{41}$, or
C(O)CHR$_{42}$NHR$_{43}$;
A$_4$ is O or S;
R$_{40}$ is OR$_{44}$, CO$_2$R$_{44}$, NR$_{45}$R$_{46}$,
C$_1$–C$_6$ alkyl optionally substituted with one to three halogen atoms,
C$_2$–C$_6$ alkenyl,
C$_2$–C$_6$ alkynyl, or
phenyl optionally substituted with one or more halogen atoms,
NO$_2$ groups, CN groups, $C_1-C_4$ alkyl groups optionally substituted with one or more halogen atoms, or $C_1-C_4$ alkoxy groups optionally substituted with one or more halogen atoms;

$R_{44}$ is $C_1-C_6$ alkyl optionally substituted with one phenyl group, or phenyl optionally substituted with one or more halogen atoms, NO$_2$ groups, CN groups, $C_1-C_4$ alkyl groups optionally substituted with one or more halogen atoms, or $C_1-C_4$ alkoxy groups optionally substituted with one or more halogen atoms;

$R_{45}$ and $R_{46}$ are each independently hydrogen or $C_1-C_4$ alkyl;

$R_{41}$ is $NR_{47}R_{48}$, $C_1-C_6$ alkyl, $C_2-C_6$ alkenyl, $C_2-C_6$ alkynyl, or phenyl optionally substituted with one or more halogen atoms, NO$_2$ groups, CN groups, $C_1-C_4$ alkyl groups optionally substituted with one or more halogen atoms, or $C_1-C_4$ alkoxy groups optionally substituted with one or more halogen atoms;

$R_{47}$ and $R_{48}$ are each independently hydrogen or $C_1-C_4$ alkyl;

$R_{42}$ is hydrogen, $C_1-C_4$ alkyl optionally substituted with one hydroxy group, one $SR_{49}$ group, one $C(O)NH_2$ group, one $NH_2$ group, one $NHC(=NH)NH_2$ group, one $CO_2H$ group, one phenyl group optionally substituted with one hydroxy group, one 3-indolyl group or one 4-imidazolyl group;

$R_{49}$ is hydrogen or $C_1-C_4$ alkyl;

$R_{43}$ is $C(A_4)R_{50}$;

$R_{50}$ is $C_1-C_6$ alkyl optionally substituted with one or more halogen atoms, $C_1-C_6$ alkoxyalkyl, $C_1-C_6$ alkylthio, phenyl optionally substituted with one or more halogen atoms, NO$_2$ groups, CN groups, $C_1-C_4$ alkyl groups optionally substituted with one or more halogen atoms, or $C_1-C_4$ alkoxy groups optionally substituted with one or more halogen atoms, $OR_{44}$, $CO_2R_{44}$ or $NR_{45}R_{46}$;

$R_{30}$ and $R_{31}$ are each independently hydrogen, $C_1-C_6$ alkyl optionally substituted with one or more halogen atoms, $C_1-C_6$ alkoxy optionally substituted with one or more halogen atoms, $C_1-C_6$ alkylthio optionally substituted with one or more halogen atoms, phenyl optionally substituted with one or more halogen atoms, CN groups, NO$_2$ groups, $C_1-C_4$ alkyl groups optionally substituted with one or more halogen atoms, or $C_1-C_4$ alkoxy groups optionally substituted with one or more halogen atoms, or when $R_{30}$ and $R_{31}$ are taken together with the atom to which they are attached may form a $C_3-C_6$ cycloalkyl group optionally substituted with one to three $C_1-C_4$ alkyl groups, $C_2-C_6$ alkenyl groups or phenyl groups;

$R_{32}$ is $OR_{51}$, $NR_{47}R_{48}$, $C_1-C_4$ alkyl or phenyl optionally substituted with one or more halogen atoms, CN groups, NO$_2$ groups, $C_1-C_4$ alkyl groups optionally substituted with one or more halogen atoms, or $C_1-C_4$ alkoxy groups optionally substituted with one or more halogen atoms; and $R_{51}$ is $C_1-C_4$ alkyl or phenyl optionally substituted with one or more halogen atoms, CN groups, NO$_2$ groups, $C_1-C_4$ alkyl groups optionally substituted with one or more halogen atoms, or $C_1-C_4$ alkoxy groups optionally substituted with one or more halogen atoms;

provided that when A is S, X is $S(O)_mCF_2R_3$ and Z is hydrogen, then Y is hydrogen, halogen, $C_1-C_6$ haloalkyl, $S(O)_mCF_2R_3$ or CN; and further provided that when the pyrrole ring is substituted with hydrogen at each of the pyrrole carbon atoms adjacent to the ring nitrogen atom, then X cannot be CN or NO$_2$.

This invention also relates to compositions containing those compounds and methods for using those compounds and compositions. Advantageously, it has been found that the thienyl- and furylpyrrole compounds of the present invention, and compositions containing them, are effective insecticidal and acaricidal agents for the control of insects and acarina and for the protection of plants from attack by insects and acarina. The compounds of the present invention are especially useful for the control of tobacco budworms and southern armyworms.

DETAILED DESCRIPTION OF THE INVENTION

Advantageously, the present invention provides a method for controlling insects and acarina by contacting said insects and acarina, their breeding ground, food supply or habitat with an insecticidally or acaricidally effective amount of a formula I, thienyl- or furylpyrrole compound.

The present invention also provides a method for protecting growing plants from attack by insects and acarina by applying to the foliage of said plants or to the soil or water in which they are growing an insecticidally or acaricidally effective amount of a formula I, thienyl- or furylpyrrole compound.

The thienyl- and furylpyrrole compounds of the present invention have the following structural formula I:

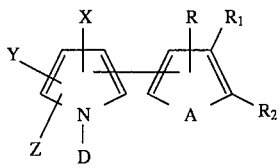

(I)

wherein R, $R_1$, $R_2$, A, X, Y, Z and B are as described hereinabove for formula I.

Preferred formula I thienyl- and furylpyrrole compounds of the present invention are those wherein R, $R_1$ and $R_2$ are each independently hydrogen, halogen or $NO_2$, and when $R_1$ and $R_2$ are taken together with the carbon atoms to which they are attached, they may form a ring in which $R_1R_2$ is represented by the structure:

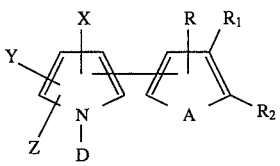

(I)

L, T, V and W are each independently hydrogen, halogen, CN or $NO_2$;
A is O or S;
X is CN, $NO_2$, $C_1$–$C_6$ haloalkyl, $S(O)_mCF_2R_3$ or $C(S)NR_4R_5$;
$R_3$ is hydrogen, F, Cl, Br, $CF_2H$, $CCl_2H$, $CClFH$, $CF_3$ or $CCl_3$;
m is an integer of 0, 1 or 2;
$R_4$ and $R_5$ are each independently hydrogen,
  $C_1$–$C_4$ alkyl optionally substituted with one or more halogen atoms, or
  phenyl optionally substituted with one or more halogen atoms,
    $NO_2$ groups,
    CN groups,
    $C_1$–$C_4$ alkyl groups optionally substituted with one or more halogen atoms, or
    $C_1$–$C_4$ alkoxy groups optionally substituted with one or more halogen atoms;
Y is hydrogen, halogen, $C_1$–$C_6$ haloalkyl, $S(O)_mCF_2R_3$, CN or
  phenyl optionally substituted with one or more halogen atoms,
    $NO_2$ groups,
    CN groups,
    $C_1$–$C_4$ alkyl groups optionally substituted with one or more halogen atoms, or
    $C_1$–$C_4$ alkoxy groups optionally substituted with one or more halogen atoms;
Z is hydrogen, halogen or $C_1$–$C_6$ haloalkyl;
D is $R_6$ or CN;
$R_6$ is hydrogen, $C(O)R_7$, or
  $C_1$–$C_6$ alkyl optionally substituted with one to three halogen atoms,
    one cyano,
    one $C_1$–$C_4$ alkoxy group,
    one $C_1$–$C_6$ alkylcarbonyloxy group,
    one phenylcarbonyloxy group, or
    one benzylcarbonyloxy group; and
$R_7$ is phenyl optionally substituted with one or more halogen atoms, $C_1$–$C_4$ alkyl groups, $C_1$–$C_4$ alkoxy groups, CN groups, $NO_2$ groups or $CF_3$ groups.

Another group of preferred formula I insecticidal and acaricidal agents are those wherein R, $R_1$ and $R_2$ are each independently hydrogen, halogen or $NO_2$, and when $R_1$ and $R_2$ are taken together with the carbon atoms to which they are attached, they may form a ring in which $R_1R_2$ is represented by the structure:

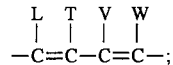

L, T, V and W are each independently hydrogen, halogen, CN or $NO_2$;
A is O or S;
X is CN, $NO_2$ or $C_1$–$C_6$ haloalkyl;
Y is hydrogen, halogen, $C_1$–$C_6$ haloalkyl or phenyl optionally substituted with one or more halogen atoms,
    $NO_2$ groups,
    CN groups,
    $C_1$–$C_4$ alkyl groups optionally substituted with one or more halogen atoms, or
    $C_1$–$C_4$ alkoxy groups optionally substituted with one or more halogen atoms;
Z is hydrogen, halogen or $C_1$–$C_6$ haloalkyl;
D is $R_6$ or CN;
$R_6$ is hydrogen, $C(O)R_7$ or
  $C_1$–$C_6$ alkyl optionally substituted with one to three halogen atoms,
    one cyano,
    one $C_1$–$C_4$ alkoxy group,
    one $C_1$–$C_6$ alkylcarbonyloxy group,
    one phenylcarbonyloxy group, or
    one benzylcarbonyloxy group; and
$R_7$ is phenyl optionally substituted with one or more halogen atoms, $C_1$–$C_4$ alkyl groups, $C_1$–$C_4$ alkoxy groups, CN groups, $NO_2$ groups or $CF_3$ groups.

More preferred formula I thienyl- and furylpyrrole compounds of this invention are those wherein R, $R_1$ and $R_2$ are each independently hydrogen, halogen or $NO_2$, and when $R_1$ and $R_2$ are taken together with the carbon atoms to which they are attached, they may form a ring in which $R_1R_2$ is represented by the structure:

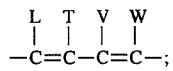

L, T, V and W are each independently hydrogen, halogen, CN or $NO_2$;
A is O or S;
X is CN, $NO_2$ or $C_1$–$C_6$ haloalkyl;
Y is hydrogen, halogen, $C_1$–$C_6$ haloalkyl or
  phenyl optionally substituted with one or more halogen atoms,
    $NO_2$ groups,
    CN groups,
    $C_1$–$C_4$ alkyl groups optionally substituted with one or more halogen atoms, or
    $C_1$–$C_4$ alkoxy groups optionally substituted with one or more halogen atoms;
Z is halogen or $C_1$–$C_6$ haloalkyl;
D is $R_6$ or CN;
$R_6$ is hydrogen, $C(O)R_7$ or
  $C_1$–$C_6$ alkyl optionally substituted with one to three halogen atoms,
    one cyano,
    one $C_1$–$C_4$ alkoxy group,
    one $C_1$–$C_6$ alkylcarbonyloxy group,
    one phenylcarbonyloxy group, or
    one benzylcarbonyloxy group; and $R_7$ is phenyl optionally substituted with one or more halogen atoms, $C_1$–$C_4$ alkyl groups, $C_1$–$C_4$ alkoxy groups, CN groups, $NO_2$ groups or $CF_3$ groups.

Another group of more preferred formula I thienyl- and furylpyrrole compounds of this invention which are effective insecticidal and acaricidal agents are those wherein R, $R_1$ and $R_2$ are each independently hydrogen, halogen or $NO_2$, and when $R_1$ and $R_2$ are taken together with the carbon atoms to which they are attached, they may form a ring in which $R_1R_2$ is represented by the structure: —CH=CH—CH=CH—;

A is O or S;

X is CN or $NO_2$;

Y is halogen, $CF_3$ or phenyl optionally substituted with one or more halogen atoms, $NO_2$ groups, CN groups, $C_1$–$C_4$ alkyl groups optionally substituted with one or more halogen atoms, or $C_1$–$C_4$ alkoxy groups optionally substituted with one or more halogen atoms;

Z is hydrogen, halogen or $CF_3$; and

D is hydrogen or $C_1$–$C_6$ alkyl substituted with one $C_1$–$C_4$ alkoxy group.

Most preferred formula I insecticidal and acaricidal agents are those wherein

R, $R_1$ and $R_2$ are each independently hydrogen, halogen or $NO_2$;

A is O or S;

X is CN or $NO_2$;

Y is halogen, $CF_3$ or phenyl optionally substituted with one or more halogen atoms, $NO_2$ groups, CN groups, $C_1$–$C_4$ alkyl groups optionally substituted with one or more halogen atoms, or $C_1$–$C_4$ alkoxy groups optionally substituted with one or more halogen atoms;

Z is $CF_3$; and

D is hydrogen or $C_1$–$C_6$ alkyl substituted with one $C_1$–$C_4$ alkoxy group.

Exemplary of halogen hereinabove are fluorine, chlorine, bromine and iodine. The term "$C_1$–$C_6$ haloalkyl" is defined as a $C_1$–$C_6$ alkyl group substituted with one or more halogen atoms.

Advantageously, it has been found that the formula I compounds of the present invention are especially useful for the control of tobacco budworms, southern armyworms and two-spotted spider mites.

Thienyl- and furylpyrrole compounds of formula I wherein X is CN and Y, Z and B are hydrogen may be prepapred by reacting an N-formyl(thienyl or furyl)glycine of formula II with 2-chloroacrylonitrile and acetic anhydride as shown in Flow Diagram I.

FLOW DIAGRAM I

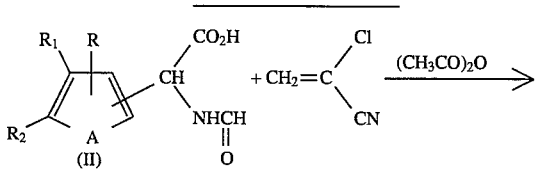

FLOW DIAGRAM I -continued

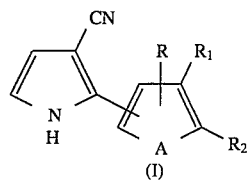

Certain compounds of formula I wherein X is CN, Y is $C_1$–$C_6$ haloalkyl and Z and B are hydrogen may be prepared by reacting the appropriately substituted thienyl- or furylglycine of formula III with a $C_1$–$C_6$ haloalkyl acid anhydride to form an oxazolinone intermediate of formula IV and reacting said formula IV intermediate with 2-chloroacrylonitrile as shown in Flow Diagram II.

FLOW DIAGRAM II

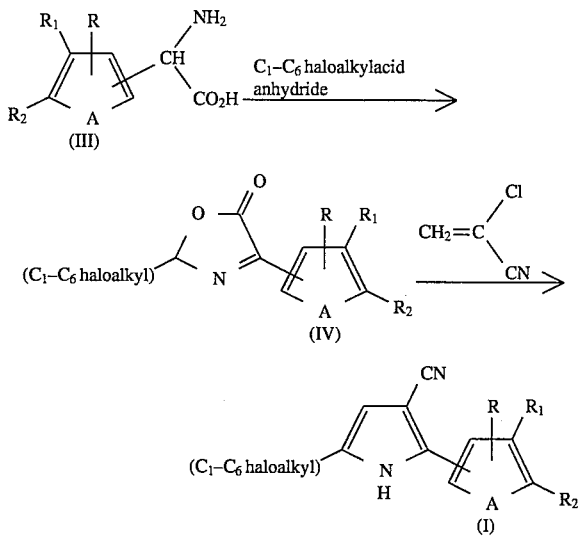

Formula I compounds wherein X and Y are $C_1$–$C_6$ haloalkyl and Z and D are hydrogen may be prepared by reacting an oxazolinone of formula IV with a bromoalkene of formula V as shown in Flow Diagram III.

FLOW DIAGRAM III

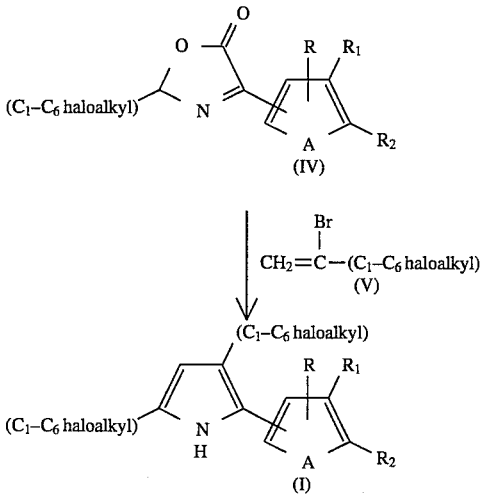

4-Cyano-2-(thienyl- or furyl)pyrrole compounds may be prepared by reacting acrylonitrile with an N-(trimethylsilyl)methyl-5-methyl-(thienyl- or furyl)thioimidate of formula VI in the presence of tetrabutylammonium fluoride to form a 2-(thienyl- or furyl)-1-pyrroline-4-carbonitrile intermediate of formula VII and reacting said formula VII intermediate with 2,3-dichloro-5,6-dicyano-1,4-benzoquinone and pyridine as shown below in Flow Diagram IV.

FLOW DIAGRAM IV

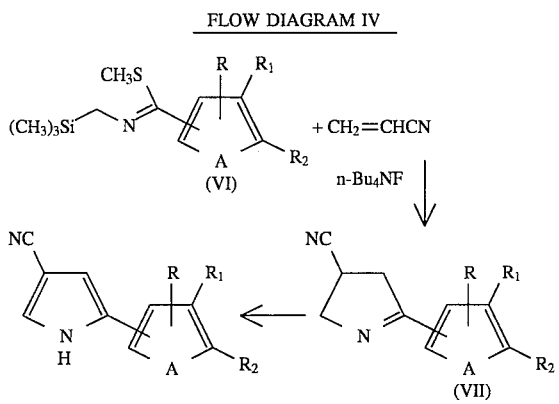

3-Cyano or nitro-2-thienylpyrrole compounds may be prepared as shown below in Flow Diagram V.

FLOW DIAGRAM V

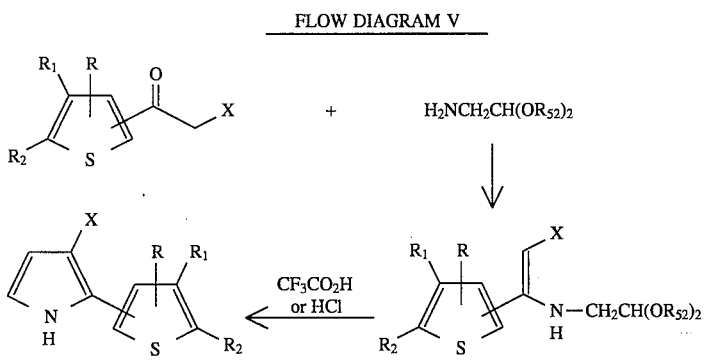

wherein

R, $R_1$ and $R_2$ are each independently hydrogen, halogen or $NO_2$, and when $R_1$ and $R_2$ are taken together with the carbon atoms to which they are attached, they may form a ring in which $R_1R_2$ is represented by the structure:

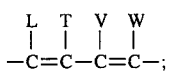

L, T, V and W are each independently hydrogen, halogen, CN or $NO_2$;

X is CN or $NO_2$; and $R_{52}$ is $C_1$–$C_4$ alkyl.

2-(Thienyl- or furyl)pyrrole-3,4-dicarbonitrile compounds may be prepared as shown below in Flow Diagram VI.

FLOW DIAGRAM VI

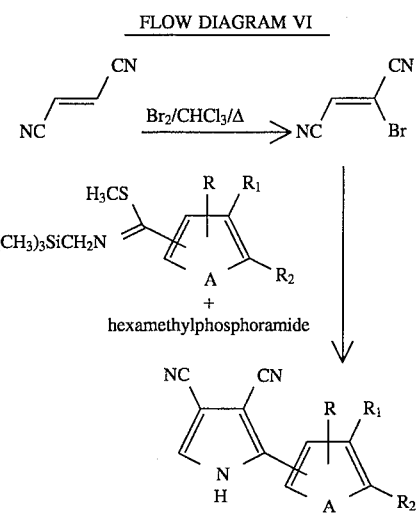

Formula I compounds wherein X is $C(S)NH_2$ may be prepared by reacting the appropriately substituted formula VIII (thienyl- or furyl)pyrrole-carbonitrile with an excess of hydrogen peroxide and sodium hydroxide to give the appropriately substituted formula IX (thienyl- or furyl)pyrrole carboxamide and reacting said formula IX carboxamide with a reagent capable of introducing the thioxo group, such as 2,4-bis(4-methoxyphenyl)-1,3-dithia-2,4-diphosphetane-2,4-disulfide as shown below in Flow Diagram VII.

FLOW DIAGRAM VII

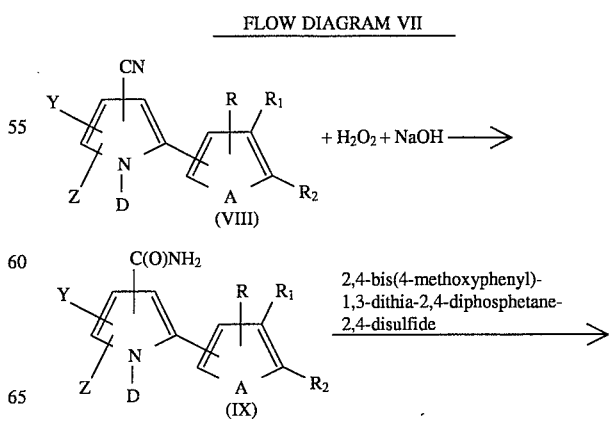

-continued
FLOW DIAGRAM VII

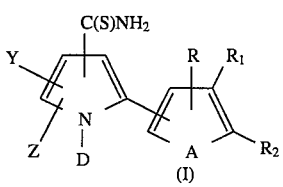
(I)

wherein

A, D, Y and Z are as described hereinabove for formula I;

R, $R_1$ and $R_2$ are each independently hydrogen, halogen or $NO_2$, and when $R_1$ and $R_2$ are taken together with the carbon atoms to which they are attached, they may form a ring in which $R_1R_2$ is represented by the structure:

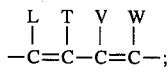

L, T, V and W are each independently hydrogen, halogen, CN or $NO_2$.

4-(Thienyl- or furyl)pyrrole-3-thiocarboxamide compounds may be prepared by reacting the appropriately substituted formula X aldehyde with triethyl phosphonoacetate, lithium chloride and triethylamine to form the ester of formula XI. The formula XI ester is reacted with a strong base such as sodium hydride and tosylmethyl isocyanide to form a formula XII ethyl 4-(thienyl- or furyl)pyrrole-3-carboxylate which is hydrolyzed with an alkali metal hydroxide such as potassium hydroxide to form a formula XIII 4-(thienyl- or furyl)pyrrole-3-carboxylic acid. The formula XIII carboxylic acid is reacted with a tri($C_1$–$C_4$ alkyl)amine to form a first mixture. The first mixture is reacted with thionyl chloride and N,N-dimethylformamide to give a second mixture. The second mixture is reacted with a formula XIV amine compound to give the formula XV 4-(thienyl- or furyl)pyrrole-3-carboxamide and reacting the formula XV carboxamide with a reagent capable of introducing the thioxo group, such as 2,4-bis(4-methoxyphenyl)-1,3-dithia-2,4-diphosphetane-2,4-disulfide, to give the desired 4-(thienyl- or furyl)pyrrole- 3-thiocarboxamide. The above reaction schemes are shown below in Flow Diagram VIII.

FLOW DIAGRAM VIII

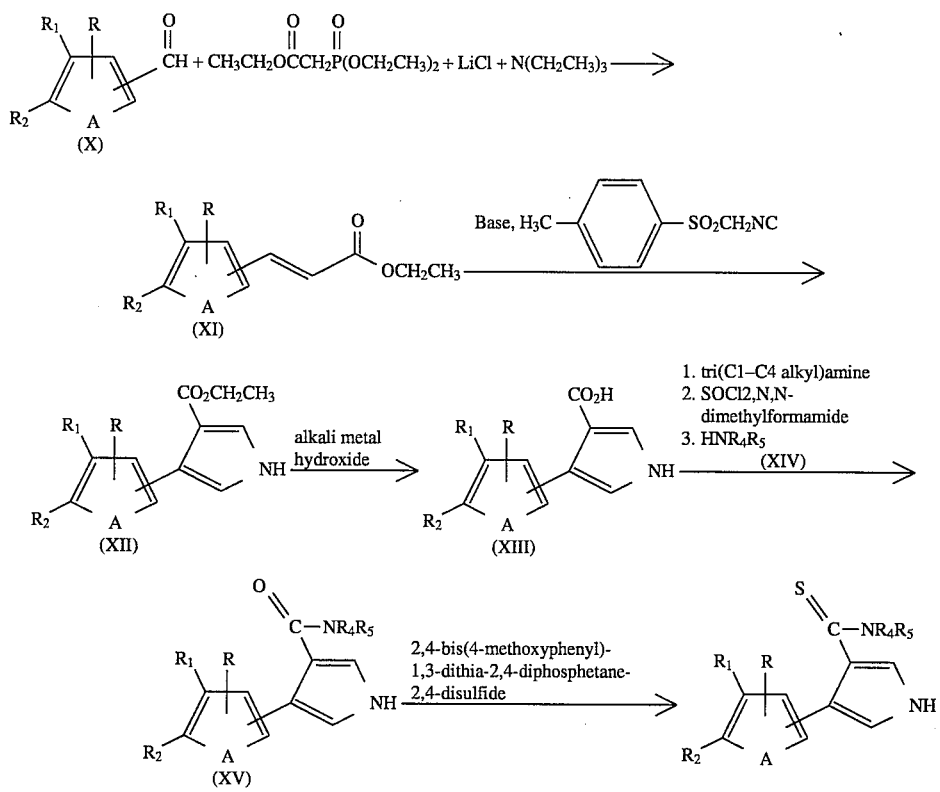

wherein

A, $R_4$ and $R_5$ are as described hereinabove for formula I;

R, $R_1$ and $R_2$ are each independently hydrogen, halogen or $NO_2$, and when $R_1$ and $R_2$ are taken together with the carbon atoms to which they are attached, they may form a ring in which $R_1R_2$ is represented by the structure:

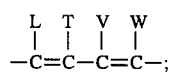

L, T, V and W are each independently hydrogen, halogen, CN or $NO_2$.

2-(Thienyl- and furyl)-1-hydroxypyrrole-3-carbonitrile compounds may be prepared by reacting a formula XVI ester with an acetal of cyanopropionaldehyde in the presence of sodium hydride to form an acetal of formula XVII and reacting the formula XVII acetal with hydroxylamine hydrochloride as shown in Flow Diagram IX.

5-(Thienylpyrrole-2,3-dicarbonitrile compounds of formula I may be prepared by reacting a formula XVIII oxime with sodium oxalacetate to form a formula XIX intermediate which is reacted with hydrochloric acid in the presence of an alcohol to form a formula XX 5-thienyl-1-hydroxypyrrole-3-carboxylate. The formula XX carboxylate is reacted with

FLOW DIAGRAM IX

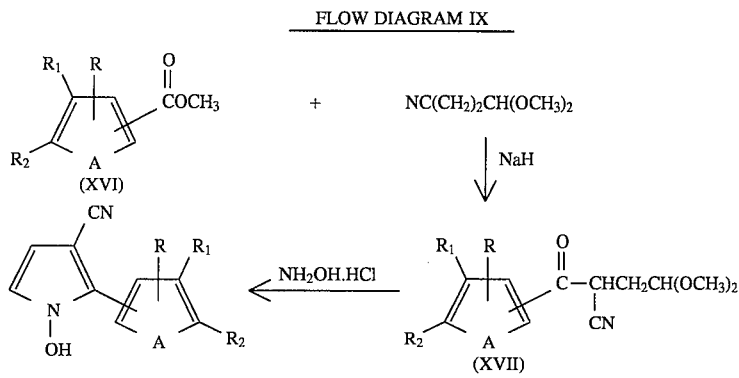

wherein

A is O or S;

R, $R_1$ and $R_2$ are each independently hydrogen, halogen or $NO_2$, and when $R_1$ and $R_2$ are taken together with the carbon atoms to which they are attached, they may form a ring in which $R_1R_2$ is represented by the structure:

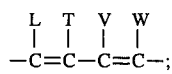

L, T, V and W are each independently hydrogen, halogen, CN or $NO_2$.

methyl iodide and potassium t-butoxide to give a formula XXI 5-thienyl-1-methoxypyrrole-3-carboxylate. Saponification of the formula XXI carboxylate gives a formula XXII 5-thienyl-1-methoxypyrrole-3-carboxylic acid which is reacted with chlorosulfonyl isocyanate and N,N-dimethylformamide to give the formula I 5-thienylpyrrole- 2,3-dicarbonitrile. The above reaction scheme is shown in Flow Diagram X.

FLOW DIAGRAM X

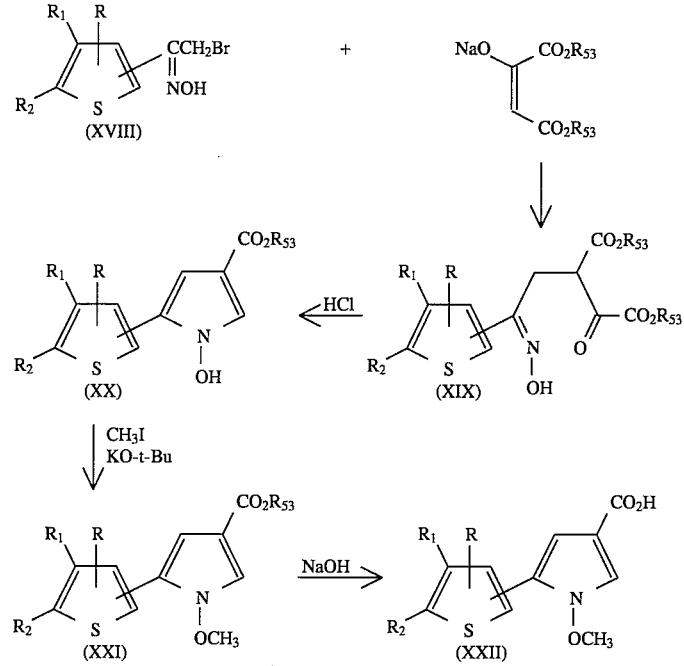

-continued
FLOW DIAGRAM X

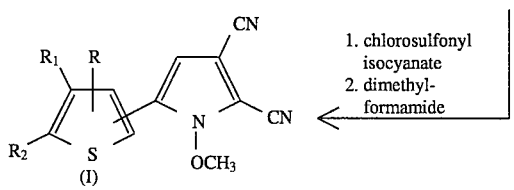

wherein

R, $R_1$ and $R_2$ are each independently hydrogen, halogen or $NO_2$, and when $R_1$ and $R_2$ are taken together with the carbon atoms to which they are attached, they may form a ring in which $R_1R_2$ is represented by the structure:

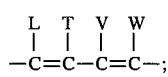

L, T, V and W are each independently hydrogen, halogen, CN or $NO_2$; and $R_{53}$ is $C_1$–$C_6$ alkyl or $C_3$–$C_6$ cycloalkyl.

2,4-Dibromo-5-(2-thienyl)-1-methoxypyrrole- 3-carbonitrile compounds of the present invention may be prepared by reacting a formula XXIII 5-(2-thienyl)- 1-methoxypyrrole-3-carboxylate with bromine to form a formula XXIV 2,4-dibromo-5-(2-thienyl)-1-methoxypyrrole- 3-carboxylate. Saponification of the formula XXIV carboxylate gives a formula XXV acid which is reacted with chlorosulfonyl isocyanate and dimethylformamide to give the desired 2,4-dibromno-5-(2-thienyl)- 1-methoxypyrrole-3-carbonitrile. The above reaction scheme is shown in Flow Diagram XI.

FLOW DIAGRAM XI

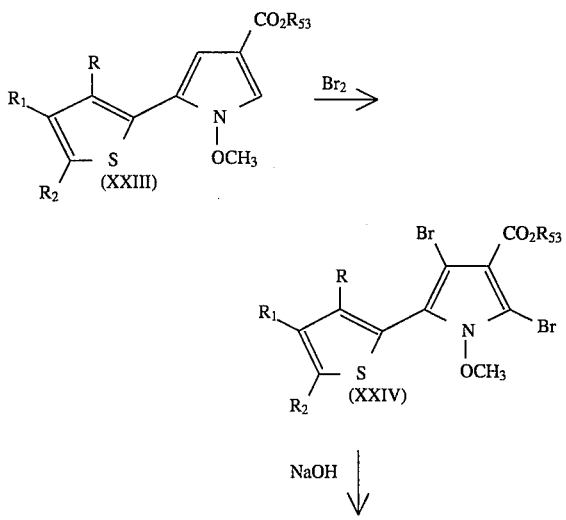

-continued
FLOW DIAGRAM XI

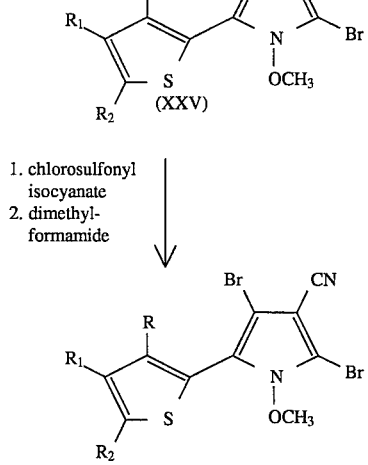

wherein

R and $R_1$ are each independently hydrogen, halogen or $NO_2$, and when $R_1$ is taken together with $R_2$ and the carbon atoms to which they are attached, they may form a ring in which $R_1R_2$ is represented by the structure:

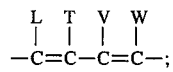

$R_2$ is halogen, and when taken together with $R_1$ and the carbon atoms to which they are attached, they may form a ring in which $R_1R_2$ is represented by the structure:

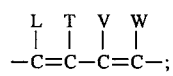

L, T, V and W are each independently hydrogen, halogen, CN or $NO_2$; and $R_{53}$ is $C_1$–$C_6$ alkyl or $C_3$–$C_6$ cycloalkyl.

Similarly, 2,4-dibromo-5-(3-thienyl)-1-methoxypyrrole-3-carbonitrile compounds may be prepared as shown in Flow Diagram XII.

FLOW DIAGRAM XII

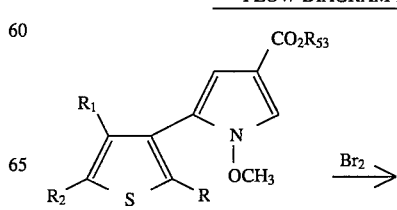

21
-continued
FLOW DIAGRAM XII

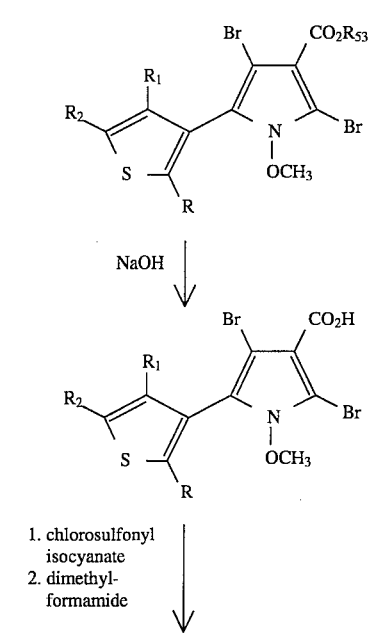

1. chlorosulfonyl isocyanate
2. dimethylformamide

22
-continued
FLOW DIAGRAM XII

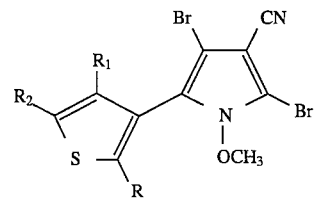

wherein $R_1$ is hydrogen, halogen or $NO_2$, and when $R_1$ is taken together with $R_2$ and the carbon atoms to which they are attached, they may form a ring in which $R_1R_2$ is represented by the structure:

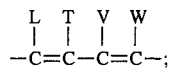

R and $R_2$ are each independently halogen, and when $R_2$ is taken together with $R_1$ and the carbon atoms to which they are attached, they may form a ring in which $R_1R_2$ is represented by the structure:

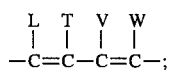

L, T, V and W are each independently hydrogen, halogen, CN or $NO_2$; and $R_{53}$ is $C_1$–$C_6$ alkyl or $C_3$–$C_6$ cycloalkyl.

4-Bromo-2-($C_1$–$C_6$ haloalkyl)-5-(2-thienyl)-1-methoxypyrrole- 3-carbonitrile compounds of the present invention may be prepared as shown in Flow Diagram XIII.

FLOW DIAGRAM XIII

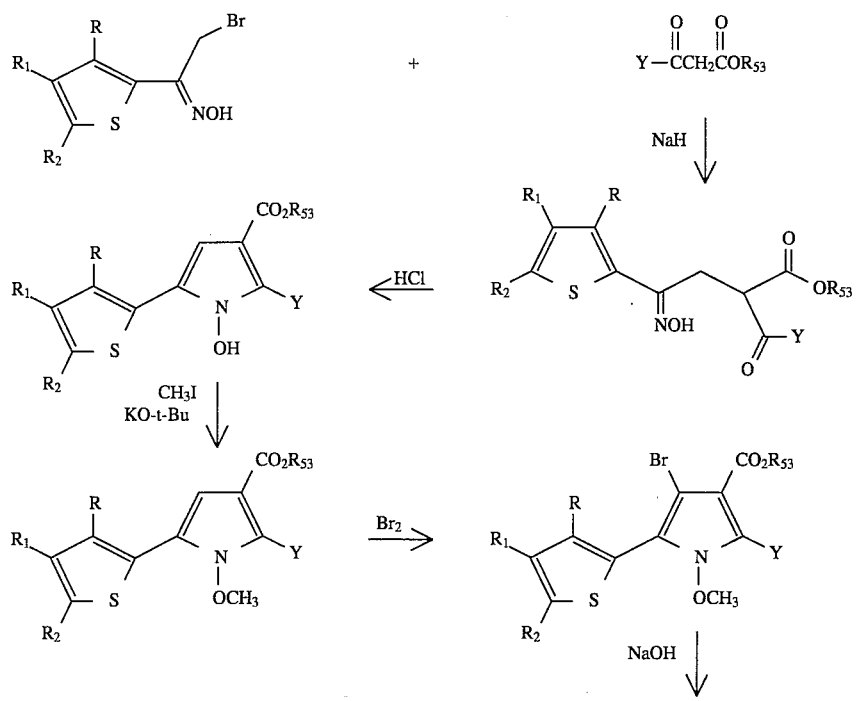

-continued
FLOW DIAGRAM XIII

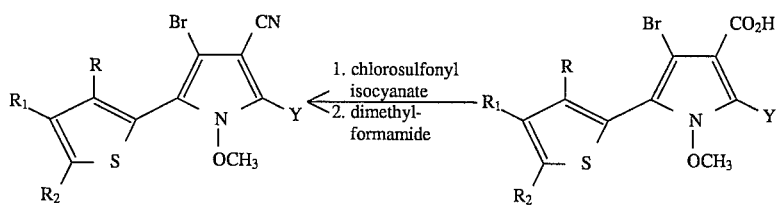

wherein Y is $C_1$–$C_6$ haloalkyl and R, $R_1$, $R_2$ and $R_{53}$ are as described in Flow Diagram XI.

Similarly, 4-bromo-2-($C_1$–$C_6$ haloalkyl)-5-(3-thienyl)-1-methoxypyrrole-3-carbonitrile compounds may be prepared as shown in Flow Diagram XIV.

thienyl)-1-methoxypyrrole-3-carboxylate. Saponification and bromination of the 2-cyano-5-(2-thienyl)-1-methoxypyrrole-3-carboxylate compound gives the desired 3,4-dibromo-5-(2-thienyl)-1-methoxypyrrole-2-carbonitrile as shown in Flow Diagram XV.

FLOW DIAGRAM XIV

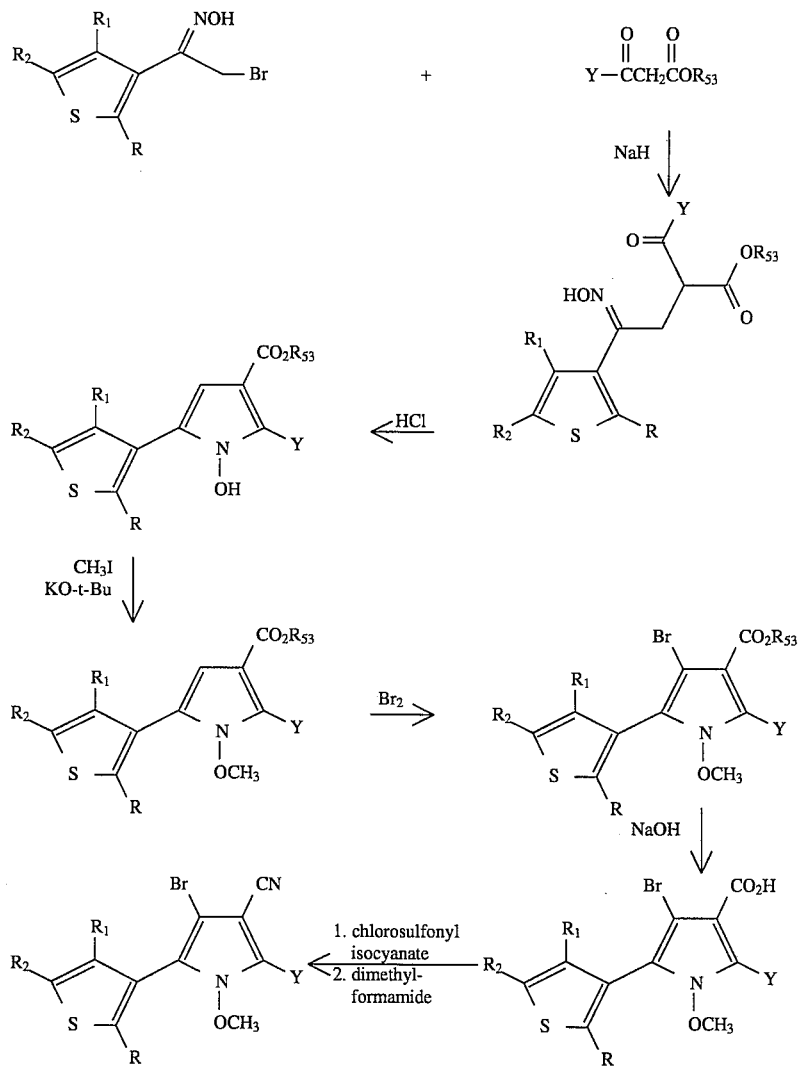

wherein Y is $C_1$–$C_6$ haloalkyl and R, $R_1$, $R_2$ and $R_{53}$ are as described in Flow Diagram XII.

3,4-Dibromo-5-(2-thienyl)-1-methoxypyrrole-2-carbonitrile compounds may be prepared by reacting a 5-(2-thienyl)-1-methoxypyrrole-3-carboxylate with chlorosulfonyl isocyanate and dimethylformamide to give a 2-cyano-5-(2-

FLOW DIAGRAM XV

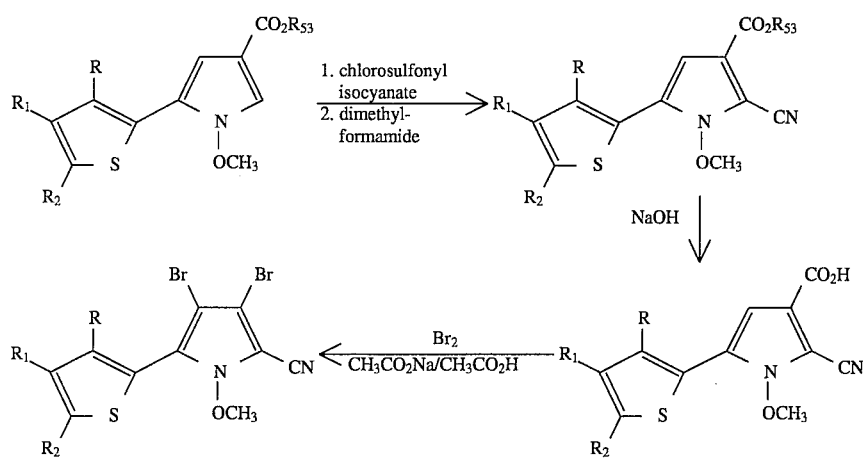

wherein R, $R_1$, $R_2$ and $R_{53}$ are as described in Flow Diagram XI.

Similarly, 3,4-dibromo-5-(3-thienyl)-1-methoxypyrrole-2-carbonitrile compounds may be prepared as shown in Flow Diagram XVI.

Formula I 2-bromo-3-nitro-5-($C_1$–$C_6$ haloalkyl)- 4-(2-thienyl)-1-methoxypyrrole compounds may be prepared as shown in Flow Diagram XVII.

FLOW DIAGRAM XVI

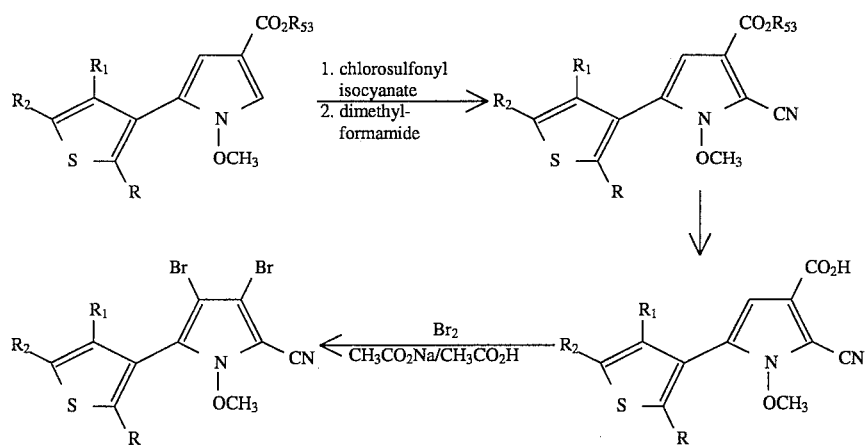

wherein R, $R_1$, $R_2$ and $R_{53}$ are as described in Flow Diagram XII.

FLOW DIAGRAM XVII
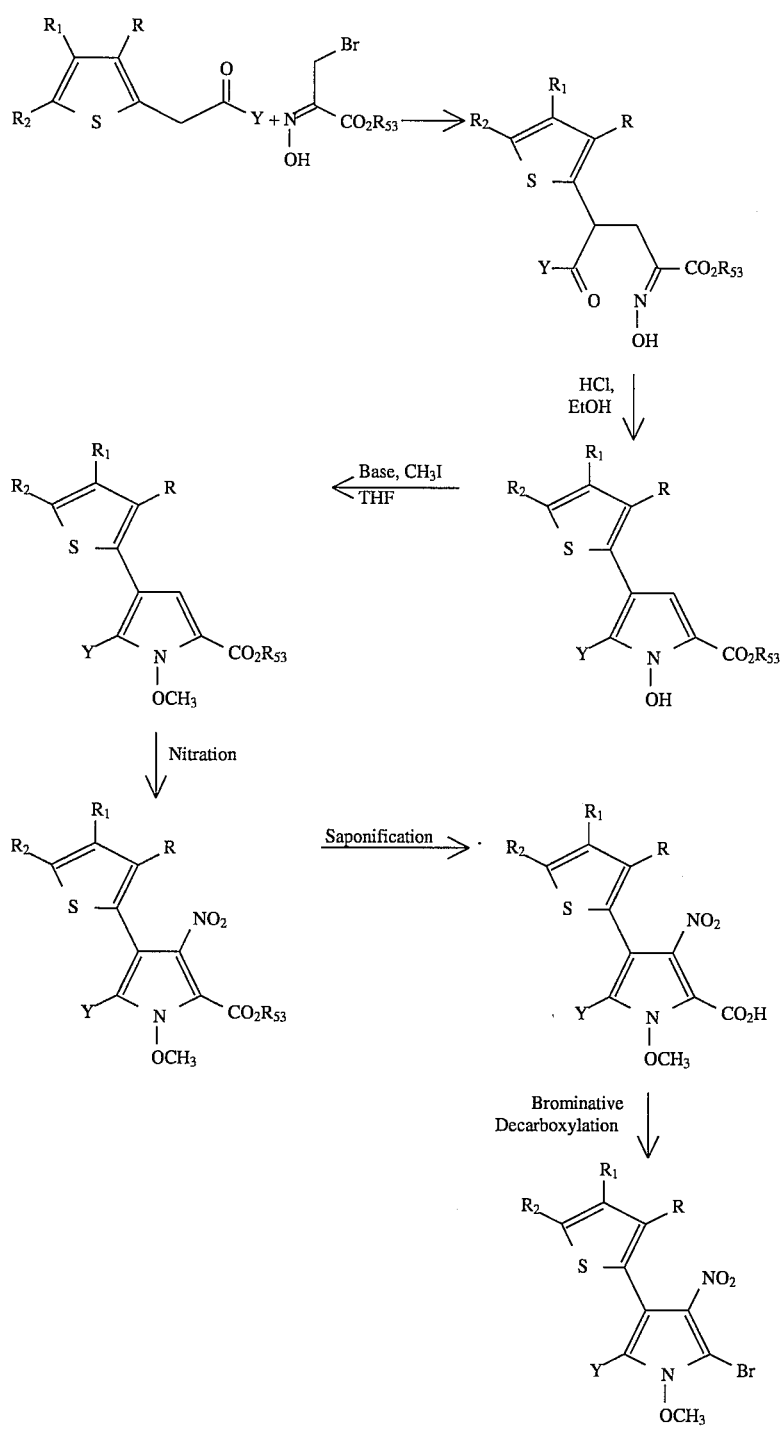
wherein Y is $C_1$–$C_6$ haloalkyl and R, $R_1$, $R_2$ and $R_{53}$ are as described in Flow Diagram XI.
Similarly, 2-bromo-3-nitro-5-($C_1$–$C_6$ haloalkyl)- 4-(3-thienyl)-1-methoxypyrrole compounds may be prepared as shown in Flow Diagram XVIII.

FLOW DIAGRAM XVIII
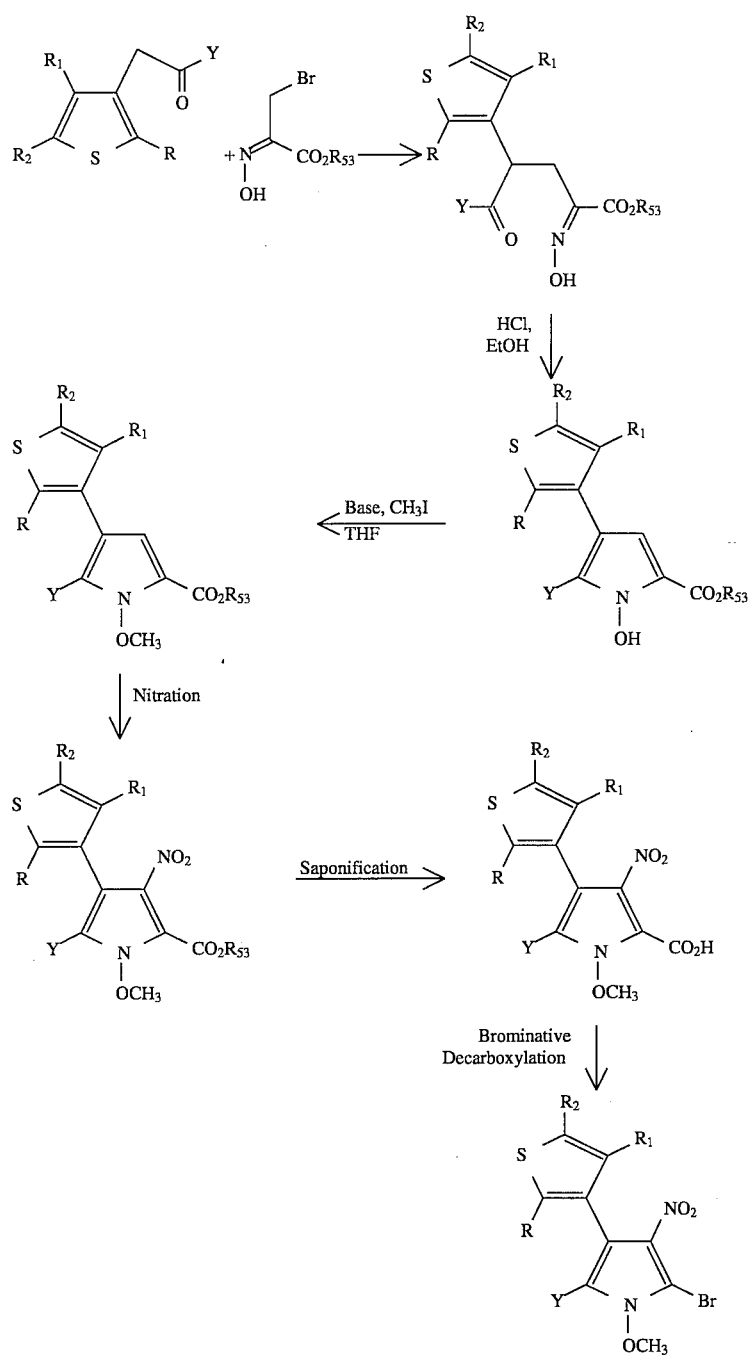
wherein Y is $C_1$–$C_6$ haloalkyl and R, $R_1$, $R_2$ and $R_{53}$ are as described in Flow Diagram XII.
3-Bromo-5-($C_1$–$C_6$ haloalkyl)-4-(2-thienyl)-1-methoxy-pyrrole- 2-carbonitrile compounds may be prepared as shown in Flow Diagram XIX.

FLOW DIAGRAM XIX
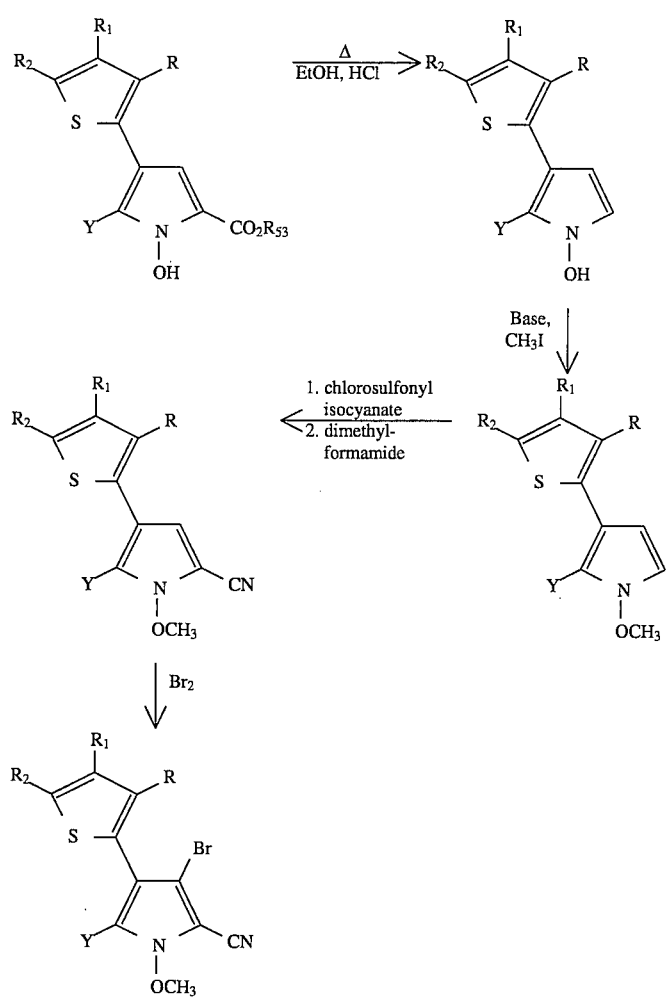
wherein Y is $C_1$–$C_6$ haloalkyl and R, $R_1$, $R_2$ and $R_{53}$ are as described in Flow Diagram XI.
Similarly, 3-bromo-5-($C_1$–$C_6$ haloalkyl)-4-(3-thienyl)-1-methoxypyrrole-2-carbonitrile compounds may be prepared as shown in Flow Diagram XX.
FLOW DIAGRAM XX
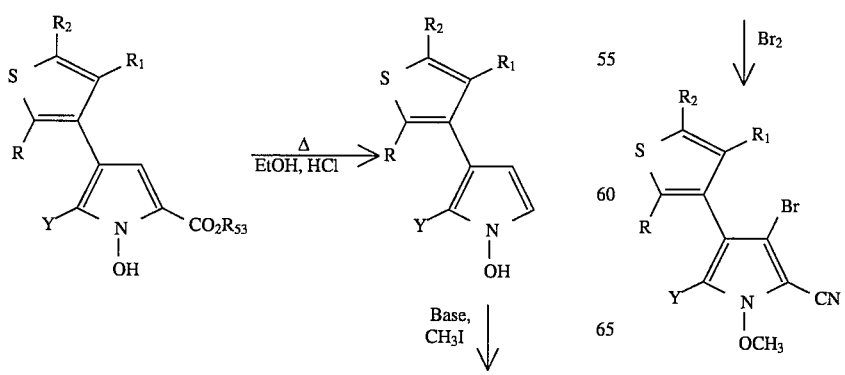
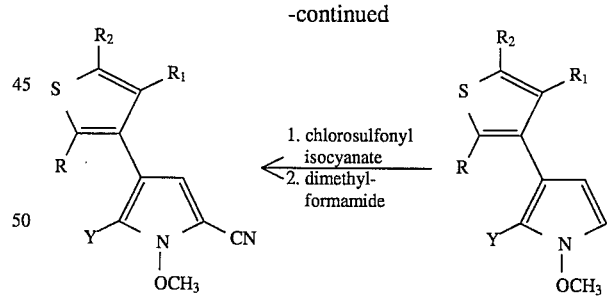

wherein Y is $C_1$–$C_6$ haloalkyl and R, $R_1$, $R_2$ and $R_{53}$ are as described in Flow Diagram XII.

4-Aryl-3-(nitro and cyano)-5-($C_1$–$C_6$ haloalkyl)- 2-(2- and 3-thienyl and -furyl)pyrrole compounds may be prepared by reacting a substituted or unsubstituted beta-(nitro or cyano)styrene of formula XXVI with bromine to form a (substituted or unsubstituted-phenyl)- 1,2-dibromo-2-(nitro or cyano)ethane of formula XXVII which is then subjected to a dehalogenation treatment using a base such as pyridine to form a substituted or unsubstituted (nitro or cyano)bromostyrene of formula XXVIII. Reaction of the bromostryrene with a formula XXIX oxazolinone in the presence of a tri($C_1$–$C_4$ alkyl)amine gives the desired 4-aryl-3-(nitro or cyano)-5-($C_1$–$C_6$ haloalkyl)-2-(2- or 3-thienyl or -furyl)pyrrole. The above reaction scheme is shown in Flow Diagram XXI.

FLOW DIAGRAM XXI

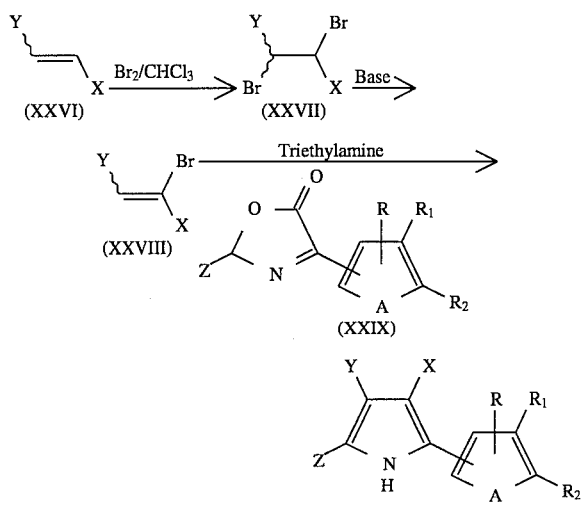

wherein
X is CN or $NO_2$;
Y is phenyl optionally substituted with one or more halogen atoms,
  $NO_2$ groups,
  CN groups,
  $C_1$–$C_4$ alkyl groups optionally substituted with one or more halogen atoms, or
  $C_1$–$C_4$ alkoxy groups optionally substituted with one or more halogen atoms;
Z is $C_1$–$C_6$ haloalkyl;
A is O or S;
R, $R_1$ and $R_2$ are each independently hydrogen, halogen or $NO_2$, and when $R_1$ and $R_2$ are taken together with the carbon atoms to which they are attached, they may form a ring in which $R_1R_2$ is represented by the structure:

L, T, V and W are each independently hydrogen, halogen, CN or $NO_2$.

Similarly, 4-(2-thienyl and -furyl)-3-(nitro and cyano)-5-($C_1$–$C_6$ haloalkyl)-2-arylpyrrole compounds may be prepared as shown in Flow Diagram XXII and 4-(3-thienyl and -furyl)-3-(nitro and cyano)-5-($C_1$–$C_6$ haloalkyl)-2-arylpyrrole compounds may be prepared as shown in Flow Diagram XXIII.

FLOW DIAGRAM XXII

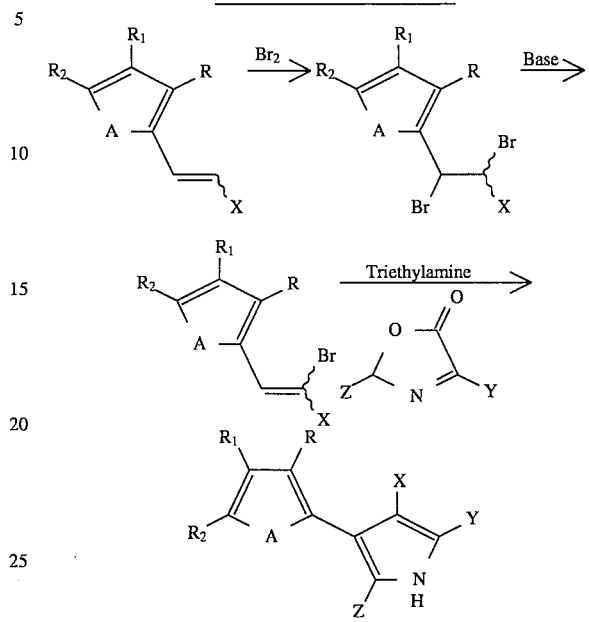

wherein A, X, Y and Z are as described in Flow Diagram XXI and R, $R_1$ and $R_2$ are as described in Flow Diagram XI.

FLOW DIAGRAM XXIII

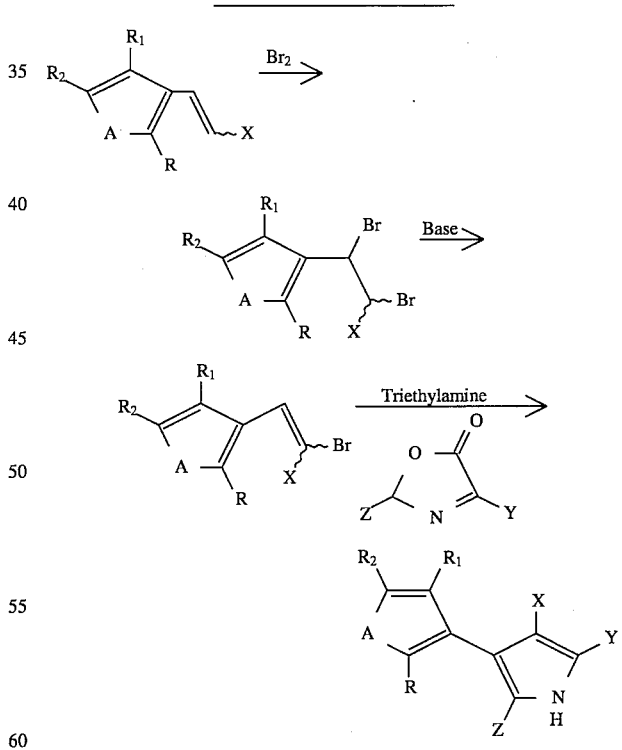

wherein A, X, Y and Z are as described in Flow Diagram XXI and R, $R_1$ and $R_2$ are as described in Flow Diagram XII.

3-Aryl-2-($C_1$–$C_6$ haloalkyl)-5-(2- and 3-thienyl and -furyl)pyrrole compounds may be prepared as shown in Flow Diagram XXIV.

FLOW DIAGRAM XXIV

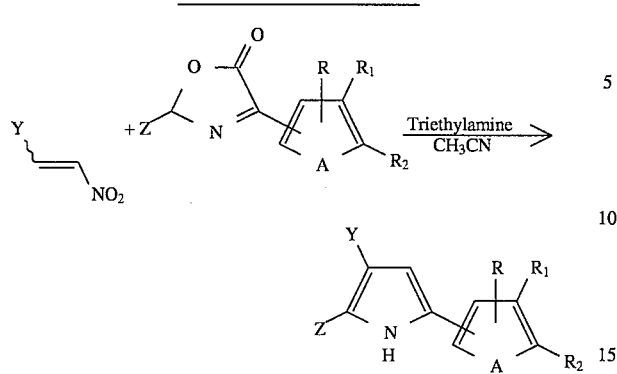

wherein Y, Z, A, R, $R_1$ and $R_2$ are as described in Flow Diagram XXI.

Similarly, 3-(2- and 3-thienyl and -furyl)- 2-($C_1$–$C_6$ haloalkyl)-5-arylpyrrole compounds may be prepared as shown in Flow Diagram XXV.

FLOW DIAGRAM XXV

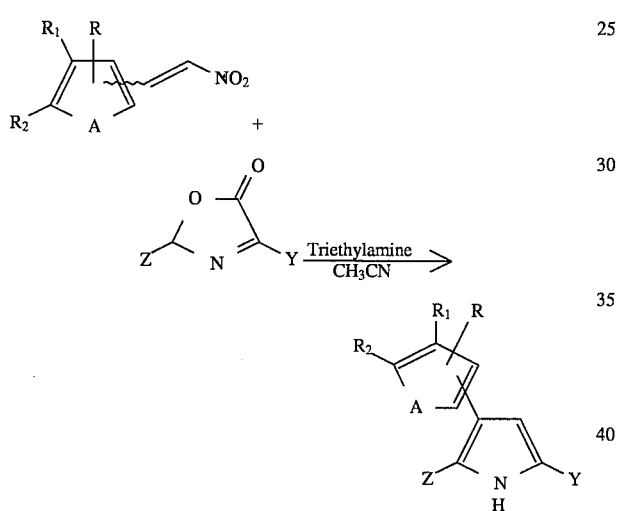

wherein Y, Z, A, R, $R_1$ and $R_2$ are as described in Flow Diagram XXI.

5-($C_1$–$C_6$ Haloalkyl)-3-aryl-2-(2- and 3-thienyl and -furyl)pyrrole compounds may be prepared by reacting a substituted or unsubstituted acetophenone of formula XXX with a thionyl halide in the presence of an organic base such as pyridine. Thereafter, the reaction mixture is treated with aqueous sodium tetrafluoroborate to give a formula XXXI N-α-(substituted or unsubstituted)styrylpyridinium tetrafluoroborate. The formula XXXI styrylpyridinium tetrafluoroborate is then reacted with a formula XXIX oxazolinone in the presence of a base, such as pyridine to form the desired 5-($C_1$–$C_6$ haloalkyl)-3-aryl-2-(2- or 3-thienyl or -furyl)pyrrole compound. The above reaction scheme is shown in Flow Diagram XXVI.

FLOW DIAGRAM XXVI

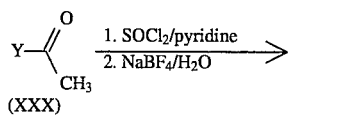

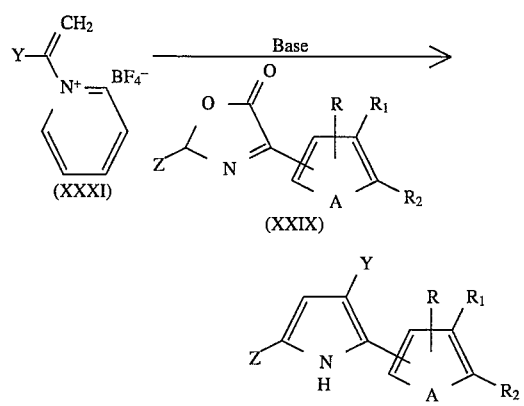

wherein Y, Z, A, R, $R_1$ and $R_2$ are as described in Flow Diagram XXI.

Similarly, 5-($C_1$–$C_6$ haloalkyl)-2-aryl-3-(2-thienyl and -furyl)pyrrole compounds may be prepared as shown in Flow Diagram XXVII and 5-($C_1$–$C_6$ haloalkyl)-2-aryl- 3-(3-thienyl and -furyl)pyrrole compounds may be prepared as shown in Flow Diagram XXVIII.

FLOW DIAGRAM XXVII

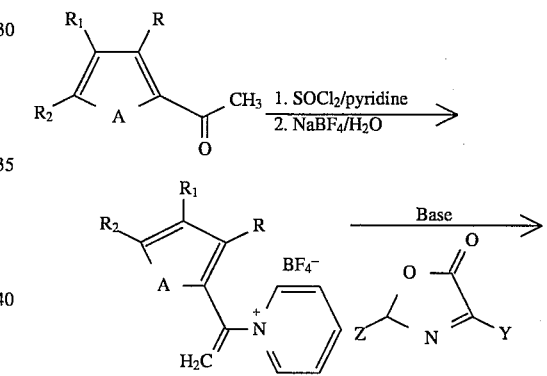

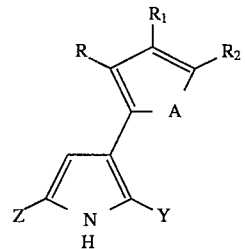

wherein A, Z and Y are as described in Flow Diagram XXI and R, $R_1$ and $R_2$ are as described in Flow Diagram XI.

FLOW DIAGRAM XXVIII

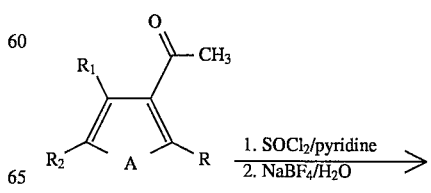

-continued
FLOW DIAGRAM XXVIII

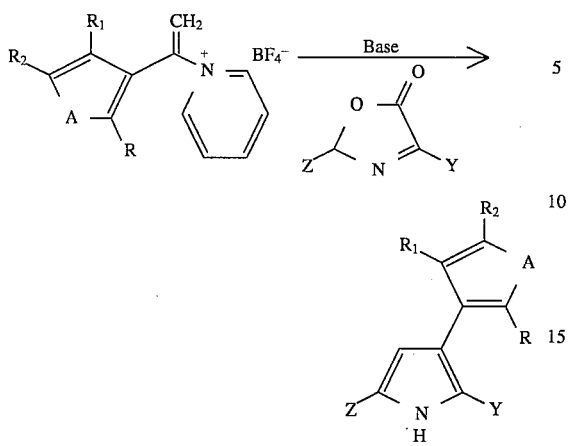

wherein A, Z and Y are as described in Flow Diagram XXI and R, $R_1$ and $R_2$ are as described in Flow Diagram XII.

5-($C_1$–$C_6$ haloalkyl)-2-aryl-4-nitro-3-(2-thienyl)pyrrole compounds may be prepared by reacting a 5-($C_1$–$C_6$ haloalkyl)-2-aryl-3-(2-thienyl)pyrrole compound with nitric acid and acetic anhydride as shown in Flow Diagram XXIX.

FLOW DIAGRAM XXIX

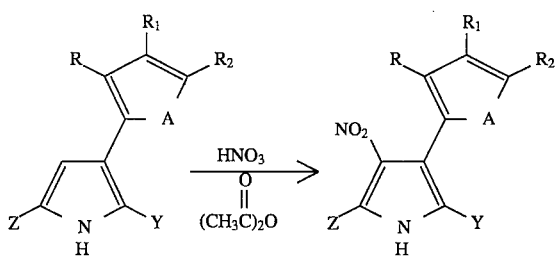

wherein A, Z and Y are as described in Flow Diagram XXI and R, $R_1$ and $R_2$ are as described in Flow Diagram XI.

Similarly, 5-($C_1$–$C_6$ haloalkyl)-2-aryl-4-nitro-3-(3-thienyl)pyrrole compounds may be prepared as shown in Flow Diagram XXX.

FLOW DIAGRAM XXX

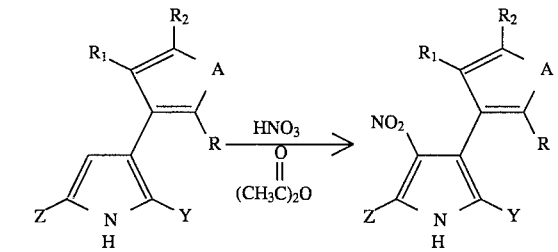

wherein A, Z and Y are as described in Flow Diagram XXI and R, $R_1$ and $R_2$ are as described in Flow Diagram XII.

2,3,5-Tris(trifluoromethyl)-4-(2- and 3-thienyl)pyrrole compounds of the present invention may be prepared by reacting a formula XXX 3-(2- or 3-thienyl)-1,1,1-trifluoro-2-propanone with hydroxylamine hydrochloride to form a formula XXXI oxime. The formula XXXI oxime is then reacted in a pressure bottle with liquid hexafluoro-2-butyne in the presence of at least a ten mole percent amount of a base such as an alkali metal alkoxide in a solvent at an elevated temperature to form a formula XXXII 3-(2- or 3-thienyl)-5a-hydroxy-2,4-a,5b-tris(trifluoromethyl)-1-pyrroline. The formula XXXII pyrroline is then reacted with hydrochloric acid in an alcohol to form the desired 2,3,5-tris(trifluoromethyl)-4-(2- or 3-thienyl)pyrrole compound. The above reaction scheme is shown in Flow Diagram XXXI.

FLOW DIAGRAM XXXI

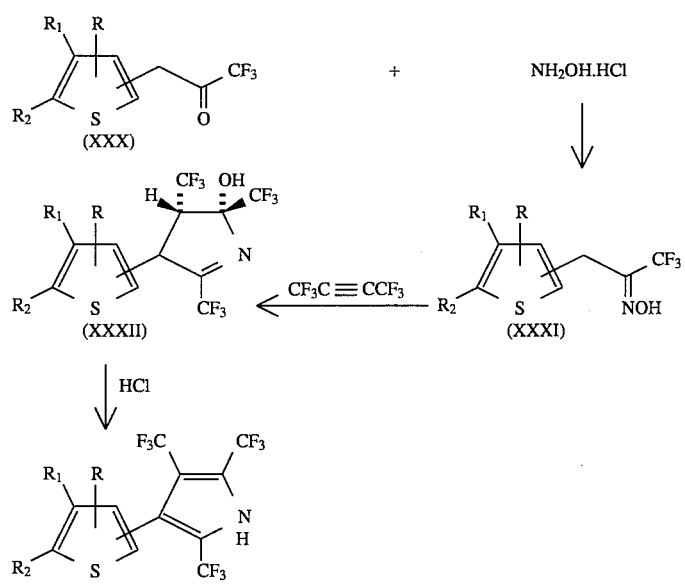

3,4-Bis(trifluoromethyl)-2-(2- and 3-thienyl and -furyl)pyrrole compounds may be prepared by reacting an N-(trimethylsilyl)methyl-5-methyl(thienyl- or furyl)thioimidate of formula VI with 2,3-dichlorohexafluorobutene as shown below in Flow Diagram XXXII.

FLOW DIAGRAM XXXII

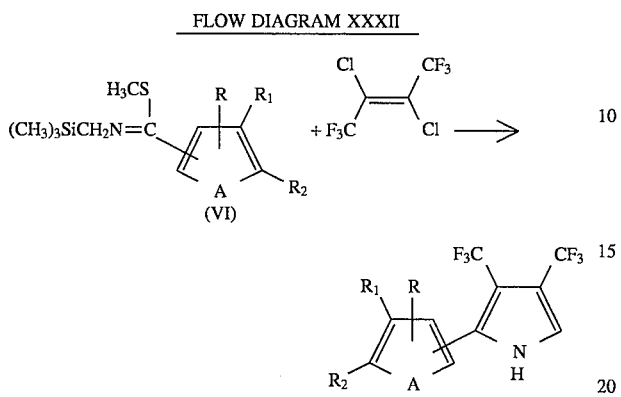

2,3-Bis(trifluoromethyl)-4-halo-5-(2-thienyl)pyrrole compounds may be prepared by reacting an oxime of formula XXXIII with hexafluoro-2-butyne in the presence of a base such as an alkali metal alkoxide to form the vinyl oxime of formula XXXIV and the 2-(2-thienyl)-4,5-trans-bis(trifluoromethyl)-1-pyrrolin- 5-ol of formula XXXV. The formula XXXIV vinyl oxime is then heated to form the formula XXXVI 2-(2-thienyl- 4,5-bis(trifluoromethyl)-1-pyrrolin-4-ol. The formula XXXV pyrrolin-5-ol or formula XXXVI pyrrolin- 4-ol is then reacted with hydrochloric acid in an alcohol to obtain a 5-(2-thienyl)-2,3-bis(trifluoromethyl)pyrrole compound. The 5-(2-thienyl)- 2,3-bis(trifluoromethyl)pyrrole is then reacted with a halogenating agent to obtain the desired 2,3-bis(trifluoromethyl)- 4-halo-5-(2-thienyl)pyrrole. The above reaction scheme is shown in Flow Diagram XXXIII.

FLOW DIAGRAM XXXIII

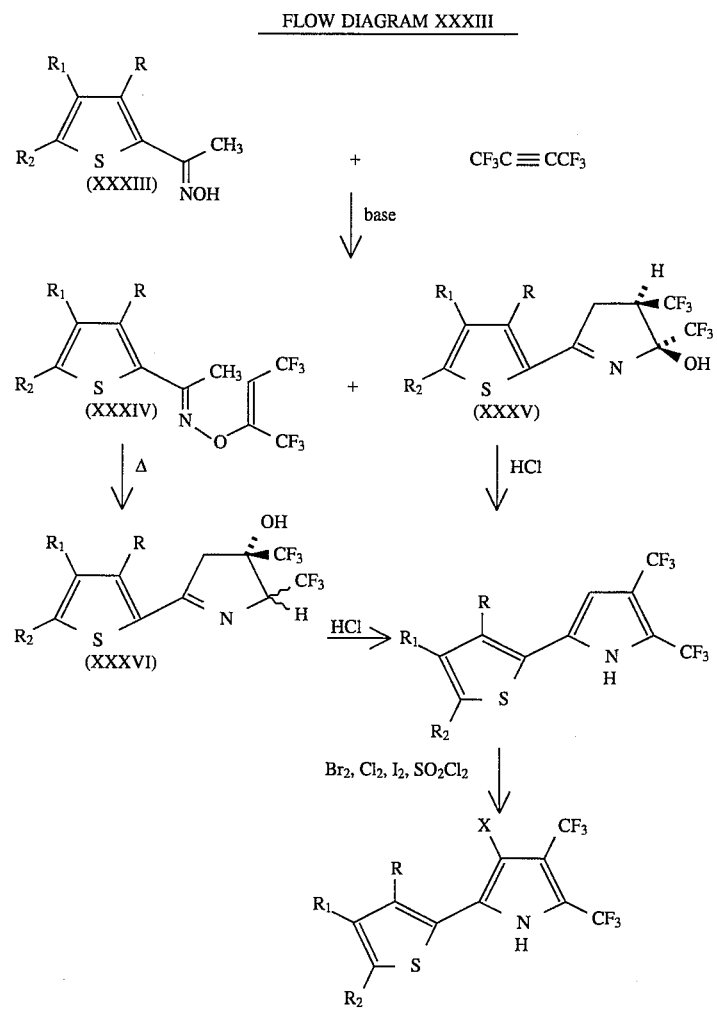

wherein X is Cl, Br or I and R, $R_1$ and $R_2$ are as described in Flow Diagram XI.

Similarly, 2,3-Bis(trifluoromethyl)-4-halo-5-(3-thienyl)pyrrole compounds may be prepared as shown in Flow Diagram XXXIV.

FLOW DIAGRAM XXXIV

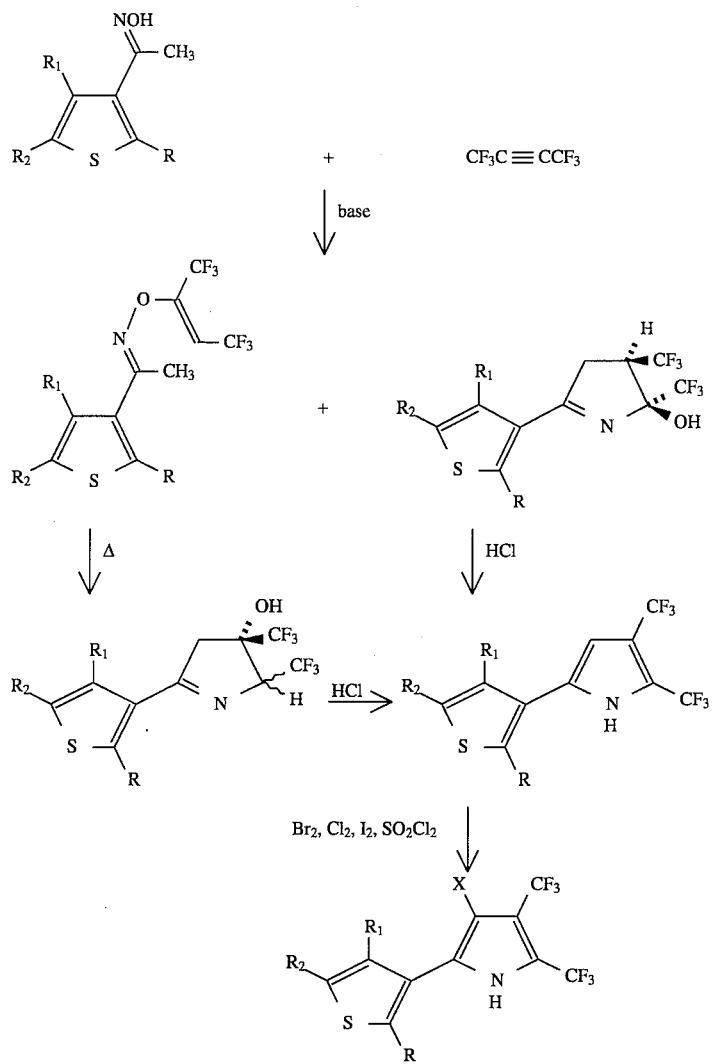

wherein X is Cl, Br or I and R, $R_1$ and $R_2$ are as described in Flow Diagram XII.

2,5-Bis(trifluoromethyl)-3-(2- and 3-thienyl)pyrrole compounds may be prepared as shown in Flow Diagram XXXV.

FLOW DIAGRAM XXXV

-continued
FLOW DIAGRAM XXXV

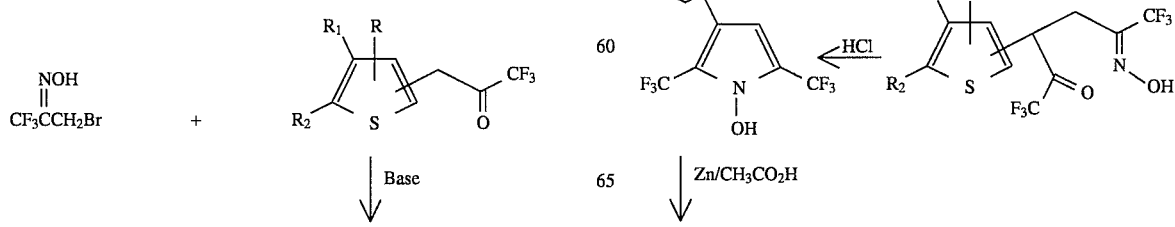

-continued
FLOW DIAGRAM XXXV

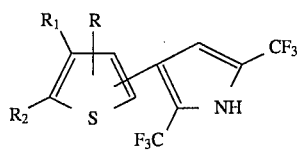

3-(Haloalkylsulfonyl)-2-(2- and 3-thienyl)pyrrole compounds may be prepared by reacting a (2- or 3-thienyl)ethynyl haloalkylsulfonyl compound of formula XXXVII with an aminoacetaldehyde di($C_1$-$C_4$ alkyl)acetal to form a {{α-[(haloalkylsulfonyl)methylene](2- or 3-thienyl)}amino}acetaldehyde di($C_1$-$C_4$ alkyl)acetal of formula XXXVIII. The formula XXXVIII acetal is then reacted with excess trifluoroacetic acid to obtain the desired 3-(haloalkylsulfonyl)-2-(2- or 3-thienyl)pyrrole compound. The above reaction scheme is shown in Flow Diagram XXXVI.

4-(Haloalkylsulfonyl)-5-(2-thienyl)pyrrole- 2-carbonitrile compounds may be prepared by reacting a 3-(haloalkylsulfonyl)-2-(2-thienyl)pyrrole compound of formula XXXIX with chlorosulfonyl isocyanate in the presence of a solvent to form a reaction mixture. The reaction mixture is then treated with dimethylformamide to obtain the desired 4-(haloalkylsulfonyl)-5-(2-thienyl)pyrrole- 2-carbonitrile compound. The above reaction scheme is shown in Flow Diagram XXXVIII.

FLOW DIAGRAM XXXVIII

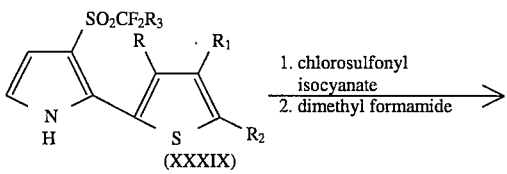

FLOW DIAGRAM XXXVI

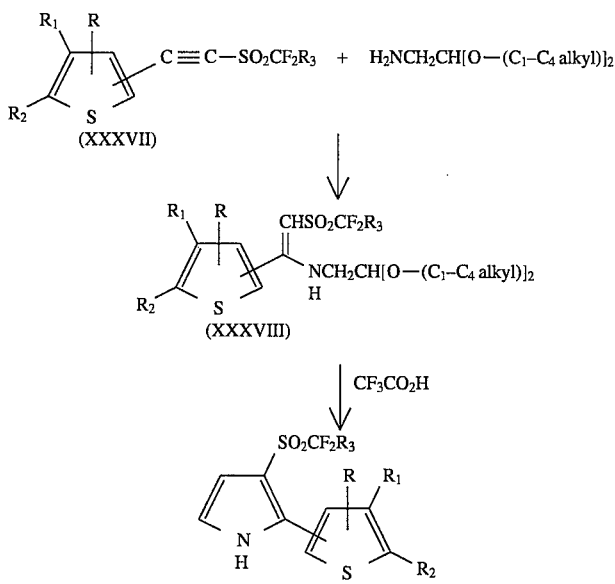

5-(Haloalkylthio)-2-(2- and 3-thienyl and -furyl)pyrrole compounds may be prepared by reacting a 2-(2- or 3-thienyl or -furyl)pyrrole compound with a haloalkylsulfenyl chloride compound in the presence of a base as shown in Flow Diagram XXXVII.

FLOW DIAGRAM XXXVII

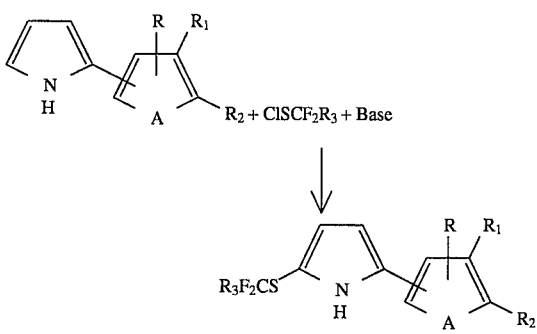

-continued
FLOW DIAGRAM XXXVIII

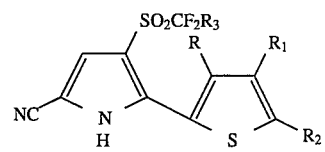

wherein $R_3$ is as described above for formula I and R, $R_1$ and $R_2$ are as described in Flow Diagram XI.

Similarly, 4-(haloalkylsulfonyl)-5-(3-thienyl)pyrrole-2-carbonitrile compounds may be prepared as shown in Flow Diagram XXXIX.

FLOW DIAGRAM XXXIX

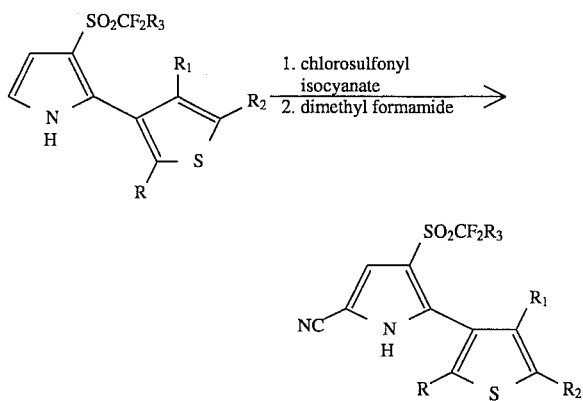

wherein $R_3$ is as described above for formula I and R, $R_1$ and $R_2$ are as described in Flow Diagram XII.

5-(Haloalkylsulfinyl)-2-(2- and 3-thienyl and -furyl)pyrrole compounds may be prepared by reacting a 5-(haloalkylthio)-2-(2- or 3-thienyl or -furyl)pyrrole compound with an oxidizing agent such as 3-chloroperoxybenzoic acid as shown in Flow Diagram XL.

FLOW DIAGRAM XL

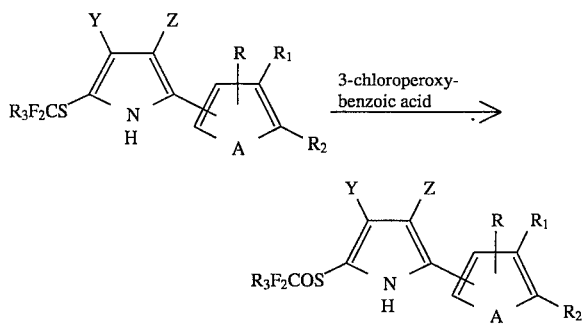

wherein A and $R_3$ are as described above for formula I; R, $R_1$ and $R_2$ are as described in Flow Diagram V and Y and Z are each independently hydrogen or halogen.

3-(2-And 3-thienyl and -furyl)-4-(haloalkylsulfonyl)pyrrole compounds may be prepared by reacting a haloalkylsulfone of formula XL with N-methylene- 1-(p-tolylsulfonyl)methylamine in the presence of a base such as sodium hydride as shown in Flow Diagram XLI.

FLOW DIAGRAM XLI

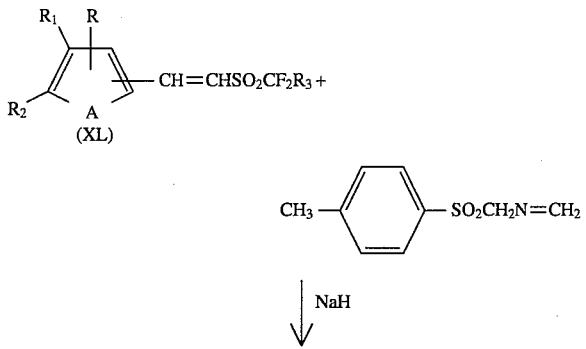

-continued
FLOW DIAGRAM XLI

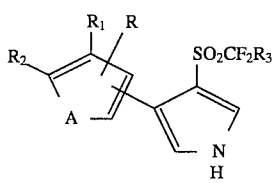

2-(Thienyl and furyl)-3-nitro-5-(haloalkylthio)pyrrole compounds and 5-(thienyl and furyl)- 3-nitro-2-(haloalkylthio)pyrrole compounds may be prepared by reacting a 2-(thienyl or furyl)-5-(haloalkylthio)pyrrole compound with fuming nitric acid in the presence of acetic anhydride as shown in Flow Diagram XLII.

FLOW DIAGRAM XLII

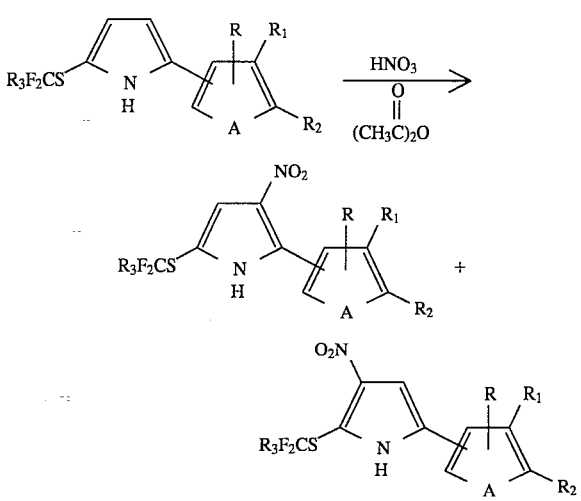

wherein A and $R_3$ are as described above for formula I and R, $R_1$ and $R_2$ are halogen.

Similarly, 2-(2-thienyl)-5-nitro-3-(haloalkylsulfonyl)pyrrole compounds and 2-(3-thienyl)-5-nitro- 3-(haloalkylsulfonyl)pyrrole compounds may be prepared as shown in Flow Diagrams XLIII and XLIV, respectively.

FLOW DIAGRAM XLIII

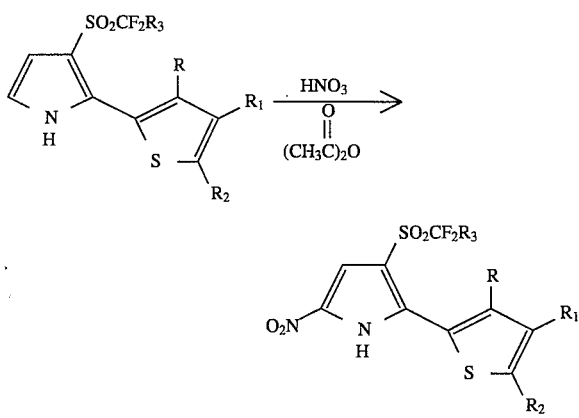

wherein A and $R_3$ are as described above for formula I and R, $R_1$ and $R_2$ are as described in Flow Diagram XI.

FLOW DIAGRAM XLIV

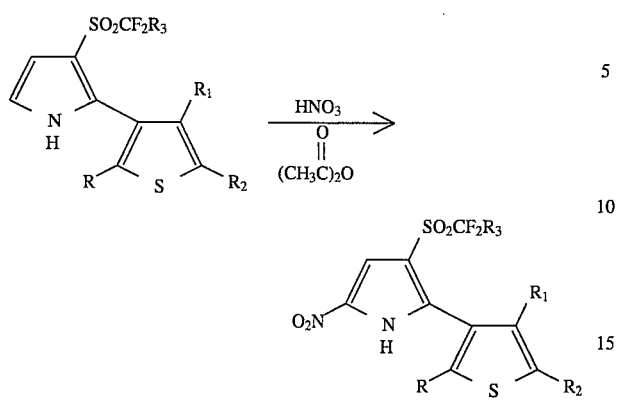

wherein A and $R_3$ are as described above for formula I and R, $R_1$ and $R_2$ are as described in Flow Diagram XII.

Methods for preparing 2-(2-thienyl)-3-(haloalkylthio)pyrrole compounds and 2-(3-thienyl)-3-(haloalkylthio)pyrrole compounds are shown in Flow Diagrams XLV and XLVI, respectively.

FLOW DIAGRAM XLV

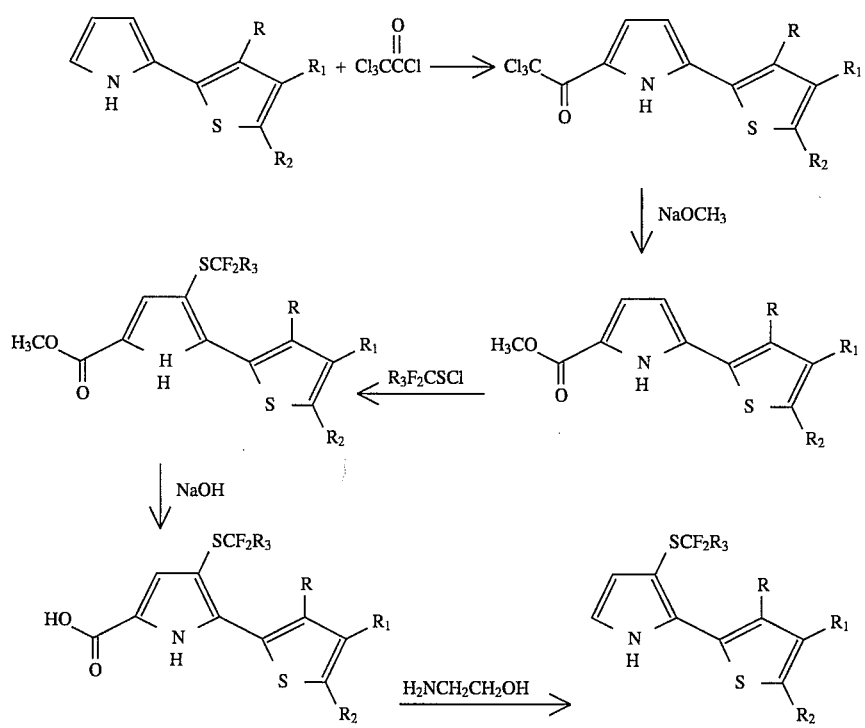

wherein R, $R_1$ and $R_2$ are as described in Flow Diagram XI.

FLOW DIAGRAM XLVI
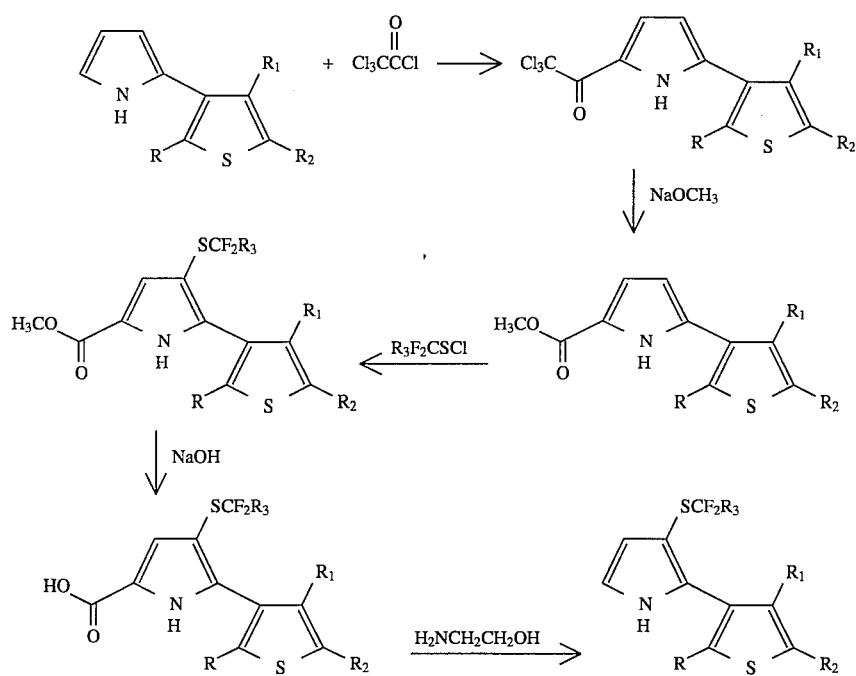
wherein R, $R_1$ and $R_2$ are as described in Flow Diagram XII.
3-Bromo-5-(thienyl or furyl)-2-(haloalkylsulfinyl and -sulfonyl-4-(haloalkylsulfonyl)pyrrole compounds may be prepared as shown in Flow Diagrams XLVII and XLVIII.
FLOW DIAGRAM XLVII
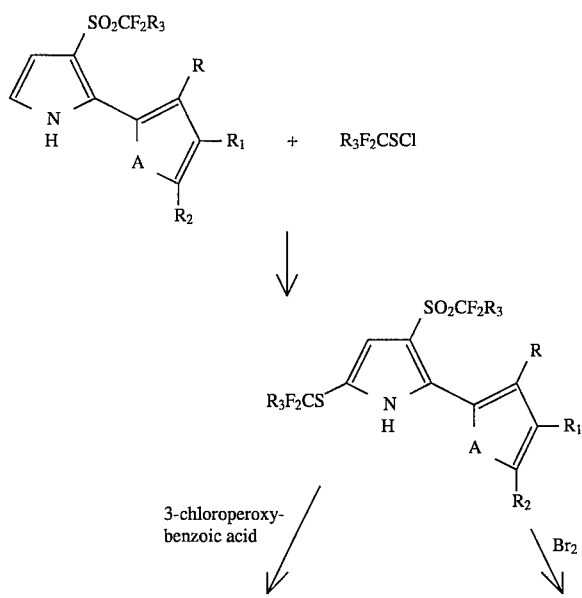

-continued
FLOW DIAGRAM XLVII
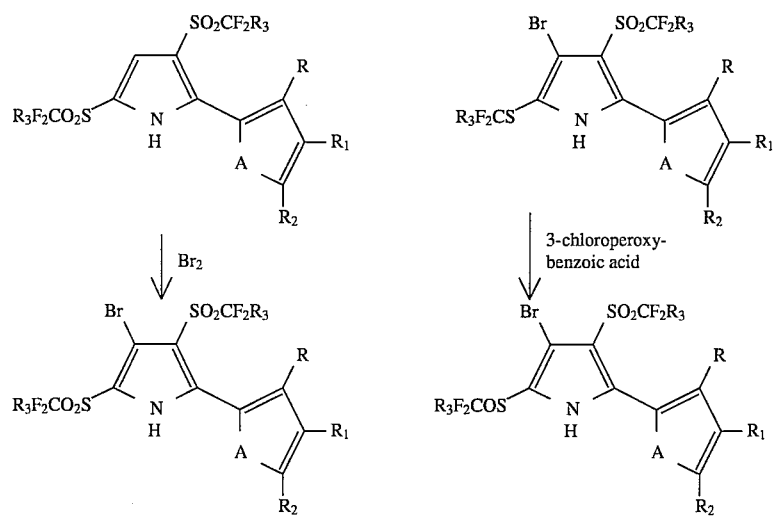
wherein A and $R_3$ are as described above for formula I and R, $R_1$ and $R_2$ are as described in Flow Diagram XI.
wherein A and $R_3$ are as described above for formula I and R, $R_1$ and $R_2$ are as described in Flow Diagram XII.
FLOW DIAGRAM XLVIII
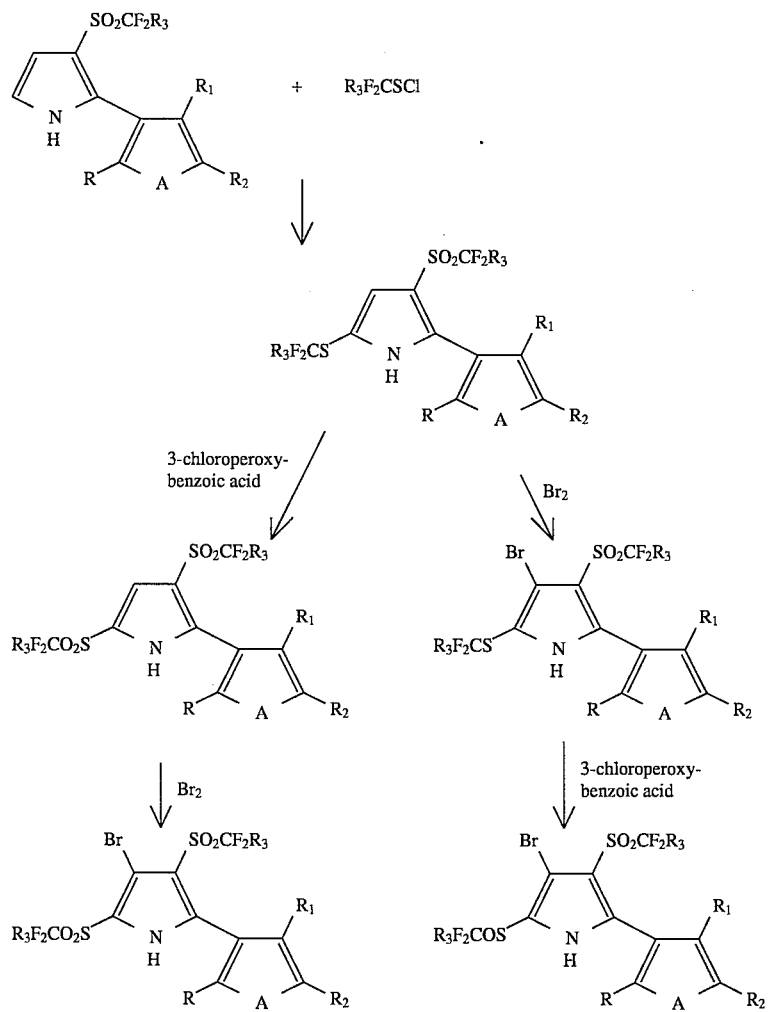

2-(Thienyl and furyl)-4-aryl-5-haloalkyl-3-(haloalkylsulfonyl)pyrrole compounds may be prepared as shown in Flow Diagram XLIX.

FLOW DIAGRAM XLIX

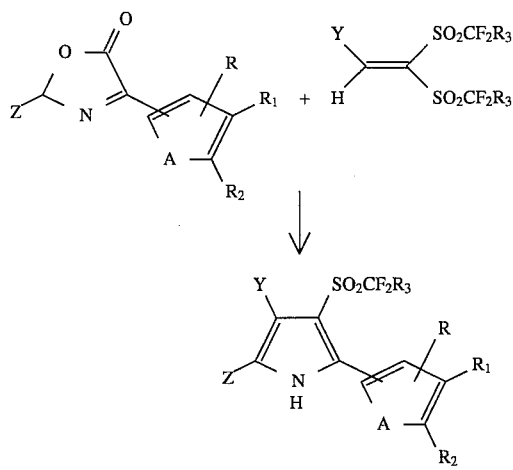

wherein A, R, $R_1$, $R_2$, Y and Z are as described in Flow Diagram XXI and $R_3$ is as described above for formula I.

Similarly, 2-aryl-4-(thienyl and furyl)-5-haloalkyl- 3-(haloalkylsulfonyl)pyrrole compounds may be prepared as shown in Flow Diagram L.

FLOW DIAGRAM L

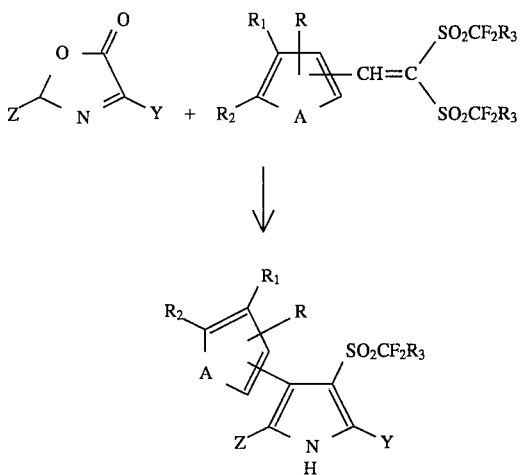

wherein A, R, $R_1$, $R_2$, Y and Z are as described in Flow Diagram XXI and $R_3$ is as described above for formula I.

2-(Thienyl and furyl)-5-(haloalkylsulfonyl)pyrrole-3-carbonitrile compounds may be prepared as shown in Flow Diagram LI.

FLOW DIAGRAM LI

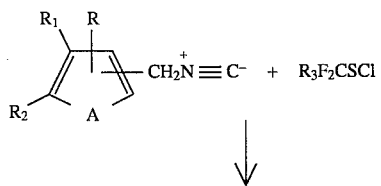

-continued
FLOW DIAGRAM LI

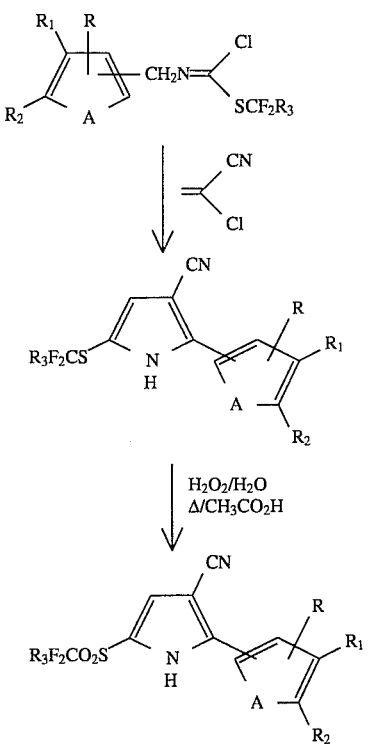

Conversion of formula I compounds wherein Y and/or Z are hydrogen to the corresponding formula I compounds wherein Y and/or Z are halogen is readily achieved by reaction of the formula I hydrogen substituted pyrrole with at least about 1 or 2 equivalents of a halogenating agent such as a sulfuryl halide, bromine or chlorine in the presence of a solvent such as dioxane, tetrahydrofuran, acetic acid or a chlorinated hydrocarbon solvent. In addition, formula I compounds wherein R, $R_1$ and/or $R_2$ are hydrogen may be converted to the corresponding formula I compounds wherein R, $R_1$ and/or $R_2$ are halogen by reaction of the formula I compound wherein R, $R_1$ and/or $R_2$ are hydrogen with a halogenating agent in the presence of a solvent. Halogenating agents that may be employed include bromine, sulfuryl chloride, sulfuryl bromide, sodium hypochlorite, t-butylhypochlorite, N-bromosuccinimide, N-iodosuccinimide and the like. Several halogenation reaction schemes are shown in Flow Diagram LII.

FLOW DIAGRAM LII

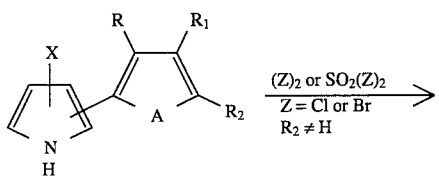

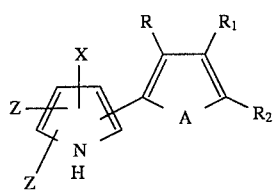

-continued
FLOW DIAGRAM LII

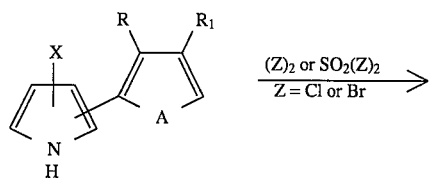

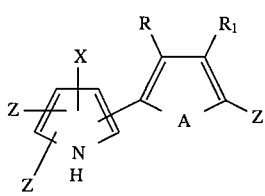

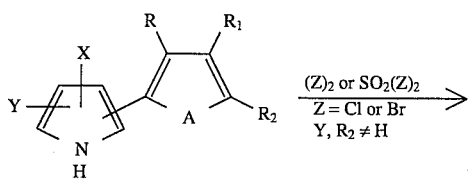

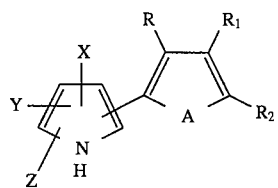

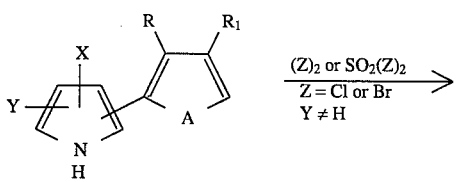

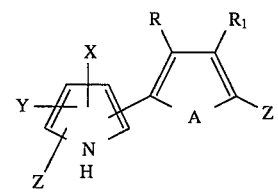

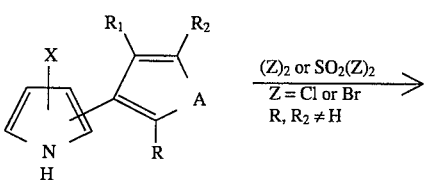

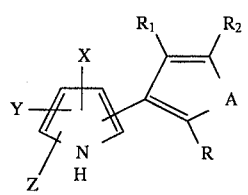

-continued
FLOW DIAGRAM LII

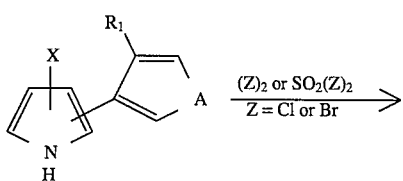

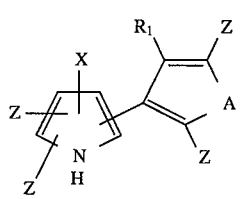

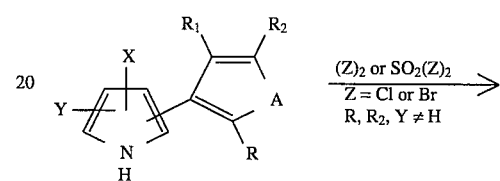

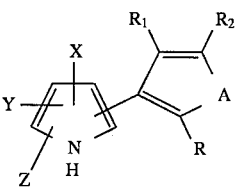

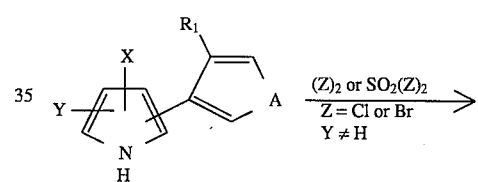

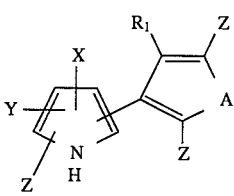

Preparation of 1-substituted formula I compounds can be achieved by reaction of the appropriately substituted formula I compound having D as hydrogen with an alkylating or acylating agent in the presence of an alkai metal alkoxide or hydride. For example, a formula I compound wherein D is hydrogen and R, $R_1$, $R_2$, A, X, Y and Z are as described for formula I above, is reacted with an appropriate alkylating agent such as a $C_1$–$C_6$ alkylhalide in which the alkyl group is straight or branched and is optionally substituted with from one to three halogen atoms, one hydroxy, one cyano, one $C_1$–$C_4$ alkoxy, one $C_1$–$C_4$ alkylthio, one phenyl group optionally substituted with from one to three halogen atoms, or one benzyloxy group optionally substituted with from one to three halogen atoms, and an alkali metal alkoxide such as sodium or potassium t-butoxide. This reaction provides a thienyl- or furylpyrrole having the same substituents as the starting material, but in addition is substituted on the nitrogen with a $C_1$–$C_6$ alkyl group optionally substituted as described above. This reaction scheme may be illustrated as follows:

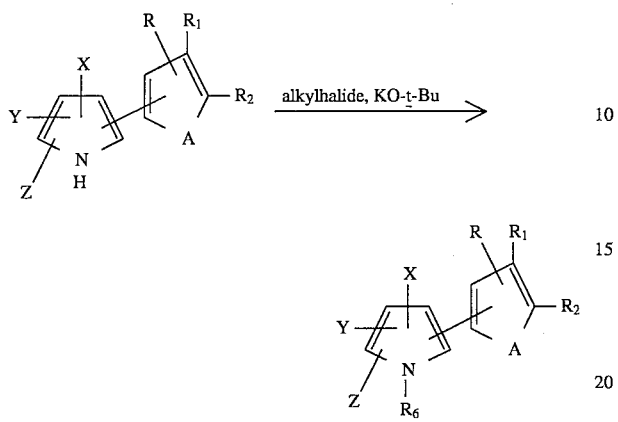

wherein R, $R_1$, $R_2$, A, X, Y and Z are as described for formula I above and $R_6$ is $C_1$–$C_6$ alkyl optionally substituted as described above. In a similar reaction cyanogen bromide is substituted for the alkylhalide and yields a formula I thienyl- or furylpyrrole having a carbonitrile, rather than an alkyl group on the 1-position.

Advantageously, the above-described alkylation procedure may also be applied to the preparation of formula I thienyl- and furylpyrroles having an N-$C_3$–$C_6$ alkenyl or N-$C_3$–$C_6$ alkynyl substituent. This substitution is obtained by simply substituting a $C_3$–$C_6$ alkenyl halide or $C_3$–$C_6$ alkynyl halide for the $C_1$–$C_6$ alkyl halide 25 in the above-described reaction.

In a similar manner, preparation of 1-acylated thienyl- and furylpyrroles may be achieved by the reaction of an appropriately substituted formula I thienyl- or furylpyrrole wherein D is hydrogen with an acylating agent in the presence of an alkali metal alkoxide. Acylating agents such as $C_1$–$C_6$ alkyl or $C_2$–$C_6$ alkenyl acid chlorides, substituted $C_1$–$C_6$ alkyl or $C_2$–$C_6$ alkenyl acid chlorides, benzoyl chloride, substituted benzoyl chlorides, phenylchloroformate, substituted phenylchloroformates, $C_1$–$C_6$ alkyl or $C_2$–$C_6$ alkenylchloroformates, substituted $C_1$–$C_6$ alkyl or $C_2$–$C_6$ alkenylchloroformates, N-substituted carbamoyl chlorides and the like may be employed. the reaction may be illustrated as follows:

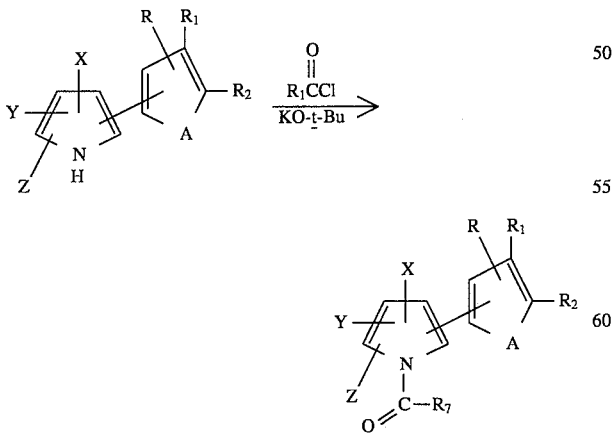

Formula I thienyl- and furylpyrroles wherein $R_6$ is $CH_2SQ$ may be prepared by reaction of the appropriately substituted formula I thienyl- or furylpyrrole having $R_6$ as chloromethyl with an alkali metal salt of an SQ compound in the presence of a base. And formula I thienyl- and furylpyrrole compounds wherein $R_6$ is $CHR_8NHC(O)R_9$ may be prepared a shown below.

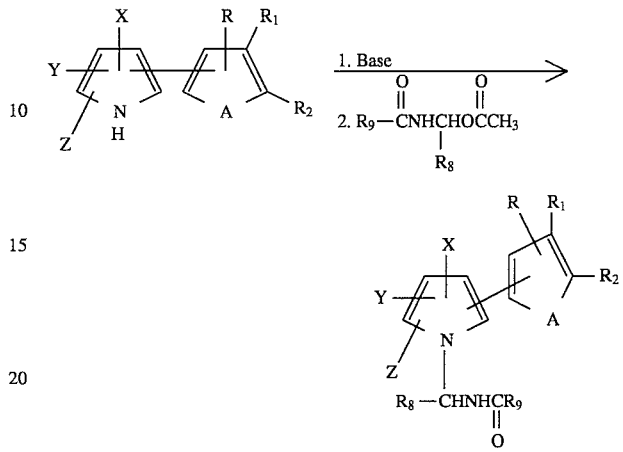

Advantageously, 1-halomethyl thienyl- and furylpyrroles may be prepared as shown below.

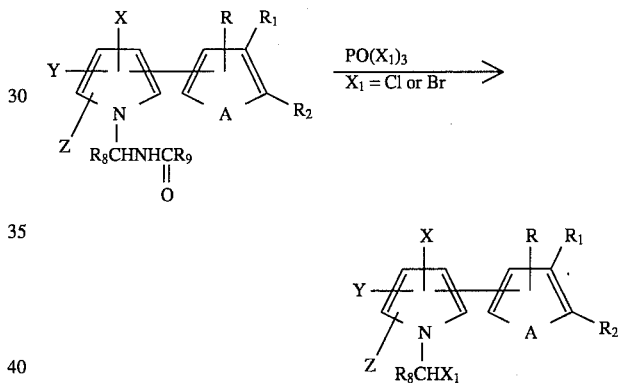

Formula I compounds wherein $R_6$ is $R_{10}CHOC(O)$-$(CR_{11}R_{12})_nQ_1$ may be prepared as shown below.

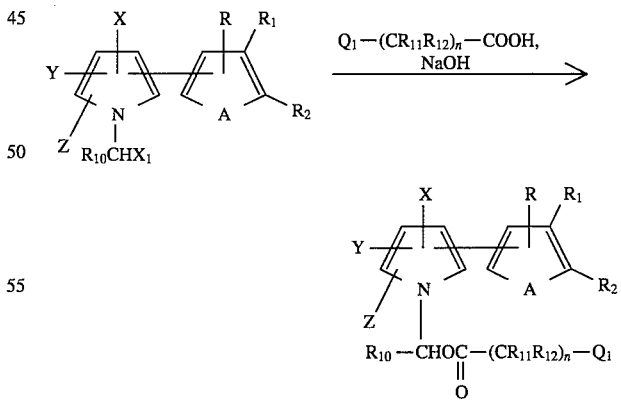

Formula I compounds wherein B is $OR_6$ may be prepared by reacting an appropriately substituted formula I thienyl- or furylpyrrole compound, wherein B is OH, and R, $R_1$, $R_2$, A, X, Y and Z are as described for formula I above, with an appropriate alkylating agent and a suitable base, for example, a chloromethyl $C_1$–$C_4$ alkyl ether and potassium t-butoxide. This reaction provides a thienyl- or furylpyrrole having the same substituents as the starting material, but in addition is substituted on the oxygen with $C_1$–$C_4$ alkoxymethyl. In a similar reaction bromoacetonitrile is substituted for the chloromethyl $C_1$–$C_4$ alkyl ether and gives a formula I thienyl- or furylpyrrole with an acetonitrile substituent on the oxygen. The reactions may be illustrated as follows:

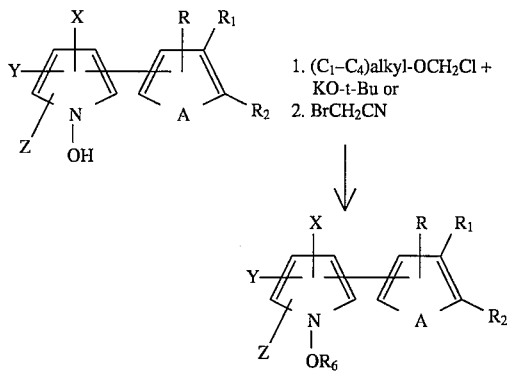

wherein R, $R_1$, $R_2$, A, X, Y and Z are as described for formula I above and $R_6$ is (1) $C_1$–$C_4$ alkoxymethyl or (2) $CH_2CN$.

Similarly, formula I compounds wherein B is $C(O)R_7$ may be prepared by reacting an appropriately substituted formula I thienyl- or furylpyrrole compound, wherein B is OH, and R, $R_1$, $R_2$, A, X, Y and Z are as described for formula I above, with an appropriate acylating agent and a suitable base, for example, a $C_1$–$C_6$ acid chloride and potassium t-butoxide. This reaction provides a thienyl- or furylpyrrole compound having the same substituents as the starting material, but in addition is substituted on the oxygen with $C_1$–$C_6$ alkanoyl. The reaction may be illustrated as follows:

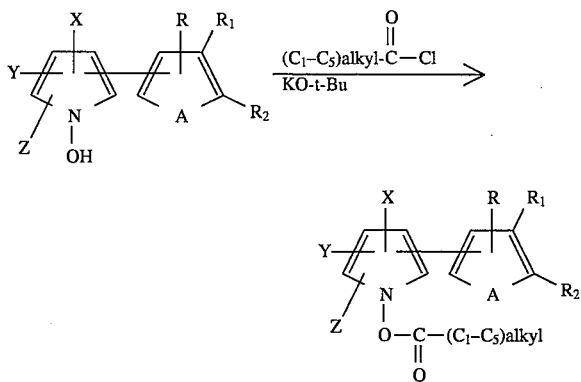

The thienyl- and furylpyrrole compounds of the present invention are effective for controlling insects and acarina. Those compounds are also effective for protecting growing or harvested crops from attack by insects and acarina.

Insects controlled by the formula I, compounds of this invention include Lepidoptera such as tobacco budworms, cabbage loopers, cotton boll worms, beet armyworms, southern armyworms and diamondback moths; Homoptera such as aphids, leaf hoppers, plant hoppers and white flies; Thysanoptera such as thrips;Coleoptera such as boll weevils, Colorado potato beetles, southern corn rootworms and mustard beetles;and Orthoptera such as locusts, crickets, grasshoppers and cockroaches. Acarina controlled by the compounds of this invention include mites such as two-spotted spider mites, carmine spider mites, banks grass mites, strawberry mites, citrus rust mites and leprosis mites. Advantageously, it has been found that the compounds of the present invention are especially effective against tobacco budworms and southern armyworms.

In practice generally about 10 ppm to about 10,000 ppm and preferably about 100 ppm to about 5,000 ppm of a formula I thienyl- or furylpyrrole compound, dispersed in water or another liquid carrier, is effective when applied to the plants, the crops or the soil in which said crops are growing to protect said crops from attack by insects and acarina.

The thienyl- and furylpyrrole compounds of this invention are also effective for controlling insects and acarina, when applied to the foliage of plants and/or to the soil or water in which said plants are growing in sufficient amount to provide a rate of from about 0.1 kg/ha to 4.0 kg/ha of active ingredient.

While the compounds of this invention are effective for controlling insects and acarina when employed alone, they may also be used in combination with other biological chemicals, including other insecticides and acaricides. For example, the formula I compounds of this invention may be used effectively in conjunction or combination with pyrethroids, phosphates, carbamates, cyclodienes, endotoxin of bacillus thuringiensis (Bt), formamidines, phenol tin compounds, chlorinated hydrocarbons, benzoylphenyl ureas and the like.

The compounds of this invention may be formulated as emulsifiable concetrates, flowable concentrates or wettable powders with are diluted with water or other suitable polar solvent, generally in situ, and then applied as a dilute spray. Said compounds may also be formulated in dry compacted granules, granular formulations, dusts, dust concentrates, suspension concentrates, microemulsions and the like all of which lend themselves to seed, soil, water and/or foilage applications to provide the requisite plant protection. Such formulations include the compounds of the invention admixed with inert, solid or liquid diluents.

For example , wettable powders, dusts and dust concentrate formulations can be prepared by grinding and blending together about 25% to about 85% by weight of a formula I compound and about 73% to about 13% by weight of a solid diluent such as bentonite, diatomaceous earth, kaolin, attapulgite, or the like, about 1% to 5% by weight of a dispersing agent such as sodium lignosulfonate and about 1% to 5% by weight of a nonionic surfactant, such as octylphenoxy polyethoxy ethanol, nonylphenoxy polyethoxy ethanol or the like.

A typical emulsifiable concentrate can be prepared by dissolving about 15% to about 70% by weight of a formula I compound in about 84% to about 29% by weight of a solvent such as isophorone, toluene, butyl cellosolve, methyl acetate, propylene glycol monomethyl ether or the like and dispersing therein about 1% to 5% by weight of a nonionic surfactant such as an alkylphenoxy polyethoxy alcohol.

In order to facilitate a further understanding of the invention, the following examples are presented primarily for the purpose of illustrating more specific details thereof. The examples generally utilize the above reation schemes and also provide further means for preparing even more compounds of the present invention which are not specifically described above. The invention should not be deemed limited by the examples as the full scope of the invention is defined in the claims.

EXAMPLE 1

Preparation of 3,4,5-Trichloro-2-thiophenecarboxaldehyde

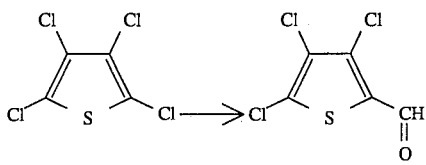

Butyllithium (2.5 molar in tetrahydrofuran, 3.96 mL, 9.9 mmol) is added to a solution of tetrachlorothiophene (2.00 g, 9.01 mmol) in tetrahydrofuran at 0° C. The reaction mixture is stirred at 0° C. for 30 minutes, warmed to room temperature over 45 minutes, treated with N,N-dimethylformamide (0.79 g, 10.8 mmol), stirred for three hours, poured into one molar hydrochloric acid at 4° C. and extracted with ether. The combined organic extracts are washed sequentially with water and brine, dried over MgSO₄ and concentrated in vacuo to obtain a brown solid. Flash chromatography of the solid using silica gel and a 5% ethyl acetate in hexane solution gives a beige solid which is recrystallized from ethyl acetate and hexane to obtain the title product as beige needles (1.63 g, 84%, mp 81°–82° C.).

EXAMPLE 2

Preparation of the Oxime of 3,4,5-trichloro-2-thiophenecarboxaldehyde

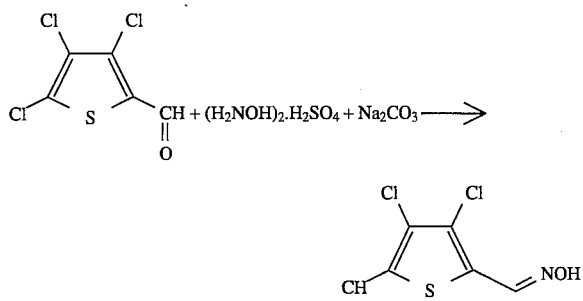

A solution of sodium carbonate (10.91 g, 99.2 mmol) in water is added to a slurry of 3,4,5-trichloro-2-thiophenecarboxaldehyde (10.69 g, 49.6 mmol) and hydroxylamine sulfate (8.14 g, 49.6 mmol) in water. After stirring at room temperature for 18 hours, the solids are filtered out of the reaction mixture and dried under high vacuum overnight to give the title product as a white solid (10.24 g, 92%).

Using essentially the same procedure, and employing the appropriately substituted thiophenecarboxaldehyde, the following compounds are obtained.

| R | R₁ | R₂ |
|---|----|----|

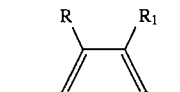

| R | R₁ | R₂ |
|---|----|----|
| H | H | Cl |
| H | Br | H |
| H | —CH=CH—CH=CH— | |

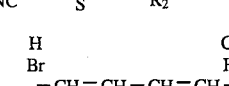

| H | H | H |

EXAMPLE 3

Preparation of 3,4,5-Trichloro-2-thiophenecarbonitrile

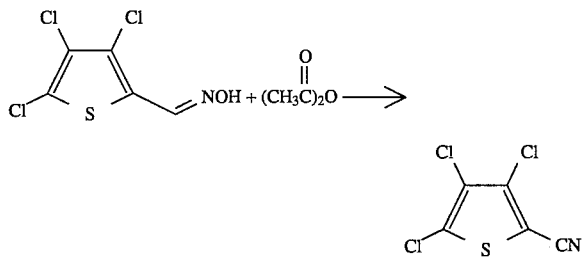

A solution of the oxime of 3,4,5-trichloro-2-thiophenecarboxaldehyde (10.075 g, 43.7 mmol) in acetic anhydride is refluxed for two hours and concentrated in vacuo to obtain a brown oil. The oil is diluted with ether and the organic solution is washed sequentially with water and brine, dried over MgSO₄ and concentrated in vacuo to give a brown oil. Flash chromatography of the oil using silica gel and a 5% ethyl acetate in hexane solution gives a beige solid which is recrystallized from ethyl acetate and hexane to obtain the title product as beige needles (8.23 g, 89%, mp 63°–64° C.).

Using essentially the same procedure, and employing the appropriately substituted oxime, the following compounds are obtained:

| R | R₁ | R₂ |
|---|----|----|

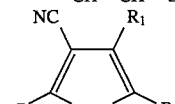

| H | H | Cl |
| H | Br | H |
| H | —CH=CH—CH=CH— | |

| H | H | H |

EXAMPLE 4

Preparation of 2-(3,4,5-Trichloro-2-thienyl)-5-(trifluoromethyl) pyrrole-3-carbonitrile

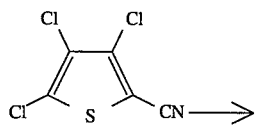

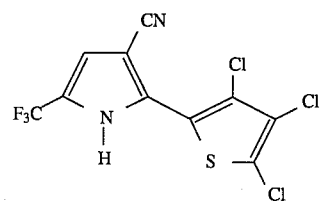

Acetonitrile (0.97 g, 23.7 mmol) is added dropwise to a solution of lithium diisopropylamide (two molar in hydrocarbons, 10.9 mL, 21.8 mmol) in tetrahydrofuran at −78° C. The reaction mixture is stirred at −78° C. for 30 minutes, treated with a solution of 3,4,5-trichloro-2-thiophenecarbonitrile (3.87 g, 18.2 mmol) in tetrahydrofuran, stirred for 30 minutes at −78° C., warmed to room temperature over 45 minutes, quenched with saturated ammonium chloride solution and extracted with ether. The combined organic extracts are washed sequentially with water and brine, dried over MgSO₄ and concentrated in vacuo to obtain a red solid. A mixture of the red solid and 1-bromo-3,3,3-trifluoroacetone (1.95 mL, 18.7 mmol) in acetic acid is refluxed for three hours and 30 minutes, diluted with water and extracted with ether. The combined organic extracts are washed sequentially with water and brine, dried over MgSO₄ and concentrated .in vacuo to obtain a red solid. Flash chromatography of the solid using silica gel and a 15% ethyl acetate in hexane solution gives the title product as a white solid (0.49 g, 7.8%, mp 220°–221° C.).

Using essentially the same procedure, and employing the appropriately substituted cyanofuran or cyanothiophene, the following compounds are obtained:

| A | R | $R_1$ | $R_2$ | mp °C. |
|---|---|---|---|---|
| S | H | H | H | 210 |
| S | H | H | Br | 230–231 |
| S | H | H | Cl | 232–233 |
| S | H | Br | H | >230 |
| O | H | H | H | 196–197 |
| S | H | —CH=CH—CH=CH— | | >230 |
| S | Cl | —CH=CH—CH=CH— | | 193–195 |

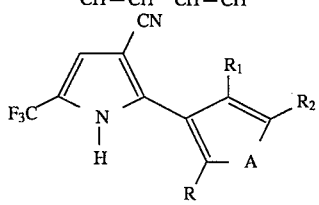

| A | R | $R_1$ | $R_2$ | mp °C. |
|---|---|---|---|---|
| S | H | H | H | 229–231 |

EXAMPLE 5

Preparation of 4-Bromo-2-(3,4,5-trichloro-2-thienyl)-5-(trifluoromethyl)pyrrole-3-carbonitrile

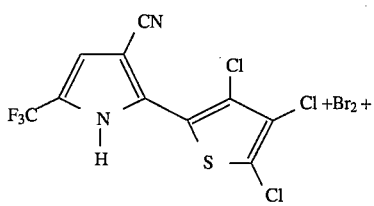

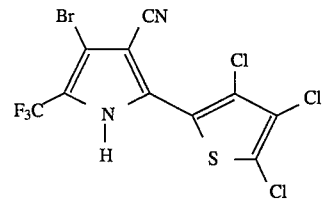

Bromine (0.208 g, 1.31 mmol) is added to a solution of 2-(3,4-5-trichloro-2-thienyl)-5-(trifluoromethyl)pyrrole-3-carbonitrile (0.38 g, 1.09 mmol) and sodium acetate (0.11 g, 1.31 mmol) in acetic acid at 0° C. After stirring at 50° C. for 30 minutes, additional sodium acetate (0.11 g, 1.31 mmol) and bromine (0.208 g, 1.31 mmol) are added to the reation mixture. The reaction mixture is stirred for 15 minutes, cooled to room temperature and poured into a 1% sodium bisulfite solution. The solids are filtered out of the aqueous mixture and dried overnight under high vacuum to give a white solid. The solid is recrystallized from ethyl acetate and hexane to obtain the title product as white crystals (0.45 g, 96%, mp 221°–224° C.).

Using essentially the same procedure, and employing the appropriately substituted 2-(thienyl or furyl)-5-(trifluoromethyl)pyrrole-3-carbonitrile, the following compounds are obtained:

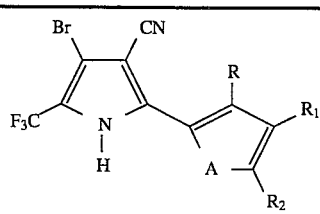

| A | R | $R_1$ | $R_2$ | mp °C. |
|---|---|---|---|---|
| S | H | H | Br | 254 (dec.) |
| S | H | H | Cl | >230 |
| S | H | Br | Br | >230 |
| O | H | H | Br | >230 |
| S | Br | —CH=CH—CH=CH— | | 201–203 |
| S | Cl | —CH=CH—CH=CH— | | 205–206 |

-continued

| A | R | $R_1$ | $R_2$ | mp °C. |
|---|---|---|---|---|

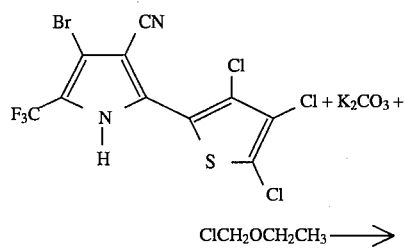

| S | Br | H | H | 183–185 |

EXAMPLE 6

Preparation of 4-Bromo-1-(ethoxymethyl)-2-(3,4,5-trichloro-2-thienyl)-5-(trifluoromethyl)pyrrole-3 carbonitrile

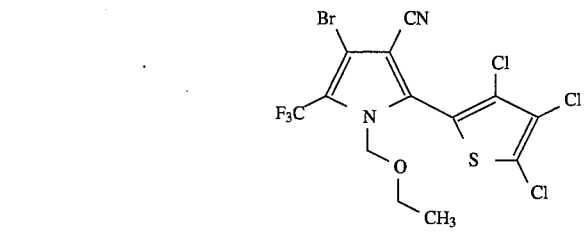

Chloromethyl ethyl ether (0.20 g, 2.13 mmol) is added to a mixture of 4-bromo-2-(3,4,5-trichloro-2-thienyl)-5-(trifluoromethyl) pyrrole-3-carbonitrile (0.30 g, 0.71 mmol) and potassium carbonate (0.29 g, 2.13 mmol) in N,N-dimethylformamide. The reation mixture is stirred at room temperature for 30 minutes, diluted with water and extracted with ether. The combined organic extracts are washed sequentially with water and brine, dried over $MgSO_4$ and concentrated in vacuo to obtain a clear oil. Flash chromatography of the oil using silica gel and a 15% ethyl acetate in hexane solution gives the title product as white crystals (0.24 g, 71%, mp 85°–87° C.).

Using essentially the same procedure, and employing the appropriately substituted 4-halo-2-(thienyl or furyl)-5-(trifluoromethyl)pyrrole-3-carbonitrile, the following compounds are obtained:

| Y | A | R | $R_1$ | $R_2$ | mp °C. |
|---|---|---|---|---|---|

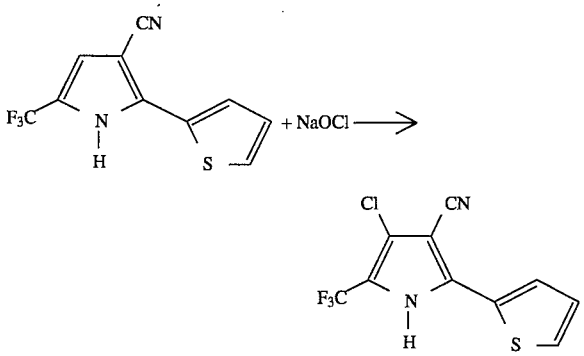

| Cl | S | H | H | H | 82–83 |
| Br | S | H | H | Br | 81–83 |
| Br | S | H | H | Cl | 81–83 |
| Br | O | H | H | Br | 80–81 |
| Br | S | Br | —CH=CH—CH=CH— | | 111–113 |
| Br | S | Cl | —CH=CH—CH=CH— | | 113–115 |

| S | Br | H | H | 109–110 |

EXAMPLE 7

Preparation of 4-Chloro-2-(2-thienyl)-5-(trifluoromethyl) pyrrole-3-carbonitrile Sodium hypochlorite (12 mL of a 5.25% solution, 17 mmol) is added dropwise to a solution of 2-(2-thienyl)-5-(trifluoromethyl)pyrrole-3-carbonitrile (2.00 g, 8.26 mmol) in tetrahydrofuran. The reaction mixture is stirred for 2 hours and 15 minutes, quenched with a 1% sodium bisulfite solution and diluted with ether. The layers are separated and the organic layer is washed sequentially with water and brine, dried over $MgSO_4$ and concentrated in vacuo to obtain a yellow solid. Flash chromatography of the solid using silica gel and a 15% ethyl acetate in hexane solution gives a solid which is recrystallized from ethyl acetate and hexane to obtain the title product as a yellow solid (0.35 g, 15%, mp 221°–223° C.). 3O

EXAMPLE 8

Preparation of 5-Bromo-2-thiophenecarbonitrile

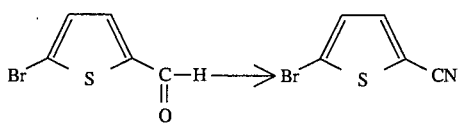

Hydroxylamine-O-sulfonic acid (17.58 g, 157 mmol) is added to a solution of 5-bromo-2-thiophenecarboxaldehyde (15.0 g, 78.5 mmol) in water and acetonitrile. The reaction mixture is stirred for 17 hours, poured into water and extracted with ether and ethyl acetate. The combined organic extracts are washed sequentially with water and brine, dried over $MgSO_4$ and concentrated in vacuo to give a brown, oily solid. A solution of the oily solid in acetic anhydride is refluxed for five hours, concentrated in vacuo, poured into water and extracted with ether. The combined organic extracts are washed sequentially with water, half-saturated sodium hydrogen carbonate solution and brine, dried over $MgSO_4$ and concentrated in vacuo to obtain a brown oil. Flash chromatography of the oil using silica gel and a 15% ethyl acetate in hexane solution gives the title product as a yellow oil (3.6 g, 24%).

EXAMPLE 9

Preparation of 2-(5-Bromo-2-furyl)-5-(trifluoromethyl)pyrrole-3-carbonitrile

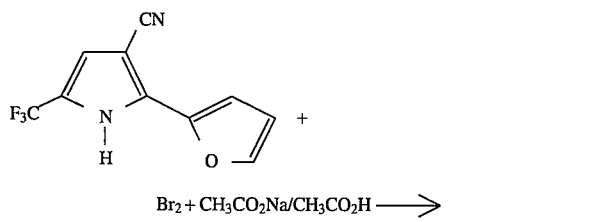

Bromine (0.71 g, 4.42 mmol) is added to a solution of 2-(2-furyl)-5-(trifluoromethyl)pyrrole-3-carbonitrile (1.00 g, 4.42 mmol) and sodium acetate (0.36 g, 4.42 mmol) in acetic acid. The reation mixture is stirred for 15 minutes and poured into a 1% sodium bisulfite solution. The solids are filtered from the aqueous mixture, dried overnight under high vacuum and recrystallized from ethyl acetate and hexane to obtain the title product as red crystals (1.21 g, 90%, mp 224°–226° C.

Using essentially the same procedure, but substituting 2-(2-thienyl)-5-(trifluoromethyl)pyrrole-3-carbonitrile for 2-(2-furyl)-5-(trifluoromethyl)-pyrrole-3-carbonitrile, 2-(2-bromo-3-thienyl)-5-(trifluoromethyl)pyrrole-3-carbonitrile is obtained as a solid, mp 170° C.

EXAMPLE 10

Preparation of 2-(5-Formyl-2-furyl)-5-(trifluoromethyl) pyrrole-3-carbonitrile

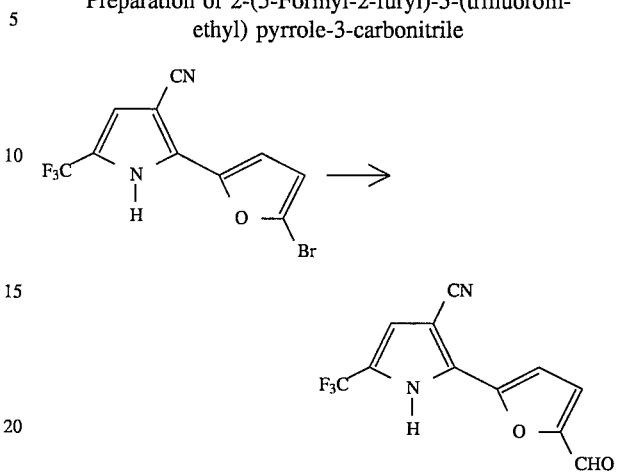

Butyllithium (3.45 mL, 7.78 mmol) is added dropwise to a solution of 2-(5-bromo-2-furyl)-5-(trifluoromethyl) pyrrole-3-carbonitrile (1.13 g, 3.70 mmol) in tetrahydrofuran at -78° C. The reation mixture is stirred at -78° C. for 30 minutes, warmed to room temperature, treated with N,N-dimethylformamide (1.35 g, 18.5 mmol), poured into one molar hydrochloric acid and extracted with ether and ethyl acetate. The combined organic extracts are washed sequentially with water and brine, dried over $Na_2SO_4$ and concentrated in vacuo to obtain an orange solid. Flash chromatography of the solid using silica gel and 20% to 50% ethyl acetate in hexane solutions give an orange solid which is recrystallized from ethyl acetate to obtain the title product as orange crystals (0.66 g, 70%, mp 224°–225° C.).

EXAMPLE 11

Preparation of Benzo[b]thiophene-2-carboxaldehyde

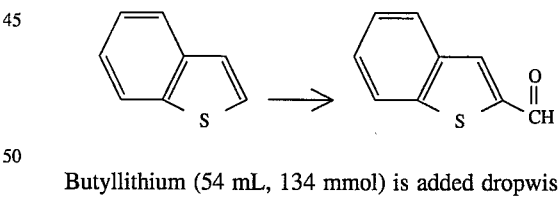

Butyllithium (54 mL, 134 mmol) is added dropwise to a solution of N,N,N',N'-tetramethylethylenediamine (15.57 g, 134 mmol) in tetrahydrofuran under nitrogen at 0° C. The reaction mixture is treated dropwise with a solution of benzothiophene (15.00 g, 112 mmol) in tetrahydrofuran, warmed to room temperature, treated with additional N,N,N',N'-tetramethylethylenediamine (15.57 g, 134 mmol) and butyllithium (54 mL, 134 mmol), stirred at room temperature for 13 hours, cooled to 0° C., treated with N,N-dimethylformamide (24.40 g, 336 mmol), warmed to room temperature, stirred for five hours, poured into one molar hydrochloric acid and extracted with ether. The combined organic extracts are washed sequentially with water and brine, dried over $Na_2SO_4$ and concentrated in vacuo to obtain an orange oil. Flash chromatography of the oil using silica gel and a 15% ethyl acetate in hexane 25 solution gives the title product as an orange oil (12.51 g, 69%).

EXAMPLE 12

Preparation of 3-Chlorobenzo[b]thiophene-2-carbonitrile

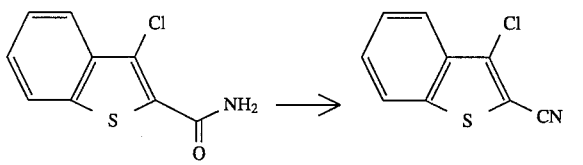

Trifluoroacetic anhydride (11.90 g, 56.6 mmol) is added dropwise to a mixture of pyridine (5.23 g, 66.1 mmol) and 3-chlorobenzo[b]thiophene-2-carboxamide (10.0 g, 47.2 mmol) in methylene chloride at 0° C. The reaction mixture is warmed to room temperature over one hour, diluted with water and extracted with ether. The combined organic extracts are washed sequentially with water, one molar hydrochloric acid and brine, dried over MgSO₄ and concentrated in vacuo to obtain a yellow solid. The solid is recrystallized from ethyl acetate and hexane to give the title product as off-white needles (8.80 g, 96%).

EXAMPLE 13

Preparation of β-[(Formylmethyl)amino-2-benzofuranacrylonitrile, diethyl acetal

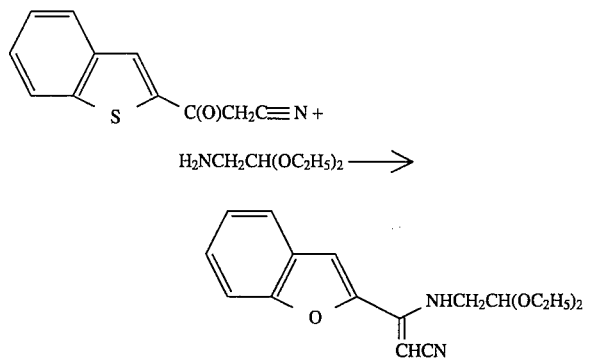

A mixture of 2-ω-cyanoacetobenzofuran (18.52 g, 100.0 mmol) and aminoacetaldehyde diethyl acetal (14.50 mL, 13.28 g, 99.7 mmol) in toluene is refluxed overnight with removal of water (Dean-Stark trap) and concentrated in vacuo to obtain a black oil. Dry column chromatography of the oil using silica gel and methylene chloride gives a reddish-black oil. The oil is mixed with a methylene chloride/hexane solution. The mixture is filtered and the filtrate is concentrated in vacuo to obtain the title product as a reddish-black oil, 10.20 g.

EXAMPLE 14

Preparation of 2-(2-Benzofuranyl)pyrrole-3-carbonitrile

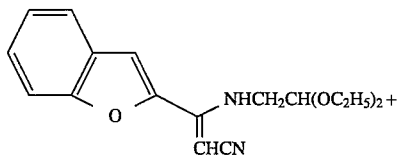

$CF_3CO_2H \longrightarrow$

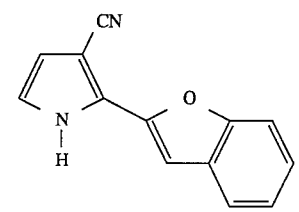

β-(Formylmethyl)amino]-2-benzofuranacrylonitrile (1.00 g, 3.33 mmol) is added dropwise to trifluoroacetic acid (5 mL). The reaction mixture is stirred at room temperature for one hour, diluted with water and extracted with ethyl acetate. The organic extract is washed sequentially with saturated sodium hydrogen carbonate solution and brine, dried over MgSO₄, decolorized with charcoal and concentrated in vacuo to obtain an orange solid. Dry column chromatography of the solid using silica gel and methylene chloride gives the title product as a brown-white solid (0.32 g, 46%, mp 157°–160.5° C.).

EXAMPLE 15

Preparation of 4,5-Dichloro-2-(3-chloro-2-benzofuranyl) pyrrole-3-carbonitrile

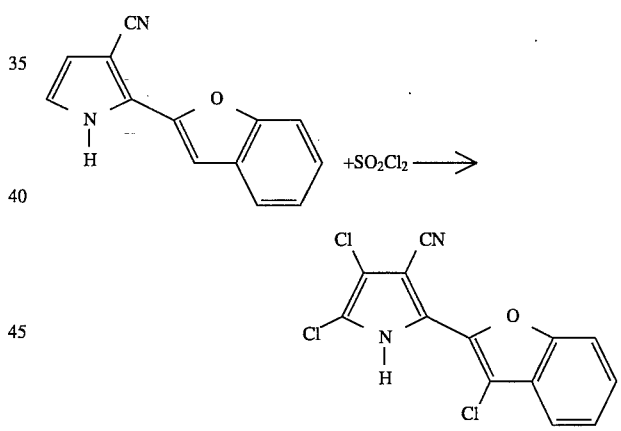

Sulfuryl chloride (1.20 mL, 2.02 g, 14.9 mmol) is added dropwise to a solution of 2-(2-benzofuranyl)pyrrole-3-carbonitrile (1.00 g, 4.8 mmol) in acetic acid. The reaction mixture is stirred at room temperature for 45 minutes and filtered to collect solids. The solids are washed with cold acetic acid and dried overnight to obtain a gray powder. A solution of the gray powder and tetrahydrofuran is dried over MgSO₄, decolorized with charcoal and concentrated in vacuo to give a yellow-white solid. A slurry of the yellow-white solid and methylene chloride is stirred for 90 minutes and filtered to obtain the title product as an off-white solid (0.74 g, mp 258°–260.5° C.).

Using essentially the same procedure, but employing two equivalents of sulfuryl chloride, 5-chloro-2-(3-chloro-2-benzofuranyl) pyrrole-3-carbonitrile is obtained as a white solid, mp 223.5°–225.5° C.

EXAMPLE 16

Preparation of 2-Bromo-1-(5-chloro-2-thienyl)etha-none

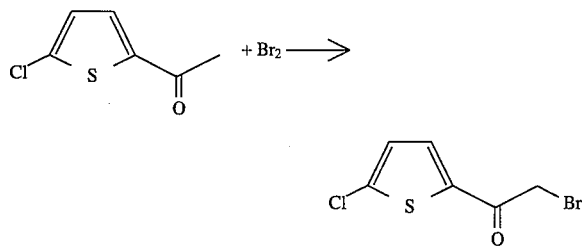

A solution of bromine (18.90 g, 118 mmol) in chloroform is added to a solution of 2-acetyl-5-chlorothiophene (19.00 g, 118 mmol) in chloroform at 40°–45° C. The reaction mixture is stirred at room temperature for two hours and diluted with water. The organic layer is separated, dried over MgSO₄ and concentrated in vacuo to give a solid. The solid is slurried in an ether/hexane solution, filtered and dried to give the title product as a solid (12.20 g, mp 68°–70° C.).

EXAMPLE 17

Preparation of [(5-Chloro-2-thenoyl)methyl]malono-nitrile

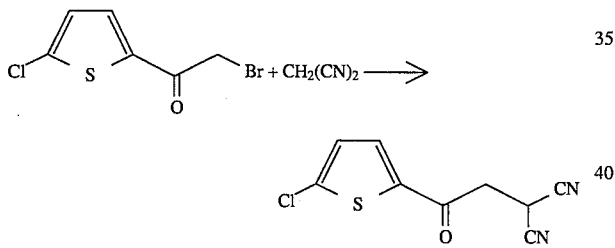

A solution of 2-bromo-1-(5-chloro-2-thienyl)ethanone (11.50 g, 48 mmol) in tetrahydrofuran is added to a solution of malononitrile (3.17 g, 48 mmol) and potassium tert-butoxide (5.70 g, 51 mmol) in tetrahydrofuran at 0° C. The reaction mixture is stirred for several minutes, concentrated in vacuo, diluted with water and filtered to collect solids. Flash chromatography of the solids using silica gel and a (4:1) hexane/ethyl acetate solution gives the title compound as a yellow solid, mp 155°–158° C.

EXAMPLE 18

Preparation of 2-Chloro-5-(5-chloro-2-thienyl)pyr-role-3-carbonitrile

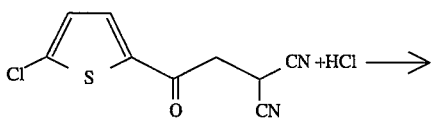

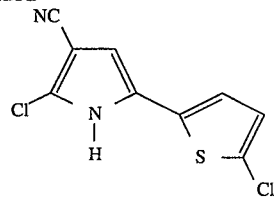

Hydrogen chloride gas is bubbled through a mixture of [(5-chloro-2-thenoyl)methyl]malononitrile (4.60 g, 20.5 mmol), ether and chloroform at a moderate rate for 20 minutes. The reaction mixture is poured into an ice-water mixture and extracted with ether. The combined organic extracts are dried over MgSO₄ and concentrated in vacuo to give a brown solid. The solid is mixed with a hexane/ether solution and filtered to obtain the title product as a brown solid, mp >200° C.

EXAMPLE 19

Preparation of 4-Bromo-2-chloro-5-(5-chloro-2-thienyl)pyrrole-3-carbonitrile

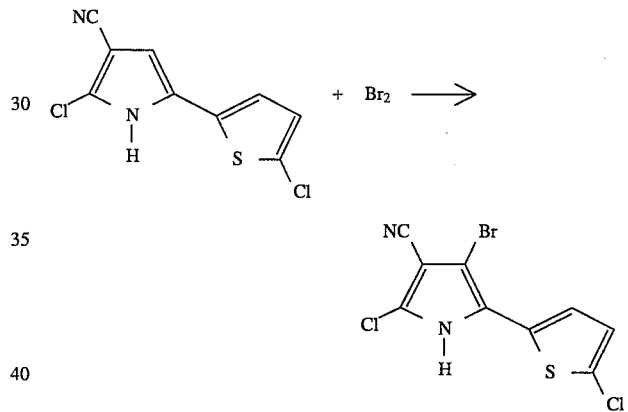

A solution of bromine (0.70 g, 4.3 mmol) in p-dioxane is added dropwise to a solution of 2-chloro-5-(5-chloro-2-thienyl)pyrrole-3-carbonitrile (1.0 g, 4.1 mmol) in p-dioxane. The reaction mixture is stirred overnight at room temperature and concentrated in vacuo to obtain a residue. Flash chromatography of the residue using silica gel and a (6:1) hexane/ethyl acetate solution gives the title product as a yellow solid, mp >200° C.

EXAMPLE 20

Preparation of 4-(p-Chlorophenyl)-2-(trifluorom-ethyl)-3-oxazolin-5-one

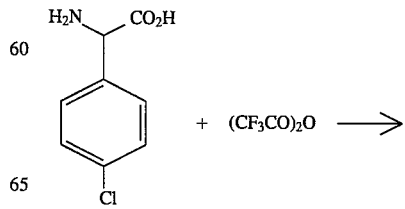

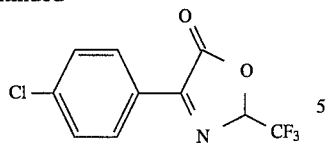

A solution of (p-chlorophenyl)glycine (5.05 g, 27.3 mmol) and trifluoroacetic anhydride (22.90 g, 109.2 mmol) in toluene is refluxed for five minutes and concentrated in vacuo to obtain the title product as a clear orange oil which is identified by high performance liquid chromatography analysis.

Using essentially the same procedure, but substituting α-amino-2-thiopheneacetic acid for (p-chlorophenyl)glycine, 4-(2-thienyl)-2-(trifluoromethyl)-3-oxazolin-5-one is obtained as a brown oil.

EXAMPLE 21

Preparation of 5-(p-Chlorophenyl)-3-[(5-nitro-2-thienyl)-2-(trifluoromethyl)pyrrole

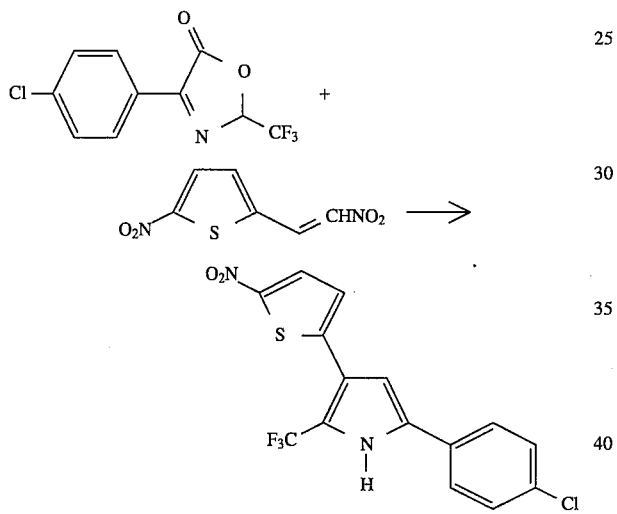

Triethylamine (1.16 g, 11.3 mmol) is added to a solution of 4-(p-chlorophenyl)-2-(trifluoromethyl)-3-oxazolin-5-one (2.97 g, 11.3 mmol) and 2-nitro-5-(2-nitrovinyl)thiophene (2.26 g, 11.3 mmol) in acetonitrile near reflux. The reaction mixture is refluxed for one hour, stirred overnight at room temperature and concentrated in vacuo to obtain a red oil. Chromatography of the oil gives the title product as a tan solid, mp 166°–169° C.

Using essentially the same procedure, but substituting 2-(2-nitrovinyl)furan for 2-nitro-5-(2-nitrovinyl)thiophene, 5-(p-chlorophenyl)-3-(2-furyl)- 2-trifluoromethyl)pyrrole is obtained as a tan solid, mp 65°–66° C.

And using essentially the same procedure, but substituting 4-(2-thienyl)-2-(trifluoromethyl)-3-oxazolin-5-one for 4-(p-chlorophenyl)-2-(trifluoromethyl)-3-oxazolin-5-one and 2-chloroacrylonitrile for 2-nitro-5-(2-nitrovinyl)thiophene, 2-(2-thienyl)-5-trifluoromethyl)pyrrole-3-carbonitrile is obtained as a tan solid, mp 210° C.

EXAMPLE 22

Preparation of 2-(p-Chlorophenyl)-3-nitro-4-(5-nitro-2-thienyl)-5-(trifluoromethyl)pyrrole

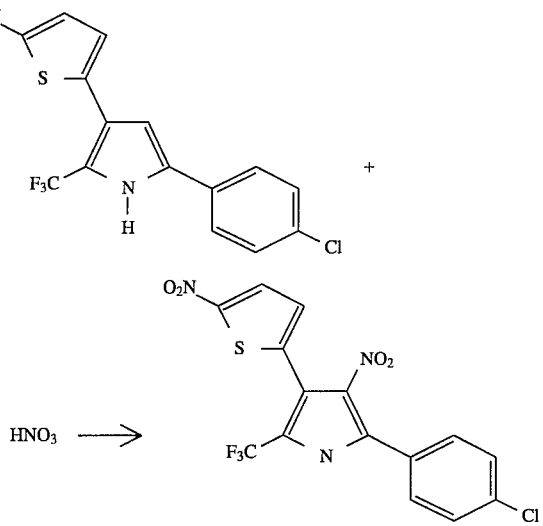

A 90% nitric acid solution (0.02 g, 0.28 mmol) is added to a solution of 5-(p-chlorophenyl)-3-(5-nitro-2-thienyl)-2-(trifluoromethyl)pyrrole (0.13 g, 0.34 mmol) in acetic anhydride. The reaction mixture is stirred at room temperature for ten minutes, treated with additional 90% nitric acid solution (0.02 g, 0.28 mmol), stirred at room temperature for 15 minutes, poured into water, stirred at room temperature overnight and extracted with ether. The combined organic extracts are dried over MgSO$_4$ and concentrated in vacuo to obtain the title product as a tan solid which is identified by $^1$HNMR spectral analysis.

EXAMPLE 23

Preparation of 4-Bromo-2-(5-bromo-2-thienyl)-5-(trifluoromethyl) pyrrole-3-carbonitrile and 4Bromo-2-[3(or 4), 5-dibromo-2-thienyl]-5-(trifluoromethyl)pyrrole-3-carbonitrile

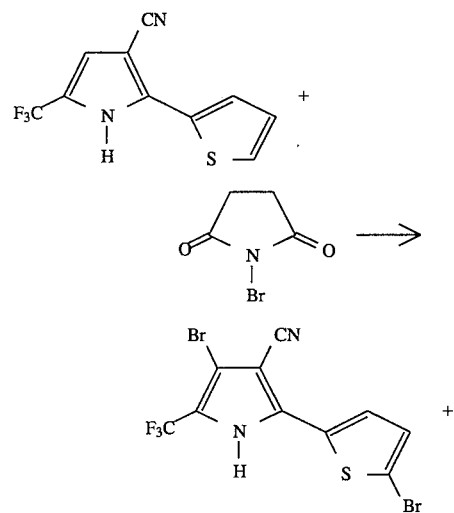

-continued

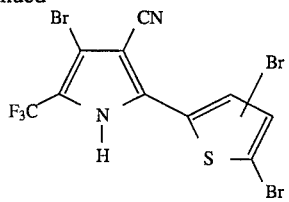

A solution of N-bromosuccinimide (0.84 g, 4.63 mmol) and 2-(2-thienyl)-5-(trifluoromethyl)pyrrole-3-carbonitrile (1.02 g, 4.21 mmol) in tetrahydrofuran is stirred at room temperature for 20 minutes, treated with additional N-bromosuccinimide (0.84 g, 4.63 mmol), stirred at room temperature for 20 minutes, stirred at reflux for two hours and poured into water. The aqueous mixture is filtered to obtain solids and filtrate. A mixture of the solids in toluene is heated, filtered and dried to give 4-bromo-2-(5-bromo-2-thienyl)-5-(trifluoromethyl) pyrrole-3carbonitrile as a solid, mp 254° C. (dec.). The filtrate obtained from the aqueous mixture is concentrated in vacuo and chromatographed using silica gel and a (4:1) hexane/ethyl acetate solution to obtain 4-bromo-2-[3(or 4),5-dibromo-2-thienyl]-5-(trifluoromethyl)pyrrole-3carbonitrile as a solid, mp 203° C.

EXAMPLE 24

Preparation of 2-[1-(5-Bromo-3-thienyl)-2-nitroethyl]-4 (p-chlorophenyl)-2-(trifluoromethyl)-3-oxazolin-5-one

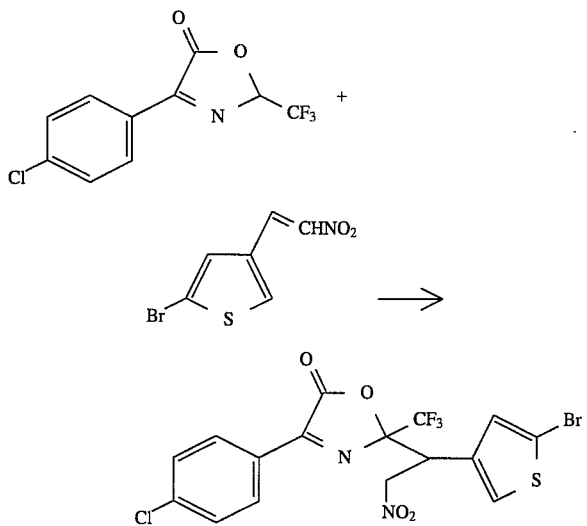

A solution of triethylamine (0.30 g, 3 mmol) in toluene is added to a solution of 4-(p-chlorophenyl)-2-(trifluoromethyl)-3-oxazolin-5-one (10.00 g, 38 mmol) and 2-bromo-4-(2-nitrovinyl)thiophene (8.98 g, 32 mmol) in toluene at 0° C. The reaction mixture is warmed to room temperature and diluted with dilute hydrochloric acid and ether. The organic layer is separated, dried over MgSO$_4$, concentrated in vacuo, diluted with hexane, stirred at reflux, cooled to room temperature and decanted to obtain a clear solution. The solution is concentrated in vacuo and chromatographed to give the title product.

EXAMPLE 25

Preparation of 3-(5-Bromo-3-thienyl)-5-(p-chlorophenyl)-2-trifluoromethyl)pyrrole and 3-(5-Bromo-3-thienyl)-5-(p-chlorophenyl)-4-nitro-2-(trifluoromethyl)pyrrole)

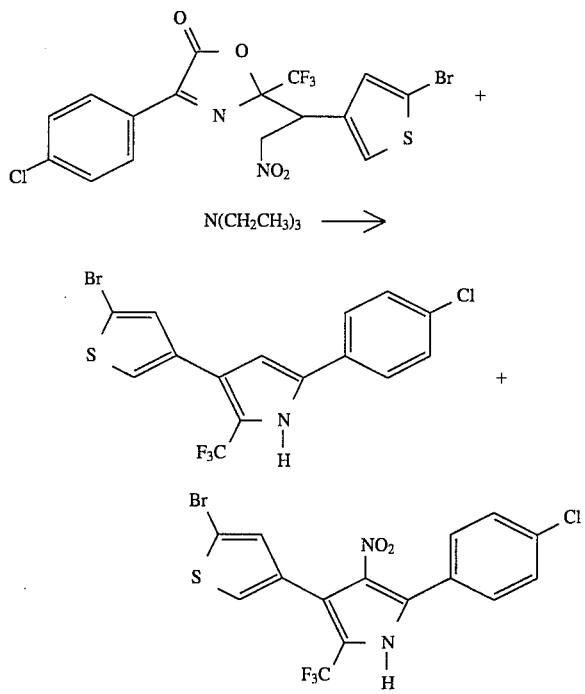

A solution of triethylamine (3.24 g, 32.1 mmol) in acetonitrile is added slowly to a solution of 2-[1-(5-bromo-3-thienyl)-2-nitroethyl]-4-(p-chlorophenyl)-2-(trifluoromethyl)- 3-oxazolin-5-one (13.30 g, 26.8 mmol) in acetonitrile. The reaction mixture is stirred at room temperature for several minutes and diluted with dilute hydrochloric acid. The organic layer is separated, dried over MgSO$_4$ and concentrated in vacuo to obtain a black residue. Column chromatography of the residue using silica gel and a (9:1) hexane/ethyl acetate solution gives several solids. One of the solids is stirred in cold 1,2-dichloroethane, filtered and dried to give 3-(5-bromo-3-thienyl)-5-(p-chlorophenyl)-2-(trifluoromethyl) pyrrole as a light tan solid, mp 112°–115° C. Another solid is diluted with hexane and the mixture is refluxed, cooled to room temperature and filtered to obtain 3-(5-bromo-3-thienyl)-5-(p-chlorophenyl)-4-nitro-2-(trifluoromethyl)pyrrole as a yellow solid, mp 174°–176° C.

EXAMPLE 26

Preparation of 3-(5-Bromo-4-nitro-3-thienyl)-5-(p-chlorophenyl)-4-nitro-2-trifluoromethyl) pyrrole)

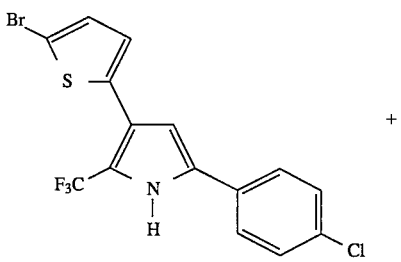

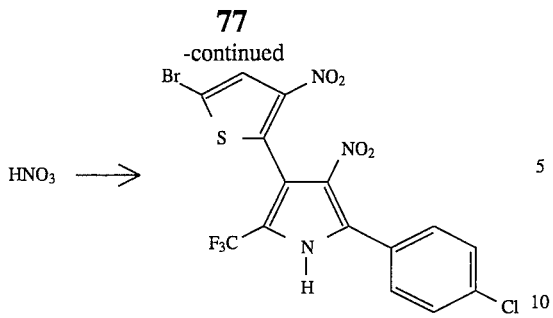

A solution of 3-(5-bromo-3-thienyl)-5-(p-chlorophenyl)-2-(trifluoromethyl) pyrrole (0.70 g, 1.7 mmol) and 90% nitric acid (0.145 g, 0.1 mL, 2.1 mmol) in acetic anhydride is stirred at room temperature for 20 minutes, treated with additional 90% nitric acid (several drops) and diluted with water. The solids are collected by filtration and dried overnight at 60° C. in a vacuum oven to give the title product as a solid, mp 186°–190° C.

EXAMPLE 27

Preparation of 2-(p-Chlorophenyl)-4-(4,5-dibromo-3-thienyl)-3-nitro-5-(trifluoromethyl)pyrrole)

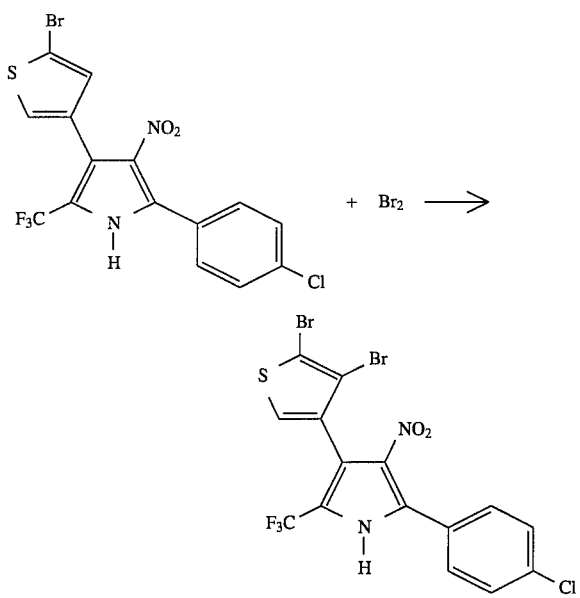

A solution of 3-(5-bromo-3-thienyl)-5-(p-chlorophenyl)-4-nitro-2-(trifluoromethyl)pyrrole (0.50 g, 1.1 mmol), bromine (0.20 g, 1.3 mmol) and sodium acetate (0.11 g, 1.3 mmol) in acetic acid (10 mL) is heated overnight at 50° C. and poured into water. The solids are collected and recrystallized from 1,2-dichloroethane to give the title product as a yellow solid, mp 241°–242° C.

EXAMPLE 28

Insecticide and acaricide evaluations

The following tests show the efficacy of the compounds as insecticides and acaricides. The evaluations are conducted with solutions of test compounds dissolved or dispersed in 50/50 acetone/water mixtures. The test compound is technical material dissolved or dispersed in said acetone/water mixtures in sufficient amounts to provide the concentrations set forth in Table I below.

All concentrations reported herein are in terms of active ingredient. All tests are conducted in a laboratory maintained at about 27° C. The rating system employed is as follows:

| Rating System | |
|---|---|
| 0 = no effect | 5 = 56–65% kill |
| 1 = 10–25% kill | 6 = 66–75% kill |
| 2 = 26–35% kill | 7 = 76–85% kill |
| 3 = 36–45% kill | 8 = 86–99% kill |
| 4 = 46–55% kill | 9 = 100% kill |
| | - = no evaluation |

The test species of insects and acarina used in the present evaluations along with specific test procedures are described below.

Spodoptera eridania third instar larvae, southern armyworm

A sieva lima bean expanded to 7 to 8 cm in length is dipped in the test suspension with agitation for three seconds and placed in a hood to dry. The leaf is then placed in a 100×10 mm petri dish containing a damp filter paper on the bottom and ten third instar caterpillars. The dish is maintained for five days before observations are made of mortality, reduced feeding or any interference with normal moulting.

Spodoptera eridania, seven-day residual

The plants treated in the above test are maintained under high intensity lamps in the greenhouse for seven days. These lamps duplicate the effects of a bright sunny day and are kept on for 14 hour day length. After seven days, the foliage is sampled and assayed as in the above-said test.

Tetranychus urticae (OP-resistant strain), two-spotted spider mite

Sieva lima bean plants with primary leaves expanded to 7 to 8 cm are selected and cut back to one plant per pot. A small piece is cut from a leaf taken from the main colony and placed on each leaf of the test plants. This is done about two hours before treatment to allow the mites to move over to the test plant and to lay eggs. The size of the cut piece is varied to obtain about 100 mites per leaf. At the time of the treatment, the piece of leaf used to transfer the mites is removed and discarded. The mite-infested plants are dipped in the test formulation for three seconds with agitation and set in the hood to dry. Plants are kept for two days before estimates of adult kill are made.

Heliothis virescens, third instar tobacco budworm

Cotton cotyledons are dipped in the test formulation and allowed to dry in a hood. When dry, each is cut into quarters and ten sections placed individually in 30 mL plastic medicine cups containg a 5 to 7 mm long piece of damp dental wick. One third instar caterpillar is added to each cup and a cardboard lid placed on the cup. Treatments are maintained for three days before mortality counts and estimates of reduction in feeding damage are made.

Diabrotica undecimpunctata howardi, third instar southern corn rootworm

One cc of fine talc is placed in a 30 mL wide-mouth screw-top glass jar. One mL of the appropriate acetone test solution is pipetted onto the talc so as to provide 1.25 mg of active ingredient per jar. The jars are set under a gentle air flow until the acetone is evaporated. The dried talc is loosened, 1 cc of millet seed is added to serve as food for the insects and 25 mL of moist soil is added to each jar. The jars are capped and the contents thoroughly mixed on a Vortex Mixer. Following this, ten third instar rootworms are added to each jar and the jars are loosely capped to allow air exchange for the larvae. The treatments are held for six days before mortality counts are made. Missing larvae are presumed dead, since they decompose rapidly and can not be found. The concentration used in this test corresponds to approximately 50 ppm.

Compounds employed in the above described insecticide and acaricide evaluations are given a compound number and identified by name. Data in Table I are reported by compound number.

| COMPOUNDS EVALUATED AS INSECTICIDAL AND ACARICIDAL AGENTS | |
|---|---|
| Compound No. | |
| 1 | 2-(p-Chlorophenyl)-4-(4,5-dibromo-3-thienyl)-3-nitro-5-(trifluoromethyl)pyrrole |
| 2 | 3-(5-Bromo-3-thienyl)-5-(p-chlorophenyl)-4-nitro-2-(trifluoromethyl)pyrrole |
| 3 | 5-(p-Chlorophenyl)-3-(2-furyl)-2-(trifluoromethyl)pyrrole |
| 4 | 3-(5-Bromo-3-thienyl)-5-(p-chlorophenyl)-2-(trifluoromethyl)pyrrole |
| 5 | 2-(2-benzofuranyl)pyrrole-3-carbonitrile |
| 6 | 3-Chloro-1-(ethoxymethyl)-2-(2-thienyl)-5-(trifluoromethyl)pyrrole-3-carbonitrile |
| 7 | 2-(2-Thienyl)-5-(trifluoromethyl)pyrrole-3-carbonitrile |
| 8 | 4-Chloro-2-(2-thienyl)-5-(trifluoromethyl)pyrrole-3-carbonitrile |
| 9 | 2-(5-Bromo-2-thienyl)-5-(trifluoromethyl)pyrrole-3-carbonitrile |
| 10 | 4-Bromo-2-(5-bromo-2-thienyl)-1-ethoxymethyl)-5-(trifluoromethyl)pyrrole-3-carbonitrile |
| 11 | 2-(5-Chloro-2-thienyl)-5-(trifluoromethyl)pyrrole-3-carbonitrile |
| 12 | 4-Bromo-2-(5-chloro-2-thienyl)-5-(trifluoromethyl)pyrrole-3-carbonitrile |
| 13 | 4-Bromo-2-(5-chloro-2-thienyl)-1-(ethoxymethyl)-5-(trifluoromethyl)pyrrole-3-carbonitrile |
| 14 | 2-(4-Bromo-2-thienyl)-5-(trifluoromethyl)pyrrole-3-carbonitrile |
| 15 | 2-(3,4,5-Trichloro-2-thienyl)-5-(trifluoromethyl)pyrrole-3-carbonitrile |
| 16 | 4-Bromo-2-(3,4,5-trichloro-2-thienyl)-5-(trifluoromethyl)pyrrole-3-carbonitrile |
| 17 | 4-Bromo-1-(ethoxymethyl)-2-(3,4,5-trichloro-2-thienyl)-5-(trifluoromethyl)pyrrole-3-carbonitrile |
| 18 | 2-(2-Bromo-3-thienyl)-5-(trifluoromethyl)pyrrole-3-carbonitrile |

-continued

| COMPOUNDS EVALUATED AS INSECTICIDAL AND ACARICIDAL AGENTS | |
|---|---|
| Compound No. | |
| 19 | 4-Bromo-2-(2-bromo-3-thienyl)-5-(trifluoromethyl)pyrrole-3-carbonitrile |
| 20 | 2-(2-Furyl)-5-(trifluoromethyl)pyrrole-3-carbonitrile |
| 21 | 1-(Ethoxymethyl)-2-(3,4,5-trichloro-2-thienyl)-5-(trifluoromethyl)pyrrole-3-carbonitrile |
| 22 | 2-(5-Formyl-2-furyl)-5-(trifluoromethyl)-pyrrole-3-carbonitrile |
| 23 | 4-Bromo-2-(5-bromo-2-thienyl)-5-(trifluoromethyl)pyrrole-3-carbonitrile |
| 24 | 2-Chloro-5-(5-chloro-2-thienyl)pyrrole-3-carbonitrile |
| 25 | 4-Bromo-2-(5-bromo-2-furyl)-1-(ethoxymethyl)-5-(trifluoromethyl)pyrrole-3-carbonitrile |
| 26 | 4-Bromo-2-(5-bromo-2-furyl)-5-(trifluoromethyl)pyrrole-3-carbonitrile |
| 27 | 2-(5-Bromo-2-furyl)-5-(trifluoromethyl)pyrrole-3-carbonitrile |
| 28 | 4-Bromo-2-(4,5-dibromo-2-thienyl)-5-(trifluoromethyl)pyrrole-3-carbonitrile |
| 29 | 4,5-Dichloro-2-(3-chloro-2-benzofuranyl)-pyrrole-3-carbonitrile |
| 30 | 5-Chloro-2-(3-chloro-2-benzofuranyl)pyrrole-3-carbonitrile |
| 31 | 4-Bromo-2-(3-chloro-2-benzo[b]thienyl)-1-(ethoxymethyl)-5-(trifluoromethyl)pyrrole-3-carbonitrile |
| 32 | 4-Bromo-2-(3-chloro-2-benzo[b]thienyl)-5-(trifluoromethyl)pyrrole-3-carbonitrile |
| 33 | 2-Benzo[b]thien-2-yl-5-(trifluoromethyl)pyrrole-3-carbonitrile |
| 34 | 4-Bromo-2-(3-bromobenzo[b]thien-2-yl)-5-(trifluoromethyl)pyrrole-3-carbonitrile |
| 35 | 4-Bromo-2-(3-bromobenzo[b]thien-2-yl)-1-(ethoxymethyl)-5-(trifluoromethyl)pyrrole-3-carbonitrile |
| 36 | 2-(p-Chlorophenyl)-3-nitro-4-(5-nitro-2-thienyl)-5-(trifluoromethyl)pyrrole |
| 37 | 4-Bromo-2-chloro-5-(5-chloro-2-thienyl)-pyrrole-3-carbonitrile |
| 38 | 2-(3-Thienyl)-5-(trifluoromethyl)pyrrole-3-carbonitrile |
| 39 | 4-Bromo-2-(2-bromo-3-thienyl)-1-(ethoxymethyl)-5-(trifluoromethyl)pyrrole-3-carbonitrile |
| 40 | 2-(3-Chloro-2-benzo[b]thienyl)-5-(trifluoromethyl)pyrrole-3-carbonitrile |

TABLE I

| Insecticide And Acaricide Evaluations | | | | | | | | |
|---|---|---|---|---|---|---|---|---|
| | Southern Armyworm | | | | OP. Res. Mites | Tobacco Budworm | | Southern Corn Rootworm |
| | | | 7-Day Residual | | | | | |
| Compound No. | (ppm) 1000 | (ppm) 300 | (ppm) 1000 | (ppm) 300 | (ppm) 300 | (ppm) 300 | (ppm) 100 | (ppm) 50 |
| 1 | 9 | — | — | — | 0 | — | 9 | 8 |
| 2 | 9 | — | — | — | 0 | — | 0 | 0 |
| 3 | 0 | — | — | — | 0 | — | — | 0 |
| 4 | 0 | — | — | — | 0 | — | — | 0 |
| 5 | 8 | — | — | — | 0 | — | — | 0 |
| 6 | — | 0 | — | 0 | 4 | 0 | 0 | 9 |
| 7 | 9 | — | 0 | — | 0 | — | — | 0 |
| 8 | 9 | 8 | — | 9 | 7 | 9 | 6 | 9 |
| 9 | 9 | 9 | — | 9 | 0 | 9 | 8 | 6 |

TABLE I-continued

Insecticide And Acaricide Evaluations

| Compound No. | Southern Armyworm (ppm) 1000 | (ppm) 300 | 7-Day Residual (ppm) 1000 | (ppm) 300 | OP. Res. Mites (ppm) 300 | Tobacco Budworm (ppm) 300 | (ppm) 100 | Southern Corn Rootworm (ppm) 50 |
|---|---|---|---|---|---|---|---|---|
| 10 | — | 0 | — | 9 | 9 | 9 | 8 | 9 |
| 11 | 9 | 9 | — | 9 | 0 | 9 | 9 | 7 |
| 12 | 9 | 9 | — | 9 | 0 | 9 | 7 | 9 |
| 13 | 9 | 9 | — | 9 | 9 | 3 | — | 9 |
| 14 | — | — | — | 9 | 0 | 9 | 8 | 8 |
| 15 | 9 | — | — | 9 | 8 | 9 | 9 | 8 |
| 16 | 9 | 9 | — | 9 | 9 | 9 | 9 | 9 |
| 17 | 9 | 9 | — | 9 | 9 | 9 | 9 | 9 |
| 18 | 2 | — | — | — | 0 | — | — | 0 |
| 19 | 9 | 9 | — | 9 | 8 | 9 | 6 | 9 |
| 20 | — | 0 | — | 0 | 0 | 0 | 0 | 9 |
| 21 | 9 | — | — | 9 | 9 | 9 | 9 | 9 |
| 22 | 0 | — | — | — | 0 | — | — | 0 |
| 23 | 9 | — | 9 | — | 0 | — | 0 | 9 |
| 24 | 9 | — | 9 | — | 0 | — | 0 | 0 |
| 25 | — | 0 | — | 9 | 9 | 9 | 9 | 9 |
| 26 | 9 | 9 | — | 9 | 0 | 9 | 9 | 9 |
| 27 | 9 | 9 | — | 9 | 4 | 4 | 0 | 8 |
| 28 | — | 9 | — | 9 | 7 | 9 | 9 | 9 |
| 29 | 9 | — | 9 | — | 0 | — | — | 7 |
| 30 | 9 | — | — | — | 0 | — | — | 0 |
| 31 | — | — | 9 | — | 0 | — | — | 9 |
| 32 | — | — | 9 | — | 0 | — | — | 9 |
| 33 | — | — | 7 | 0 | 0 | — | — | 0 |
| 34 | — | — | 9 | 8 | 0 | 9 | 8 | 6 |
| 35 | — | — | 9 | 9 | 0 | 5 | 0 | 8 |
| 36 | 9 | — | 0 | — | — | — | 9 | 9 |
| 37 | 9 | — | 9 | — | 0 | — | 9 | 0 |
| 38 | 0 | — | — | — | 0 | — | — | 0 |
| 39 | 9 | 2 | — | 3 | 0 | 2 | 0 | 9 |
| 40 | — | — | 9 | — | 0 | — | — | 7 |

What is claimed is:

1. A compound having the structural formula

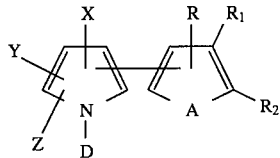

wherein

R, $R_1$ and $R_2$ are each independently hydrogen, halogen, $NO_2$ or CHO, and when $R_1$ and $R_2$ are taken together with the carbon atoms to which they are attached, they may form a ring in which $R_1R_2$ is represented by the structure:

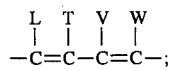

L, T, V and W are each independently hydrogen, halogen, CN or $NO_2$;

A is O or S;

X is CN, $NO_2$, $C_1$–$C_6$ haloalkyl, $S(O)_m CF_2 R_3$ or $C(S)NR_4 R_5$;

$R_3$ is hydrogen, F, Cl, Br, $CF_2H$, $CCl_2H$, $CClFH$, $CF_3$ or $CCl_3$;

m is an integer of 0, 1 or 2;

$R_4$ and $R_5$ are each independently hydrogen,
$C_1$–$C_4$ alkyl optionally substituted with one or more halogen atoms, or
phenyl optionally substituted with one or more halogen atoms,
$NO_2$ groups,
CN groups,
$C_1$–$C_4$ alkyl groups optionally substituted with one or more halogen atoms, or
$C_1$–$C_4$ alkoxy groups optionally substituted with one or more halogen atoms;

Y is hydrogen, halogen, $C_1$–$C_6$ haloalkyl, $S(O)_m CF_2 R_3$, CN or
phenyl optionally substituted with one or more halogen atoms,
$NO_2$ groups,
CN groups,
$C_1$–$C_4$ alkyl groups optionally substituted with one or more halogen atoms, or
$C_1$–$C_4$ alkoxy groups optionally substituted with one or more halogen atoms;

Z is hydrogen, halogen or $C_1$–$C_6$ haloalkyl;

B is $R_6$, $OR_6$ or CN;

$R_6$ is hydrogen, $C(O)R_7$, $CHR_8 NHC(O)R_9$, $CH_2 SQ$, $CHR_{10} OC(O)$ $(CR_{11}R_{12})_n Q_1$,
$C_1$–$C_6$ alkyl optionally substituted with one to three halogen atoms,
one tri($C_1$–$C_4$ alkyl)silyl,
one hydroxy,
one cyano,
one or two $C_1$–$C_4$ alkoxy groups optionally substituted with one to three halogen atoms, one $C_1$–$C_4$ alkylthio,
one phenyl optionally substituted with one to three halogen atoms, one to three $C_1$–$C_4$ alkyl groups or one to three $C_1$–$C_4$ alkoxy groups,
one phenoxy group optionally substituted with one to three halogen atoms, one to three $C_1$–$C_4$ alkyl groups or one to three $C_1$–$C_4$ alkoxy groups,
one benzyloxy group optionally substituted on the phenyl ring with one to three halogen atoms, one to three $C_1$–$C_4$ alkyl groups or one to three $C_1$–$C_4$ alkoxy groups,
one $C_1$–$C_6$ alkylcarbonyloxy group optionally substituted with one to three halogen atoms,
one $C_2$–$C_6$ alkenylcarbonyloxy group optionally substituted with one to three halogen atoms,
one phenylcarbonyloxy group optionally substituted with one to three halogen atoms, one to three $C_1$–$C_4$ alkyl groups or one to three $C_1$–$C_4$ alkoxy groups,
one $C_1$–$C_6$ alkoxycarbonyl group optionally substituted with one to three halogen atoms or one to three $C_1$–$C_4$ alkoxy groups, or
one benzylcarbonyloxy group optionally substituted on the phenyl ring with one to three halogen atoms, one to three $C_1$–$C_4$ alkyl groups or one to three $C_1$–$C_4$ alkoxy groups,
$C_3$–$C_6$ alkenyl optionally substituted with one to three halogen atoms or one phenyl group, or
$C_3$–$C_6$ alkynyl optionally substituted with one to three halogen atoms or one phenyl group;

$R_7$ is $C_1$–$C_6$ alkyl or $C_3$–$C_6$ cycloalkyl each optionally substituted with one to three halogen atoms,
one hydroxy,
one cyano,
one or two $C_1$–$C_4$ alkoxy groups optionally substituted with one to three halogen atoms,
one $C_1$–$C_4$ alkylthio,
one phenyl group optionally substituted with
one to three halogen atoms, one to three $C_1$–$C_4$ alkyl groups or one to three $C_1$–$C_4$ alkoxy groups,
one phenoxy group optionally substituted with one to three halogen atoms, one to three $C_1$–$C_4$ alkyl groups or one to three $C_1$–$C_4$ alkoxy groups,
one benzyloxy group optionally substituted on the phenyl ring with one to three halogen atoms, one to three $C_1$–$C_4$ alkyl groups or one to three $C_1$–$C_4$ alkoxy groups,
one $C_1$–$C_6$ alkylcarbonyloxy group optionally substituted with one to three halogen atoms,
one $C_2$–$C_6$ alkenylcarbonyloxy group optionally substituted with one to three halogen atoms,
one phenylcarbonyloxy group optionally substituted with one to three halogen atoms, one to three $C_1$–$C_4$ alkyl groups or one to three $C_1$–$C_4$ alkoxy groups,
one $C_1$–$C_6$ alkoxycarbonyl group optionally substituted with one to three halogen atoms or one to three $C_1$–$C_4$ alkoxy groups, or
one benzyloxycarbonyl group optionally substituted on the phenyl ring with one to three halogen atoms, one to three $C_1$–$C_4$ alkyl groups or one to three $C_1$–$C_4$ alkoxy groups,
$C_2$–$C_6$ alkenyl optionally substituted with one to three halogen atoms or one phenyl groups,
$C_3$–$C_6$ alkynyl optionally substituted with one to three halogen atoms or one phenyl group,
phenyl optionally substituted with one or more halogen atoms, $C_1$–$C_4$ alkyl groups, $C_1$–$C_4$ alkoxy groups, phenoxy groups, $C_1$–$C_4$ alkylthio groups, tri($C_1$–$C_4$ alkyl)silyl groups, $C_1$–$C_4$ alkylsulfinyl groups, $C_1$–$C_4$ alkylsulfonyl groups, CN groups, $NO_2$ groups or $CF_3$ groups,
phenoxy optionally substituted with one or more halogen atoms, $C_1$–$C_4$ alkyl groups, $C_1$–$C_4$ alkoxy groups, $C_1$–$C_4$ alkylthio groups, tri($C_1$–$C_4$ alkyl)silyl groups, $C_1$–$C_4$ alkylsulfinyl groups, $C_1$–$C_4$ alkylsulfonyl groups, CN groups, $NO_2$ groups or $CF_3$ groups,
1- or 2-naphthyl,
2-, 3-, or 4-pyridyl optionally substituted with one to three halogen atoms,
$C_1$–$C_6$ alkoxy optionally substituted with one to three halogen atoms, or
$C_2$–$C_6$ alkenyloxy optionally substituted with one to three halogen atoms;

$R_8$ is hydrogen or $C_1$–$C_4$ alkyl;

$R_9$ is $C_1$–$C_6$ alkyl optionally substituted with one to three halogen atoms,
phenyl optionally substituted with one to three halogen atoms, CN groups, $NO_2$ groups, $C_1$–$C_4$ alkyl groups, $C_1$–$C_4$ alkoxy groups or $CF_3$ groups,
2- or 3-thienyl, or
2- or 3-furyl;

$$\overset{A_1}{\underset{}{\|}}C{-}R_{13},\quad \overset{A_1}{\underset{}{\|}}C{-}OR_{14},$$

$$\overset{A_1}{\underset{}{\|}}C{-}NR_{15}R_{16},\quad \overset{A_1}{\underset{}{\|}}P{-}(OR_{17})_2,$$

$$\overset{NR_{18}}{\underset{}{\|}}C{-}NR_{19}R_{20},\quad \overset{NR_{18}}{\underset{}{\|}}C{-}A_1R_{21},$$

structures with $A_1$, $R_{22}$, $R_{23}$ substituents on N-containing rings, and analogous with NH, CN,
$C_1$–$C_6$ alkyl optionally substituted with one or more halogen atoms, CN groups or phenyl groups, or
phenyl optionally substituted with one or more halogen atoms, $C_1$–$C_4$ alkyl groups, $C_1$–$C_4$ alkoxy groups, CN groups, $NO_2$ groups, $CF_3$ groups or $NR_{24}R_{25}$ groups;

$A_1$ is O or S;

$R_{13}$ is $C_1$–$C_6$ alkyl or phenyl;

$R_{14}$ is $C_1$–$C_6$ alkyl;

$R_{15}$ and $R_{16}$ are each independently hydrogen, $C_1$–$C_6$ alkyl or may be taken together with the atom to which they are attached to form a 5- to 7-membered heterocyclic ring;

$R_{17}$ is $C_1$–$C_4$ alkyl;

$R_{18}$ is hydrogen, $C_1$–$C_4$ alkyl or may be taken together with either $R_{19}$ or $R_{21}$ and the atoms to which they are attached to form a 5- to 7-membered heterocyclic ring optionally substituted with one or two $C_1$–$C_4$ alkyl groups;

$R_{19}$ and $R_{20}$ are each independently hydrogen or $C_1$–$C_4$ alkyl;

$R_{21}$ is $C_1$–$C_4$ alkyl or when taken together with $R_{18}$ and the atoms to which they are attached may form a 5- to 7-membered heterocyclic ring optionally substituted with one or two $C_1$–$C_4$ alkyl groups;

$R_{22}$ and $R_{23}$ are each independently hydrogen or $C_1$–$C_4$ alkyl or when taken together may form a ring wherein $R_{22}R_{23}$ is represented by —CH=CH—CH=CH—;

$R_{24}$ and $R_{25}$ are each independently hydrogen or $C_1$–$C_4$ alkyl;

$R_{10}$ is hydrogen or $C_1$–$C_4$ alkyl;

$R_{11}$ and $R_{12}$ are each independently hydrogen,
   $C_1$–$C_6$ alkyl optionally substituted with one or more halogen atoms,
   $C_1$–$C_6$ alkoxy optionally substituted with one or more halogen atoms,
   $C_1$–$C_6$ alkylthio optionally substituted with one or more halogen atoms, or
   phenyl optionally substituted with one or more halogen atoms,
     $NO_2$ groups;
     CN groups,
     $C_1$–$C_4$ alkyl groups optionally substituted with one or more halogen atoms, or
     $C_1$–$C_4$ alkoxy groups optionally substituted with one or more halogen atoms, or
   when $R_{11}$ and $R_{12}$ are taken together with the atom to which they are attached may form a $C_3$–$C_6$ cycloalkyl group optionally substituted with one to three $C_1$–$C_4$ alkyl groups, $C_2$–$C_6$ alkenyl groups or phenyl groups, or $R_{11}$ or $R_{12}$ may be taken together with $R_{26}$ and the atoms to which they are attached to form a 4- to 7-membered heterocyclic ring;

n is an integer of 0, 1, 2, 3 or 4;

$Q_1$ is $A_2R_{26}$,

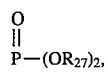

$NR_{28}R_{29}$, $CR_{30}R_{31}C(O)R_{32}$, or
   $C_3$–$C_6$ cycloalkyl optionally substituted with one or more $C_1$–$C_6$ alkyl groups,
   $C_2$–$C_6$ alkenyl groups, or
   phenyl groups optionally substituted with one or more halogen atoms,
     $NO_2$ groups,
     CN groups,
     $C_1$–$C_4$ alkyl groups optionally substituted with one or more halogen atoms, or
     $C_1$–$C_4$ alkoxy groups optionally substituted with one or more halogen atoms;

$A_2$ is O or $S(O)_p$;

p is an integer of 0, 1 or 2;

$R_{26}$ is hydrogen,
   $C_1$–$C_6$ alkyl
   $C_2$–$C_6$ alkenyl,
   $C_2$–$C_6$ alkynyl,
   phenyl optionally substituted with one or more halogen atoms,
     $NO_2$ groups,
     CN groups,
     $C_1$–$C_4$ alkyl groups optionally substituted with one or more halogen atoms,
     $C_1$–$C_4$ alkoxy groups optionally substituted with one or more halogen atoms,
   $C(O)R_{33}$ provided p is O,
   $C(O)R_{34}$ provided p is O,
   $(CH_2CH_2O)_qR_{33}$, or

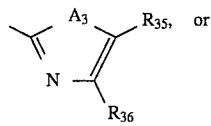

$R_{26}$ may be taken together with either $R_{11}$ or $R_{12}$ and the atoms to which they are attached to form a 4- to 7-membered heterocyclic ring;

$A_3$ is O or S;

$R_{33}$ is $C_1$–$C_6$ alkyl,
   $C_2$–$C_6$ alkenyl,
   $C_2$–$C_6$ alkynyl, or
   phenyl optionally substituted with one or more halogen atoms,
     $NO_2$ groups,
     CN groups,
     $C_1$–$C_4$ alkyl groups optionally substituted with one or more halogen atoms, or
     $C_1$–$C_4$ alkoxy groups optionally substituted with one or more halogen atoms;

q is an integer of 1, 2 or 3;

$R_{34}$ is $OR_{37}$ or $NR_{38}R_{39}$;

$R_{37}$ is $C_1$–$C_6$ alkyl or
   phenyl optionally substituted with one or more halogen atoms,
     $NO_2$ groups,
     CN groups,
     $C_1$–$C_4$ alkyl groups optionally substituted with one or more halogen atoms, or
     $C_1$–$C_4$ alkoxy groups optionally substituted with one or more halogen atoms;

$R_{38}$ and $R_{39}$ are each independently hydrogen or $C_1$–$C_4$ alkyl;

$R_{35}$ and $R_{36}$ are each independently hydrogen or $C_1$–$C_4$ alkyl, or
   when taken together may form a ring wherein $R_{35}R_{36}$ is represented by —CH=CH—CH=CH—;

$R_{27}$ is $C_1$–$C_4$ alkyl;

$R_{28}$ is hydrogen,
   $C_1$–$C_6$ alkyl,
   $C_2$–$C_6$ alkenyl,
   $C_2$–$C_6$ alkynyl, or
   phenyl optionally substituted with one or more halogen atoms,
     $NO_2$ groups,
     CN groups,
     $C_1$–$C_4$ alkyl groups optionally substituted with one or more halogen atoms, or
     $C_1$–$C_4$ alkoxy groups optionally substituted with one or more halogen atoms, or $R_{28}$ may be taken together with either $R_{11}$ or $R_{12}$ and the atoms to which they are attached to form a 4- to 7-membered heterocyclic ring;

$R_{29}$ is hydrogen,
   $C_1$–$C_6$ alkyl,
   $C_2$–$C_6$ alkenyl,
   $C_2$–$C_6$ alkynyl,
   phenyl optionally substituted with one or more halogen atoms,
     $NO_2$ groups,
     CN groups,
     $C_1$–$C_4$ alkyl groups optionally substituted with one or more halogen atoms, or
     $C_1$–$C_4$ alkoxy groups optionally substituted with one or more halogen atoms, $C(A_4)R_{40}$,
CN,
$SO_2R_{41}$, or
$C(O)CHR_{42}NHR_{43}$;

$A_4$ is O or S;

$R_{40}$ is $OR_{44}$, $CO_2R_{44}$, $NR_{45}R_{46}$,
$C_1$–$C_6$ alkyl optionally substituted with one to three halogen atoms,
$C_2$–$C_6$ alkenyl,
$C_2$–$C_6$ alkynyl, or
phenyl optionally substituted with one or more halogen atoms,
$NO_2$ groups,
CN groups,
$C_1$–$C_4$ alkyl groups optionally substituted with one or more halogen atoms, or
$C_1$–$C_4$ alkoxy groups optionally substituted with one or more halogen atoms;

$R_{44}$ is $C_1$–$C_6$ alkyl optionally substituted with one phenyl group, or
phenyl optionally substituted with one or more halogen atoms,
$NO_2$ groups,
CN groups,
$C_1$–$C_4$ alkyl groups optionally substituted with one or more halogen atoms, or
$C_1$–$C_4$ alkoxy groups optionally substituted with one or more halogen atoms;

$R_{45}$ and $R_{46}$ are each independently hydrogen or $C_1$–$C_4$ alkyl;

$R_{41}$ is $NR_{47}R_{48}$,
$C_1$–$C_6$ alkyl,
$C_2$–$C_6$ alkenyl,
$C_2$–$C_6$ alkynyl, or
phenyl optionally substituted with one or more halogen atoms,
$NO_2$ groups,
CN groups,
$C_1$–$C_4$ alkyl groups optionally substituted with one or more halogen atoms, or
$C_1$–$C_4$ alkoxy groups optionally substituted with one or more halogen atoms;

$R_{47}$ and $R_{48}$ are each independently hydrogen or $C_1$–$C_4$ alkyl;

$R_{42}$ is hydrogen,
$C_1$–$C_4$ alkyl optionally substituted with one hydroxy group,
one SR49 group,
one $C(O)NH_2$ group,
one $NH_2$ group,
one $NHC(=NH)NH_2$ group,
one $CO_2H$ group,
one phenyl group optionally substituted with one hydroxy group,
one 3-indolyl group or
one 4-imidazolyl group;

$R_{49}$ is hydrogen or $C_1$–$C_4$ alkyl;

$R_{43}$ is $C(A_4)R_{50}$;

$R_{50}$ is $C_1$–$C_6$ alkyl optionally substituted with one or more halogen atoms,
$C_1$–$C_6$ alkoxyalkyl,
$C_1$–$C_6$ alkylthio,
phenyl optionally substituted with one or more halogen atoms,
$NO_2$ groups,
CN groups,
$C_1$–$C_4$ alkyl groups optionally substituted with one or more halogen atoms, or
$C_1$–$C_4$ alkoxy groups optionally substituted with one or more halogen atoms,
$OR_{44}$,
$CO_2R_{44}$ or
$NR_{45}R_{46}$;

$R_{30}$ and $R_{31}$ are each independently hydrogen,
$C_1$–$C_6$ alkyl optionally substituted with one or more halogen atoms,
$C_1$–$C_6$ alkoxy optionally substituted with one or more halogen atoms,
$C_1$–$C_6$ alkylthio optionally substituted with one or more halogen atoms,
phenyl optionally substituted with one or more halogen atoms,
CN groups,
$NO_2$ groups,
$C_1$–$C_4$ alkyl groups optionally substituted with one or more halogen atoms, or
$C_1$–$C_4$ alkoxy groups optionally substituted with one or more halogen atoms, or
when $R_{30}$ and $R_{31}$ are taken together with the atom to which they are attached may form a $C_3$–$C_6$ cycloalkyl group optionally substituted with one to three $C_1$–$C_4$ alkyl groups, $C_2$–$C_6$ alkenyl groups or phenyl groups;

$R_{32}$ is $OR_{51}$, $NR_{47}R_{48}$, $C_1$–$C_4$ alkyl or
phenyl optionally substituted with one or more halogen atoms,
CN groups,
$NO_2$ groups,
$C_1$–$C_4$ alkyl groups optionally substituted with one or more halogen atoms, or
$C_1$–$C_4$ alkoxy groups optionally substituted with one or more halogen atoms; and $R_{51}$ is $C_1$–$C_4$ alkyl or
phenyl optionally substituted with one or more halogen atoms,
CN groups,
$NO_2$ groups,
$C_1$–$C_4$ alkyl groups optionally substituted with one or more halogen atoms, or
$C_1$–$C_4$ alkoxy groups optionally substituted with one or more halogen atoms;

provided that when A is S, X is $S(O)_mCF_2R_3$ and Z is hydrogen, then Y is hydrogen, halogen, $C_1$–$C_6$ haloalkyl, $S(O)_mCF_2R_3$ or CN; and further provided that when the pyrrole ring is substituted with hydrogen at each of the pyrrole carbon atoms adjacent to the ring nitrogen atom, then X cannot be CN or $NO_2$.

2. The compound according to claim 1 wherein R, $R_1$ and $R_2$ are each independently hydrogen, halogen or $NO_2$, and when $R_1$ and $R_2$ are taken together with the carbon atoms to which they are attached, they may form a ring in which $R_1R_2$ is represented by the structure:

$$\begin{array}{cccc} L & T & V & W \\ | & | & | & | \\ -C{=}C{-}C{=}C{-}; \end{array}$$

L, T, V and W are each independently hydrogen, halogen, CN or $NO_2$;

A is O or S;

X is CN, $NO_2$, $C_1$–$C_6$ haloalkyl, $S(O)_mCF_2R_3$ or $C(S)NR_4R_5$;

$R_3$ is hydrogen, F, Cl, Br, $CF_2H$, $CCl_2H$, $CClFH$, $CF_3$ or $CCl_3$;

m is an integer of 0, 1 or 2;

$R_4$ and $R_5$ are each independently hydrogen,
$C_1$–$C_4$ alkyl optionally substituted with one or more halogen atoms or
phenyl optionally substituted with one or more halogen atoms,
$NO_2$ groups,
CN groups,
$C_1$–$C_4$ alkyl groups optionally substituted with one or more halogen atoms, or
$C_1$–$C_4$ alkoxy groups optionally substituted with one or more halogen atoms;

Y is hydrogen, halogen, $C_1$–$C_6$ haloalkyl, $S(O)_mCF_2R_3$, CN or
phenyl optionally substituted with one or more halogen atoms,
$NO_2$ groups,
CN groups,
$C_1$–$C_4$ alkyl groups optionally substituted with one or more halogen atoms, or
$C_1$–$C_4$ alkoxy groups optionally substituted with one or more halogen atoms;

Z is hydrogen, halogen or $C_1$–$C_6$ haloalkyl;

D is $R_6$ or CN;

$R_6$ is hydrogen, $C(O)_7$ or
$C_1$–$C_6$ alkyl optionally substituted with one to three halogen atoms,
one cyano,
one $C_1$–$C_4$ alkoxy group,
one $C_1$–$C_6$ alkylcarbonyloxy group,
one phenylcarbonyloxy group, or
one benzylcarbonyloxy groups; and $R_7$ is phenyl optionally substituted with one or more halogen atoms, $C_1$–$C_4$ alkyl groups, $C_1$–$C_4$ alkoxy groups, CN groups, $NO_2$ groups or $CF_3$ groups.

3. The compound according to claim 2 wherein R, $R_1$ and $R_2$ are each independently hydrogen, halogen or $NO_2$, and when $R_1$ and $R_2$ are taken together with the carbon atoms to which they are attached, they may form a ring in which $R_1R_2$ is represented by the structure:

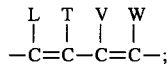

L, T, V and W are each independently hydrogen, halogen, CN or $NO_2$;

A is O or S;

X is CN, $NO_2$ or $C_1$–$C_6$ haloalkyl;

Y is hydrogen, halogen, $C_1$–$C_6$ haloalkyl or
phenyl optionally substituted with one or more halogen atoms,
$NO_2$ groups,
CN groups,
$C_1$–$C_4$ alkyl groups optionally substituted with one or more halogen atoms, or
$C_1$–$C_4$ alkoxy groups optionally substituted with one or more halogen atoms;

Z is hydrogen, halogen or $C_1$–$C_6$ haloalkyl;

D is $R_6$ or CN;

$R_6$ is hydrogen, $C(O)R_7$ or
$C_1$–$C_6$ alkyl optionally substituted with one to three halogen atoms,
one cyano,
one $C_1$–$C_4$ alkoxy group,
one $C_1$–$C_6$ alkylcarbonyloxy group,
one phenylcarbonyloxy group, or
one benzylcarbonyloxy group; and $R_7$ is phenyl optionally substituted with one or more halogen atoms, $C_1$–$C_4$ alkyl groups, $C_1$–$C_4$ alkoxy groups, CN groups, $NO_2$ groups or $CF_3$ groups.

4. The compound according to claim 3 wherein R, $R_1$ and $R_2$ are each independently hydrogen, halogen or $NO_2$, and when $R_1$ and $R_2$ are taken together with the carbon atoms to which they are attached, they may form a ring in which $R_1R_2$ is represented by the structure:

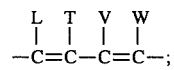

L, T, V and W are each independently hydrogen, halogen, CN or $NO_2$;

A is O or S;

X is CN, $NO_2$ or $C_1$–$C_6$ haloalkyl;

Y is hydrogen, halogen, $C_1$–$C_6$ haloalkyl or
phenyl optionally substituted with one or more halogen atoms,
$NO_2$ groups,
CN groups,
$C_1$–$C_4$ alkyl groups optionally substituted with one or more halogen atoms, or
$C_1$–$C_4$ alkoxy groups optionally substituted with one or more halogen atoms;

Z is halogen or $C_1$–$C_6$ haloalkyl;

B is $R_6$ or CN;

$R_6$ is hydrogen, $C(O)R_7$ or
$C_1$–$C_6$ alkyl optionally substituted with one to three halogen atoms,
one cyano,
one $C_1$–$C_4$ alkoxy group,
one $C_1$–$C_6$ alkylcarbonyloxy group,
one phenylcarbonyloxy group, or
one benzylcarbonyloxy group; and $R_7$ is phenyl optionally substituted with one or more halogen atoms, $C_1$–$C_4$ alkyl groups, $C_1$–$C_4$ alkoxy groups, CN groups, $NO_2$ groups or $CF_3$ groups.

5. The compound according to claim 3 wherein

R, $R_1$ and $R_2$ are each independently hydrogen, halogen or $NO_2$, and when $R_1$ and $R_2$ are taken together with the carbon atoms to which they are attached, they may form a ring in which $R_1R_2$ is represented by the structure:

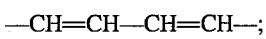

A is O or S;

X is CN or $NO_2$;

Y is halogen, $CF_3$ or
phenyl optionally substituted with one or more halogen atoms,
$NO_2$ groups,
CN groups,
$C_1$–$C_4$ alkyl groups optionally substituted with one or more halogen atoms, or
$C_1$–$C_4$ alkoxy groups optionally substituted with one or more halogen atoms;

Z is hydrogen, halogen or $CF_3$; and

D is hydrogen or $C_1$–$C_6$ alkyl substituted with one $C_1$–$C_4$ alkoxy group.

6. The compound according to claim 5 wherein R, $R_1$ and $R_2$ are each independently hydrogen, halogen or $NO_2$;

A is O or S;

X is CN or $NO_2$;

Y is halogen, $CF_3$ or
 phenyl optionally substituted with one or more halogen atoms,
 $NO_2$ groups,
 CN groups,
 $C_1$–$C_4$ alkyl groups optionally substituted with one or more halogen atoms, or
 $C_1$–$C_4$ alkoxy groups optionally substituted with one or more halogen atoms;

Z is $CF_3$; and

B is hydrogen or $C_1$–$C_6$ alkyl substituted with one $C_1$–$C_4$ alkoxy group.

7. The compound according to claim 5 4-bromo-1-(ethoxymethyl)-2-(3,4,5-trichloro-2-thienyl)-5-(trifluoromethyl)pyrrole-3-carbonitrile.

8. The compound according to claim 5 4-bromo-2-(3,4,5-trichloro-2-thienyl)-5-(trifluoromethyl)pyrrole-3-carbonitrile.

9. The compound according to claim 5 4-bromo-2-(5-bromo-2-furyl)-1-(ethoxymethyl)-5-(trifluoromethyl)pyrrole-3-carbonitrile.

10. The compound according to claim 5 4-bromo-2-(5-bromo-2-furyl)-5-(trifluoromethyl)pyrrole-3-carbonitrile.

11. The compound according to claim 5 1-(ethoxymethyl)-2-(3,4,5-trichloro-2-thienyl)-5-(trifluoromethyl)pyrrole-3-carbonitrile.

12. The compound according to claim 5 2-(5-chloro-2-thienyl)-5-(trifluoromethyl)pyrrole-3-carbonitrile.

13. The compound according to claim 5 2-(p-chlorophenyl)-4-(4,5-dibromo-3-thienyl)-3-nitro-5-(trifluoromethyl)pyrrole.

14. The compound according to claim 5 2-(3,4,5-trichloro-2-thienyl)-5-(trifluoromethyl)pyrrole-3-carbonitrile.

15. The compound according to claim 5 4-bromo-2-(4,5-dibromo-2-thienyl)-5-(trifluoromethyl)pyrrole-3-carbonitrile.

16. The compound according to claim 5 2-(p-chlorophenyl)-3-nitro-4-(5-nitro-2-thienyl)-5-(trifluoromethyl)pyrrole.

17. The compound according to claim 5 4-bromo-2-chloro-5-(5-chloro-2-thienyl)pyrrole-3-carbonitrile.

18. A method for controlling insects and acarina which comprises contacting said insects and acarina, their breeding grounds, food supply or habitat with an insecticidally or acaricidally effective amount of a compound having the structural formula wherein R, $R_1$, $R_2$, A, X, Y, Z and D are as described in claim 1.

19. The method according to claim 18 wherein R, $R_1$, $R_2$, A, X, Y, Z and D are as described in claim 2.

20. The method according to claim 19 wherein R, $R_1$, $R_2$, A, X, Y, Z and D are as described in claim 3.

21. The method according to claim 20 wherein R, $R_1$, $R_2$, A, X, Y, Z and D are as described in claim 4.

22. The method according to claim 20 wherein R, $R_1$ and $R_2$ are each independently hydrogen, halogen or $NO_2$, and when $R_1$ and $R_2$ are taken together with the carbon atoms to which they are attached, they may form a ring in which $R_1R_2$ is represented by the structure:

—CH=CH—CH=CH—;

A is O or S;

X is CN or $NO_2$;

Y is halogen, $CF_3$ or
 phenyl optionally substituted with one or more halogen atoms,
 $NO_2$ groups,
 CN groups,
 $C_1$–$C_4$ alkyl groups optionally substituted with one or more halogen atoms, or
 $C_1$–$C_4$ alkoxy groups optionally substituted with one or more halogen atoms;

Z is hydrogen, halogen or $CF_3$; and

D is hydrogen or $C_1$–$C_6$ alkyl substituted with one $C_1$–$C_4$ alkoxy group.

23. The method according to claim 22 wherein R, $R_1$ and $R_2$ are each independently hydrogen, halogen or $NO_2$;

A is O or S;

X is CN or $NO_2$;

Y is halogen, $CF_3$ or
 phenyl optionally substituted with one or more halogen atoms,
 $NO_2$ groups,
 CN groups,
 $C_1$–$C_4$ alkyl groups optionally substituted with one or more halogen atoms, or
 $C_1$–$C_4$ alkoxy groups optionally substituted with one or more halogen atoms;

Z is $CF_3$; and

D is hydrogen or $C_1$–$C_6$ alkyl substituted with one $C_1$–$C_4$ alkoxy group.

24. The method according to claim 22 wherein the compound is selected from the group consisting of 4-bromo-1-(ethoxymethyl)-2-(3,4,5-trichloro-2-thienyl)-5-(trifluoromethyl)pyrrole-3-carbonitrile;

4-bromo-2-(3,4,5-trichloro-2-thienyl)-5-(trifluoromethyl)pyrrole-3-carbonitrile;

4-bromo-2-(5-bromo-2-furyl)-1-(ethoxymethyl)-5-(trifluoromethyl)pyrrole-3-carbonitrile;

4-bromo-2-(5-bromo-2-furyl)-5-(trifluoromethyl)pyrrole-3-carbonitrile;

1-(ethoxymethyl)-2-(3,4,5-trichloro-2-thienyl)-5-(trifluoromethyl)pyrrole-3-carbonitrile;

2-(5-chloro-2-thienyl)-5-(trifluoromethyl)pyrrole-3-carbonitrile;

2-(p-chlorophenyl)-4-(4,5-dibromo-3-thienyl)-3-nitro-5-(trifluoromethyl)pyrrole;

2-(3,4,5-trichloro-2-thienyl)-5-(trifluoromethyl)pyrrole-3-carbonitrile;

4-bromo-2-(4,5-dibromo-2-thienyl)-5-(trifluoromethyl)pyrrole-3-carbonitrile;

2-(p-chlorophenyl)-3-nitro-4-(5-nitro-2-thienyl)-5-(trifluoromethyl)pyrrole; and 4-bromo-2-chloro-5-(5-chloro-2-thienyl)pyrrole-3-carbonitrile.

25. The method according to claim 18 further comprising the simultaneous or sequential addition of an insecticidally or acaricidally effective amount of one or more other biological chemicals.

26. A method for protecting growing plants from attack by insects and acarina which comprises applying to the foliage of said plants or to the soil or water in which they are growing an insecticidally or acaricidally effective amount of a compound having the structural formula

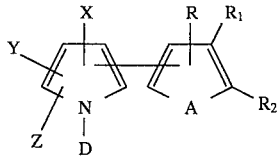

wherein R, $R_1$, $R_2$, A, X, Y, Z and D are as described in claim 1.

27. The method according to claim 26 wherein R, $R_1$, $R_2$, A, X, Y, Z and D are as described in claim 2.

28. The method according to claim 27 wherein R, $R_1$, $R_2$, A, X, Y, Z and D are as described in claim 3.

29. The method according to claim 28 wherein R, $R_1$, $R_2$, A, X, Y, Z and D are as described in claim 4.

30. The method according to claim 28 wherein

R, $R_1$ and $R_2$ are each independently hydrogen, halogen or $NO_2$ and when $R_1$ and $R_2$ are taken together with the carbon atoms to which they are attached, they may form a ring in which $R_1R_2$ is represented by the structure:

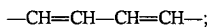
—CH=CH—CH=CH—;

A is O or S;

X is CN or $NO_2$;

Y is halogen, $CF_3$ or
phenyl optionally substituted with one or more halogen atoms,
$NO_2$ groups,
CN groups,
$C_1$–$C_4$ alkyl groups optionally substituted with one or more halogen atoms, or
$C_1$–$C_4$ alkoxy groups optionally substituted with one or more halogen atoms;

Z is hydrogen, halogen or $CF_3$; and

D is hydrogen or $C_1$–$C_6$ alkyl substituted with one $C_1$–$C_4$ alkoxy group.

31. The method according to claim 30 wherein R, $R_1$ and $R_2$ are each independently hydrogen, halogen or $NO_2$;

A is O or S;

X is CN or $NO_2$;

Y is halogen, $CF_3$ or
phenyl optionally substituted with one or more halogen atoms,
$NO_2$ groups,
CN groups,
$C_1$–$C_4$ alkyl groups optionally substituted with one or more halogen atoms, or
$C_1$–$C_4$ alkoxy groups optionally substituted with one or more halogen atoms;

Z is $CF_3$; and

D is hydrogen or $C_1$–$C_6$ alkyl substituted with one $C_1$–$C_4$ alkoxy group.

32. The method according to claim 30 wherein the compound is selected from the group consisting of 4-bromo-1-(ethoxymethyl)-2-(3,4,5-trichloro-2-thienyl)-5-(trifluoromethyl)pyrrole-3-carbonitrile;

4-bromo-2-(3,4,5-trichloro-2-thienyl)-5-(trifluoromethyl)pyrrole-3-carbonitrile;

4-bromo-2-(5-bromo-2-furyl)-1-(ethoxymethyl)-5-(trifluoromethyl)pyrrole-3-carbonitrile;

4-bromo-2-(5-bromo-2-furyl)-5-(trifluoromethyl)pyrrole-3-carbonitrile;

1-(ethoxymethyl)-2-(3,4,5-trichloro-2-thienyl)-5-(trifluoromethyl)pyrrole-3-carbonitrile;

2-(5-chloro-2-thienyl)-5-(trifluoromethyl)pyrrole-3-carbonitrile;

2-(p-chlorophenyl)-4-(4,5-dibromo-3-thienyl)-3-nitro-5-(trifluoromethyl)pyrrole;

2-(3,4,5-trichloro-2-thienyl)-5-(trifluoromethyl)pyrrole-3-carbonitrile;

4-bromo-2-(4,5-dibromo-2-thienyl)-5-(trifluoromethyl)pyrrole-3-carbonitrile;

2-(p-chlorophenyl)-3-nitro-4-(5-nitro-2-thienyl)-5-(trifluoromethyl)pyrrole; and 4-bromo-2-chloro-5-(5-chloro-2-thienyl)pyrrole-3-carbonitrile.

33. The method according to claim 26 wherein the compound is applied to the plants or to the soil or water in which they are growing at a rate of about 0.1 kg/ha to 4.0 kg/ha.

34. A composition for controlling insects and acarina which comprises an inert liquid or solid carrier and an insecticidally or acaricidally effective amount of a compound having the structural formula

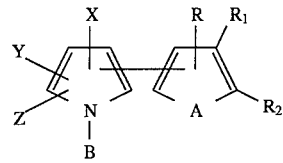

wherein R, $R_1$, $R_2$, A, X, Y, Z and B are as described in claim 1.

35. The composition according to claim 34 wherein R, $R_1$, $R_2$, A, X, Y, Z and D are as described in claim 2.

36. The composition according to claim 35 wherein R, $R_1$, $R_2$, A, X, Y, Z and D are as described in claim 3.

37. The composition according to claim 36 wherein R, $R_1$, $R_2$, A, X, Y, Z and D are as described in claim 4.

38. The composition according to claim 36 wherein

R, $R_1$ and $R_2$ are each independently hydrogen, halogen or $NO_2$, and when $R_1$ and $R_2$ are taken together with the carbon atoms to which they are attached, they may form a ring in which $R_1R_2$ is represented by the structure: —CH=CH—CH=CH—;

A is O or S;

X is CN or $NO_2$;

Y is halogen, $CF_3$ or
phenyl optionally substituted with one or more halogen atoms,
$NO_2$ groups,
CN groups,
$C_1$–$C_4$ alkyl groups optionally substituted with one or more halogen atoms, or
$C_1$–$C_4$ alkoxy groups optionally substituted with one or more halogen atoms;

Z is hydrogen, halogen or $CF_3$; and

B is hydrogen or $C_1$–$C_6$ alkyl substituted with one $C_1$–$C_4$ alkoxy group.

39. The composition according to claim 38 wherein

R, $R_1$ and $R_2$ are each independently hydrogen, halogen or $NO_2$;

A is O or S;

X is CN or NO$_2$;

Y is halogen, CF$_3$ or phenyl optionally substituted with one or more halogen atoms, NO$_2$ groups, CN groups, C$_1$–C$_4$ alkyl groups optionally substituted with one or more halogen atoms, or C$_1$–C$_4$ alkoxy groups optionally substituted with one or more halogen atoms;

Z is CF$_3$; and

D is hydrogen or C$_1$–C$_6$ alkyl substituted with one C$_1$–C$_4$ alkoxy group.

40. The composition according to claim 34, further comprising a pesticidally effective amount of one or more other pesticidal agents.

* * * * *